(12) United States Patent
Garber et al.

(10) Patent No.: US 11,131,723 B2
(45) Date of Patent: Sep. 28, 2021

(54) SINGLE CONTROLLER FOR WEARABLE SENSOR UNIT THAT INCLUDES AN ARRAY OF MAGNETOMETERS

(71) Applicant: HI LLC, Los Angeles, CA (US)

(72) Inventors: Stephen Garber, Santa Monica, CA (US); Teague Lasser, Los Angeles, CA (US); Benjamin Siepser, Los Angeles, CA (US); Jamu Alford, Simi Valley, CA (US); Dakota Blue Decker, Culver City, CA (US); Jeffery Kang Gormley, Chatsworth, CA (US); Michael Henninger, Austin, TX (US); Scott Michael Homan, Culver City, CA (US); Micah Ledbetter, Sunnyvale, CA (US); Jerry Leung, Marina Del Rey, CA (US); Hooman Mohseni, Wilmette, IL (US); Ethan Pratt, Santa Clara, CA (US); Scott Jeremy Seidman, Glenview, IL (US)

(73) Assignee: HI LLC, Los Angeles, CA (US)

( * ) Notice: Subject to any disclaimer, the term of this patent is extended or adjusted under 35 U.S.C. 154(b) by 0 days.

(21) Appl. No.: 16/862,826

(22) Filed: Apr. 30, 2020

(65) Prior Publication Data

US 2020/0348369 A1 Nov. 5, 2020

Related U.S. Application Data

(60) Provisional application No. 62/842,818, filed on May 3, 2019, provisional application No. 62/933,160, filed (Continued)

(51) Int. Cl.
*G01R 33/00* (2006.01)
*G01R 33/032* (2006.01)
(Continued)

(52) U.S. Cl.
CPC ........ *G01R 33/0082* (2013.01); *A61B 5/0077* (2013.01); *A61B 5/05* (2013.01);
(Continued)

(58) Field of Classification Search
CPC .............. G01R 33/0082; G01R 33/007; G01R 33/0011; G01R 33/095; G01R 33/26;
(Continued)

(56) References Cited

U.S. PATENT DOCUMENTS 3,173,082 A 3/1965 Bell et al.
3,257,608 A 6/1966 Bell et al.
(Continued)

FOREIGN PATENT DOCUMENTS

CN 104730484 6/2015
CN 107562188 1/2018
(Continued)

OTHER PUBLICATIONS

Tierney, Tim M., et al. "Cognitive neuroscience using wearable magnetometer arrays: Non-invasive assessment of language function." NeuroImage 181 (2018): 513-520. (Year: 2018).*
(Continued)

*Primary Examiner* — Christopher P McAndrew
(74) *Attorney, Agent, or Firm* — ALG Intellectual Property, LLC

(57) ABSTRACT

An exemplary magnetic field measurement system includes a wearable sensor unit and a single controller. The wearable sensor unit includes a plurality of magnetometers and a magnetic field generator configured to generate a compensation magnetic field configured to actively shield the magnetometers from ambient background magnetic fields. The single controller is configured to interface with the magnetometers and the magnetic field generator.

20 Claims, 43 Drawing Sheets

Related U.S. Application Data on Nov. 8, 2019, provisional application No. 62/933,167, filed on Nov. 8, 2019, provisional application No. 62/933,169, filed on Nov. 8, 2019, provisional application No. 62/933,170, filed on Nov. 8, 2019, provisional application No. 62/933,287, filed on Nov. 8, 2019, provisional application No. 62/933,288, filed on Nov. 8, 2019, provisional application No. 62/933,289, filed on Nov. 8, 2019, provisional application No. 62/933,174, filed on Nov. 8, 2019, provisional application No. 62/967,787, filed on Jan. 30, 2020, provisional application No. 62/967,797, filed on Jan. 30, 2020, provisional application No. 62/967,803, filed on Jan. 30, 2020, provisional application No. 62/967,804, filed on Jan. 30, 2020, provisional application No. 62/967,813, filed on Jan. 30, 2020, provisional application No. 62/967,818, filed on Jan. 30, 2020, provisional application No. 62/967,823, filed on Jan. 30, 2020.

(51) Int. Cl.

| | | |
|---|---|---|
| *A61B 5/05* | (2021.01) | |
| *A61B 5/00* | (2006.01) | |
| *G01R 33/26* | (2006.01) | |
| *G01R 33/09* | (2006.01) | |
| *A61B 5/245* | (2021.01) | |
| *H01F 7/20* | (2006.01) | |
| *H01F 27/28* | (2006.01) | |
| *H01F 27/36* | (2006.01) | |
| *H05K 1/18* | (2006.01) | |

(52) U.S. Cl.
CPC ............ *A61B 5/245* (2021.01); *A61B 5/4064* (2013.01); *A61B 5/6802* (2013.01); *A61B 5/6803* (2013.01); *G01R 33/007* (2013.01); *G01R 33/0011* (2013.01); *G01R 33/0017* (2013.01); *G01R 33/0047* (2013.01); *G01R 33/032* (2013.01); *G01R 33/095* (2013.01); *G01R 33/26* (2013.01); *H01F 7/20* (2013.01); *H01F 27/2804* (2013.01); *H01F 27/36* (2013.01); *H05K 1/18* (2013.01); *A61B 2562/0223* (2013.01); *A61B 2562/04* (2013.01); *A61B 2562/18* (2013.01); *A61B 2562/222* (2013.01); *A61B 2562/227* (2013.01); *H05K 2201/10151* (2013.01)

(58) Field of Classification Search
CPC ............ G01R 33/0017; G01R 33/0047; G01R 33/032; G01R 33/025; A61B 5/245; A61B 5/4064; A61B 5/7225; A61B 2562/046; H01F 7/20; H01F 27/2804; H01F 27/36; H05K 1/18
USPC .......................................................... 324/244
See application file for complete search history.

(56) References Cited

U.S. PATENT DOCUMENTS

| | | |
|---|---|---|
| 3,495,161 A | 2/1970 | Bell |
| 3,501,689 A | 3/1970 | Robbiano |
| 3,513,381 A | 5/1970 | Happer, Jr. |
| 4,193,029 A | 3/1980 | Cioccio et al. |
| 4,951,674 A | 8/1990 | Zanakis et al. |
| 5,189,368 A | 2/1993 | Chase |
| 5,192,921 A | 3/1993 | Chantry et al. |
| 5,225,778 A | 7/1993 | Chaillout et al. |
| 5,254,947 A | 10/1993 | Chaillout et al. |
| 5,309,095 A | 5/1994 | Ahonen et al. |
| 5,442,289 A | 8/1995 | Dilorio et al. |
| 5,444,372 A | 8/1995 | Wikswo, Jr. et al. |
| 5,471,985 A | 12/1995 | Warden |
| 5,506,200 A | 4/1996 | Hirschkoff et al. |
| 5,526,811 A | 6/1996 | Lypchuk |
| 5,713,354 A | 2/1998 | Warden |
| 6,144,872 A | 11/2000 | Graetz |
| 6,339,328 B1 | 1/2002 | Keene et al. |
| 6,472,869 B1 | 10/2002 | Upschulte et al. |
| 6,665,553 B2 | 12/2003 | Kandori et al. |
| 6,806,784 B2 | 10/2004 | Hollberg et al. |
| 6,831,522 B2 | 12/2004 | Kitching et al. |
| 7,038,450 B2 | 5/2006 | Romalis et al. |
| 7,102,451 B2 | 9/2006 | Happer et al. |
| 7,145,333 B2 | 12/2006 | Romalis et al. |
| 7,521,928 B2 | 4/2009 | Romalis et al. |
| 7,656,154 B2 | 2/2010 | Kawabata et al. |
| 7,826,065 B1 | 11/2010 | Okandan et al. |
| 7,872,473 B2 | 1/2011 | Kitching et al. |
| 7,994,783 B2 | 8/2011 | Ledbetter et al. |
| 8,054,074 B2 | 11/2011 | Ichihara et al. |
| 8,212,556 B1 | 7/2012 | Schwindt et al. |
| 8,258,884 B2 | 9/2012 | Borwick, III et al. |
| 8,319,156 B2 | 11/2012 | Borwick, III et al. |
| 8,334,690 B2 | 12/2012 | Kitching et al. |
| 8,373,413 B2 | 2/2013 | Sugioka |
| 8,405,389 B2 | 3/2013 | Sugioka et al. |
| 8,587,304 B2 | 11/2013 | Budker et al. |
| 8,836,327 B2 | 9/2014 | French et al. |
| 8,906,470 B2 | 12/2014 | Overstolz et al. |
| 8,941,377 B2 | 1/2015 | Mizutani et al. |
| 9,095,266 B1 | 8/2015 | Fu |
| 9,116,201 B2 | 8/2015 | Shah et al. |
| 9,140,590 B2 | 9/2015 | Waters et al. |
| 9,140,657 B2 | 9/2015 | Ledbetter et al. |
| 9,169,974 B2 | 10/2015 | Parsa et al. |
| 9,244,137 B2 | 1/2016 | Kobayashi et al. |
| 9,291,508 B1 | 3/2016 | Biedermann et al. |
| 9,343,447 B2 | 3/2016 | Parsa et al. |
| 9,366,735 B2 | 6/2016 | Kawabata et al. |
| 9,383,419 B2 | 7/2016 | Mizutani et al. |
| 9,395,425 B2 | 7/2016 | Diamond et al. |
| 9,417,293 B2 | 8/2016 | Schaffer et al. |
| 9,429,918 B2 | 8/2016 | Parsa et al. |
| 9,568,565 B2 | 2/2017 | Parsa et al. |
| 9,575,144 B2 | 2/2017 | Kornack et al. |
| 9,601,225 B2 | 3/2017 | Parsa et al. |
| 9,638,768 B2 | 5/2017 | Foley et al. |
| 9,639,062 B2 | 5/2017 | Dyer et al. |
| 9,677,905 B2 | 6/2017 | Waters et al. |
| 9,726,626 B2 | 8/2017 | Smith et al. |
| 9,726,733 B2 | 8/2017 | Smith et al. |
| 9,791,536 B1 | 10/2017 | Alem et al. |
| 9,829,544 B2 | 11/2017 | Bulatowicz |
| 9,846,054 B2 | 12/2017 | Waters et al. |
| 9,851,418 B2 | 12/2017 | Wolf et al. |
| 9,869,731 B1 | 1/2018 | Hovde et al. |
| 9,915,711 B2 | 3/2018 | Kornack et al. |
| 9,927,501 B2 | 3/2018 | Kim et al. |
| 9,948,314 B2 | 4/2018 | Dyer et al. |
| 9,964,609 B2 | 5/2018 | Ichihara et al. |
| 9,964,610 B2 | 5/2018 | Shah et al. |
| 9,970,999 B2 | 5/2018 | Larsen et al. |
| 9,995,800 B1 | 6/2018 | Schwindt et al. |
| 10,024,929 B2 | 7/2018 | Parsa et al. |
| 10,088,535 B1 | 10/2018 | Shah |
| 10,162,016 B2 | 12/2018 | Gabrys et al. |
| 10,371,764 B2 | 8/2019 | Morales et al. |
| 10,772,561 B2 | 9/2020 | Donaldson |
| 2004/0232912 A1 | 11/2004 | Tsukamoto et al. |
| 2005/0007118 A1 | 1/2005 | Kitching et al. |
| 2005/0046851 A1 | 3/2005 | Riley, Jr. et al. |
| 2005/0206377 A1 | 9/2005 | Romalis et al. |
| 2006/0197523 A1* | 9/2006 | Palecki ............ G01V 3/081 324/244 |
| 2007/0120563 A1 | 5/2007 | Kawabata et al. |
| 2007/0167723 A1 | 7/2007 | Park et al. |
| 2007/0205767 A1 | 9/2007 | Xu et al. |

(56) References Cited

U.S. PATENT DOCUMENTS

| | | | |
|---|---|---|---|
| 2008/0255498 A1* | 10/2008 | Houle | A61C 17/0211 |
| | | | 604/20 |
| 2009/0066535 A1* | 3/2009 | Patel | E21B 47/00 |
| | | | 340/853.2 |
| 2009/0079426 A1 | 3/2009 | Anderson | |
| 2009/0101806 A1 | 4/2009 | Masuda | |
| 2010/0219820 A1 | 9/2010 | Skidmore et al. | |
| 2011/0062956 A1 | 3/2011 | Edelstein et al. | |
| 2012/0112749 A1 | 5/2012 | Budker et al. | |
| 2013/0082700 A1 | 4/2013 | Mizutani et al. | |
| 2013/0082701 A1 | 4/2013 | Mizutani et al. | |
| 2013/0265042 A1 | 10/2013 | Kawabata et al. | |
| 2014/0031642 A1* | 1/2014 | Kimchy | A61B 6/4258 |
| | | | 600/302 |
| 2014/0306700 A1 | 10/2014 | Kamada et al. | |
| 2014/0354275 A1 | 12/2014 | Sheng et al. | |
| 2015/0022200 A1 | 1/2015 | Ichihara et al. | |
| 2015/0054504 A1 | 2/2015 | Ichihara et al. | |
| 2015/0378316 A1 | 12/2015 | Parsa et al. | |
| 2016/0061913 A1 | 3/2016 | Kobayashi et al. | |
| 2016/0116553 A1 | 4/2016 | Kim et al. | |
| 2016/0223627 A1 | 8/2016 | Shah et al. | |
| 2016/0299252 A1* | 10/2016 | Zacharko | E21B 47/024 |
| 2016/0313417 A1 | 10/2016 | Kawabata et al. | |
| 2016/0360997 A1* | 12/2016 | Yadav | A61B 5/1072 |
| 2017/0023653 A1 | 1/2017 | Kobayashi et al. | |
| 2017/0023654 A1 | 1/2017 | Kobayashi et al. | |
| 2017/0067969 A1 | 3/2017 | Butters et al. | |
| 2017/0090568 A1* | 3/2017 | Chen | G06F 3/014 |
| 2017/0199138 A1 | 7/2017 | Parsa et al. | |
| 2017/0261564 A1 | 9/2017 | Gabrys et al. | |
| 2017/0331485 A1 | 11/2017 | Gobet et al. | |
| 2017/0343617 A1 | 11/2017 | Manickam et al. | |
| 2017/0343695 A1 | 11/2017 | Stetson et al. | |
| 2017/0364164 A1* | 12/2017 | Kim | G06F 3/03545 |
| 2018/0003777 A1 | 1/2018 | Sorenson et al. | |
| 2018/0038921 A1 | 2/2018 | Parsa et al. | |
| 2018/0100749 A1 | 4/2018 | Waters et al. | |
| 2018/0128885 A1 | 5/2018 | Parsa et al. | |
| 2018/0156875 A1 | 6/2018 | Herbsommer et al. | |
| 2018/0219353 A1 | 8/2018 | Shah | |
| 2018/0238974 A1 | 8/2018 | Shah et al. | |
| 2018/0313908 A1 | 11/2018 | Knappe et al. | |
| 2018/0313913 A1 | 11/2018 | Denatale et al. | |
| 2018/0368716 A1* | 12/2018 | Govari | A61B 5/318 |
| 2019/0391213 A1 | 12/2019 | Alford | |
| 2020/0025844 A1 | 1/2020 | Alford et al. | |
| 2020/0057115 A1 | 2/2020 | Jiménez-Martínez | |
| 2020/0057116 A1 | 2/2020 | Zorzos et al. | |
| 2020/0072916 A1 | 3/2020 | Alford | |
| 2020/0088811 A1 | 3/2020 | Mohseni | |

FOREIGN PATENT DOCUMENTS

| | | |
|---|---|---|
| EP | 2738627 | 6/2014 |
| EP | 2380029 | 10/2015 |
| EP | 3037836 | 9/2017 |
| JP | 2016109665 | 6/2016 |
| JP | 2018004462 | 1/2018 |
| WO | 2005081794 | 9/2005 |
| WO | 2014031985 | 2/2014 |
| WO | 2017095998 | 6/2017 |

OTHER PUBLICATIONS

Yin, Liu, Yu Jin, and Mo Zeqiang. "The Signal Detection and Control Circuit Design for Confocal Auto-Focus System." MATEC Web of Conferences. vol. 40. EDP Sciences, 2016. (Year: 2016).*

Stern, Liron, et al. "Nanoscale light-matter interactions in atomic cladding waveguides." Nature communications 4.1 (2013): 1-7. (Year: 2013).*

Knappe,S. et al.,"Optically-Pumped Magnetometers for MEG," Springer-Verlag Berlin Heidelberg, 2014; pp. 993-999; DOI: 10.1007/978-3-642-33045-2_49.

Kominis,I.K. et al.,"A Subfemtotesla Multichannel Atomic Magnetometer," Nature Publishing Group, vol. 422(6932), p. 596-599. Apr. 2003.

Korth,H. et al.,"Miniature Atomic Scalar Magnetometer for Space Based on the Rubidium Isotope 87 Rb," J. Geophys. Res. Space Physics, 121, 7870-7880, doi:10.1002/2016JA022389.

Lee,S.K. et al.,"Calculation of Magnetic Field Noise from High-Permeability Magnetic Shields and Conducting Objects with Simple Geometry," Journal of Applied Physics. 103. 084904-084904. 10.1063/1.2885711.

Lee,H.J. et al.,"Flat-Response Spin-Exchange Relaxation Free Atomic Magnetometer Under Negative Feedback," Optics Express. 22. 10.1364/OE.22.019887.

Lenz,J. et al.,"Magnetic Sensors and Their Applications," IEEE Sensors Journal, 6(3), pp. 631-649.

Li,S. et al.,"Optical Rotation in Excess of 100 Rad Generated by Rb Vapor in a Multipass Cell;" Phys. Rev. A. 84. 10.1103/PhysRevA.84.061403.

Lorenz,V.O. et al.,"High-Density, High-Temperature Alkall Vapor Cell," Review of Scientific Instruments, 79, 123104, 4 pages, 2008.

Masuda,Y. et al.,"3He Polarization via Optical Pumping in a Birefringent Cell," Applied Physics Letters. 87. 10.1063/1.2008370.

Maze,J.R. et al.,"Nanoscale Magnetic Sensing with an Individual Electronic Spin in Diamond," Nature, 455(7213), 644. Oct. 2008.

Navau,C. et al.,"Magnetic Energy Harvesting and Concentration at a Distance by Transformation Optics," Physical Review Letters. 109. 263903. 10.1103/PhysRevLett.109.263903.

Neuman,J.A. et al.,"Robust High-Temperature Sapphire Cell for Metal Vapors," Review of Scientific Instruments, vol. 66, Issue 4, Apr. 1995, pp. 3021-3023.

Ryan,L.J. et al.,"Miniature Vector Laser Magnetometer Measurements of Earth's Field," May 10, 2004. 4 pgs.

Sander,T.H. et al.,"Magnetoencephalography with a Chip-Scale Atomic Magnetometer," Biomed Opt Express. 2012;3(5):981-90.

Schoenmaker,J. et al.,"Magnetic Flux Amplification by Lenz Lenses," The Review of Scientific Instruments. 84. 085120. 10.1063/1.4819234.

Schultze,V. et al.,"An Optically Pumped Magnetometer Working in the Light-Shift Dispersed Mz Mode," Sensors, 2017, 17, 561; doi:10.3390/s17030561.

Seltzer,S.J. et al.,"Developments in Alkali-Metal Atomic Magnetometry," Nov. 1, 2008 (Nov. 1, 2008), XP055616618, ISBN: 978-0-549-93355-7. https://physics.princeton.edu/atomic/romalis/papers/Seltzer%20Thesis.pdf. pp. 148-159.

Seltzer,S.J. et al.,"High-Temperature Alkall Vapor Cells with Anti-Relaxation Surface Coatings," Journal of Applied Physics. 106. 114905-114905. 10.1063/1.3236649.

Seltzer,S.J. et al., "Unshielded Three-Axis Vector Operation of a Spin-Exchange-Relaxation-Free Atomic Magnetometer," Applied Physics Letters 85.20 (2004): 4804-4806.

Sheng,D. et al.,"A Microfabricated Optically-Pumped Magnetic Gradiometer," Applied Physics Letters. 110. 10.1063/1.4974349.

Sheng,D. et al.,"Subfemtotesla Scalar Atomic Magnetometry Using Multipass Cells," Physical Review Letters. 110. 160802. 10.1103/PhysRevLett.110.160802.

Slocum,R.E. et al.,"Design and Operation of the Miniature Vector Laser Magnetometer," NASA Earth Science Technology Conference 2003.

Slocum, et al.,"Self-Calibrating Vector Magnetometer for Space," https://esto.nasa.gov/conferences/esto-2002/Papers/B3P4(Slocum).pdf.

Tierney,T.M. et al.,"Cognitive Neuroscience Using Wearable Magnetometer Arrays: Non-Invasive Assessment of Language Function," NeuroImage vol. 181 (2018) pp. 513-520. https://doi.org/10.1016/j.neuroimage-2018.07.035.

Vovrosh,J. et al.,"Additive Manufacturing of Magnetic Shielding and Ultra-High Vacuum Flange for Cold Atom Sensors," Scientific Reports. 8. 10.1038/541598-018-20352-x.

Zetter,R. et al.,"Optical Co-registration of MRI and On-scalp MEG," Scientific Reports (2019) 9:5490. https://doi.org/10.1038/s41598-019-41763-4.

(56) References Cited

OTHER PUBLICATIONS

Alem,O. et al.,"Magnetic Field Imaging with Microfabricated Optically-Pumped Magnetometers," Opt. Express 25, 7849-7858 (2017).
Allred,J.C. et al.,"High-Sensitivity Atomic Magnetometer Unaffected by Spin-Exchange Relaxation," Physical Review Letters, 89(13), 130801.
Balabas, et al.,"Polarized Alkali Vapor with Minute-Long Transverse Spin-Relaxation Time," Phys. Rev. Lett. 105, 070801 Published Aug. 12, 2010.
Baranga,A.B. et al.,"An Atomic Magnetometer for Brain Activity Imaging," Real Time Conference 2005. 14th IEEE—NPSS. pp. 417-418.
Barbieri,F. et al.,"Local Recording of Biological Magnetic Fields Using Giant Magneto Resistance-Based Micro-Probes," Scientific Reports, 6, 39330.
Borna,A. et al.,"A 20-Channel Magnetoencephalography System Based on Optically Pumped Magnetometers," Physics in Medicine & Biology 62.23 (2017): 8909.
Boto,E. et al.,"Moving Magnetoencephalography Towards Real World Applications with a Wearable System," Nature, vol. 555, pp. 657-661.
Budker,D. et al.,"Optical Magnetometry," Nature Physics. 2008. https://arxiv.org/abs/physics/0611246v1.
Colombo,A. et al.,"Four-Channel Optically Pumped Atomic Magnetometer for Magnetoencephalography," Opt. Express 24, 15403-15416 (2016).
Dang,H.B. et al.,"Ultra-High Sensitivity Magnetic Field and Magnetization Measurements with an Atomic Magnetometer," Applied Physics Letters. 97. 10.1063/1.3491215.
Dong,H. et al.,"Atomic-Signal-Based Zero-Field Finding Technique for Unshielded Atomic Vector Magnetometer," IEEE Sensors Journal, IEEE Service Center, New York, NY, US, vol. 13, No. 1. Jan. 1, 2013 (Jan. 1, 2013), pp. 186-189.
Donley,E.A. et al.,"Demonstration of High-Performance Compact Magnetic Shields for Chip-Scale Atomic Devices," The Review of Scientific Instruments. 78. 083102.
Dupont-Roc,J. et al.,"Detection of Very Weak Magnetic Fields (10-9gauss) by 87Rb Zero-Field Level Crossing Resonances," Physics Letters A—Phys Lett A. 28. 638-639 10.1016/0375-9601(69) 90480-0.
Fang,J. et al.,"In Situ Triaxial Magnetic Field Compensation for the Spin-Exchange-Relaxation-Free Atomic Magnetometer," Review of Scientific Instruments, 83(10), p. 103104.
Griffith,C. et al.,"Miniature Atomic Magnetometer Integrated with Flux Concentrators," Applied Physics Letters—Appl Phys Lett. 94. 10.1063/1.3056152.
Hamalainen,M. et al.,"Magnetoencephalograph—Theory, Instrumentation, and Applications to Noninvasive Studies of the Working Human Brain," Reviews of Modern Physics, vol. 65, Issue 2. 413-497.
Hill,R.M. et al.,"A Tool for Functional Brain Imaging with Lifespan Compliance," Nature Communications (2019) 10:4785. https://doi.org/10.1038/s41467-019-12486-x.
Hill,R.M. et al.,"Multi-Channel Whole-Head OPM-MEG: Helmet Design and a Comparison with a Conventional System," NeuroImage vol. 219 (2020) 116995. https://doi.org/10.1016/j.neuroimage.2020.116995.
Hu,Y. et al.,"Reduction of Far Off-Resonance Laser Frequency Drifts Based on the Second Harmonic of Electro-Optic Modulator Detection in the Optically Pumped Magnetometer," Applied Optics. 56. 5927. 10.1364/AO.56.005927.
Huang,H. et al.,"Single-Beam Three-Axis Atomic Magnetometer," Applied Physics Letters 109.6 (2016): 062404. (Year: 2016).
Hunter,D. et al.,"Free-Induction-Decay Magnetometer Based on a Microfabricated Cs Vapor Cell," Physical Review Applied (10). ISSN 2331-7019.
Ijsselsteijn,R. et al. ,"A Full Optically Operated Magnetometer Array: An Experimental Study," The Review of Scientific Instruments. 83. 113106. 10.1063/1.4766961.
Jackson Kimball, D.F. et al.,"Magnetic Shielding and Exotic Spin-Dependent Interactions," Physical Review D. 94. 10.1103/PhysRev.94.082005.
Jimenez-Martinez,R. et al.,"Sensitivity Comparison of Mx and Frequency-Modulated Bell-Bloom Cs Magnetometers in a Microfabricated Cell," IEEE Transactions on Instrumentation and Measurement, 59(2), 372-378.
Kim,K. et al.,"Multi-Channel Atomic Magnetometer for Magnetoencephalography: A Configuration Study," NeuroImage 89 (2014) 143-151 https://physics.princeton.edu/romalis/papers/Kim_2014.pdf.
Kim,Y.J. et al.,"Ultra-Sensitive Magnetic Microscopy with an Optically Pumped Magnetometer," Scientific Reports. 6. 24773. 10.1038/srep24773.
Non-Final Office Action received in U.S. Appl. No. 16/862,856 dated Apr. 26, 2021.
Non-Final Office Action received in U.S. Appl. No. 16/862,879 dated Apr. 26, 2021.
Bell, et al.,"Optically Driven Spin Precession", Physical Review Letters Mar. 15, 1961; vol. 6, No. 6.
Bloom, et al.,"Principles of Operation of the Rubidium Vapor Magnetometer", Jan. 1962 / vol. 1, No. 1 / Applied Optics 61.
Borna, et al.,"Non-Invasive Functional-Brain-Imaging with an OPM-based Magnetoencephalography System", PLoS ONE 15 (1): e0227684. https://doi.org/10.1371/journal.pone.0227684.
De Cheveigne, et al.,"Decoding the auditory brain with canonical component analysis", https://doi.org/10.1016/j.neuroimage.2018.01.033 NeuroImage 172 (2018) 206-216.
Gascoyne, et al.,"Localising the auditory N1m with event-related beamformers: localisation accuracy following trilateral and unilateral stimulation", Scientific Reports, 6:31052 DOI: 10 1038/srep31052.
Griffith, et al.,"Femtotesla atomic magnetometry in a microfabricated vapor cell", Dec. 20, 2010 / vol. 18, No. 26 / Optics Express 27167.
Happer, et al.,"Optical Pumping", Reviews of Modern Physics vol. 44, No. 2; Apr. 1972.
Horowitz, et al.,"The Art of Electronics", Cambridge University Press, 1989; ISBN 978-0-521-37095-0.
Iivanainen, et al.,"Measuring MEG closer to the brain: Performance of on-scalp sensor arrays", NeuroImage 147 (2017) 542-553 http://dx.doi.org/10.1016/j.neuroimage.2016.12.048.
Iivanainen, et al.,"On-scalp MEG system utilizing an actively shielded array of optically-pumped magnetometers", NeuroImage 194 (2019) 244-258 https://doi.org/10.1016/j.neuroimage.2019.03.022.
Kitching, et al.,"Atomic Sensors—A Review", IEEE Sensors Journal, vol. 11, No. 9, Sep. 2011.
Kitching, et al.,"Chip-scale atomic devices", Appl. Phys. Rev. 5, 031302 (2018); https://doi.org/10.1063/1.5026238.
Kitching, et al.,"Chip-Scale Atomic Devices: Precision Atomic Instruments Based on MEMS", https://tsapps.nist.gov/publication/get_pdf.cfm?pub_id=901006 Proc. 2008 Symposium on Frequency Standards and Metrology, Pacific Grove, CO.
Ledbetter, et al.,"Spin-exchange-relaxation-free magnetometry with Cs vapor", Physical Review A 77, 033408 (2008).
Lightfoot, et al.,"Summary of the N1-P2 Cortical Auditory Evoked Potential to Estimate the Auditory Threshold in Adults", Seminars in Hearing Feb. 2016; 37(1): 1-8.
Mellinger, et al.,"An MEG-based Brain-Computer Interface (BCI)", Neuroimage. Jul. 1, 2007; 36(3): 581-593.
Okada, et al.,"Experimental analysis of distortion of magnetoencephalography signals by the skull", Clinical Neurophysiology 110 (1999) 230-238.
Pratt, et al.,"Kernel Flux: A Whole-Head 432-Magnetometer Optically-Pumped Magnetoencephalography (OP-MEG) System For Brain Activity Imaging During Natural Human Experiences", SPIE Photonics West Conference (Mar. 6, 2021).
Purcell, et al.,"Influence of Collisions Upon Population of Hyperfine States in Hydrogen", Astrophysical Journal, vol. 124, p. 542.
Roberts, et al.,"Towards OPM-MEG in a virtual reality environment", NeuroImage 199 (2019) 408-417.

(56) References Cited

OTHER PUBLICATIONS

Robinson, et al.,"Developing Next-Generation Brain Sensing Technologies—A Review", IEEE Sensors Journal, vol. 19, No. 22, Nov. 15, 2019.
Shah, et al.,"Subpicotesla atomic magnetometry with a microfabricated vapour cell", nature photonics vol. 1 Nov. 2007; doi:10.1038/nphoton.2007.201.
Tierney, et al.,"Optically pumped magnetometers: From quantum origins to multi-channel magnetoencephalography", NeuroImage 199 (2019) 598-608.
Virtanen, et al.,"Replicability of MEG and EEG measures of the auditory N1/N1m-response", Electroencephalography and clinical Neurophysiology 108 (1998) 291-298.
Zhang, et al.,"Recording brain activities in unshielded Earth's field with optically pumped atomic magnetometers", Science Advances 2020; 6 : eaba8792 Jun. 12, 2020.
Wolpaw, et al.,"An EEG-based brain-computer interface for cursor control", Electroencephalography and clinical Neurophysiology, 1991, 78:252-259.

* cited by examiner

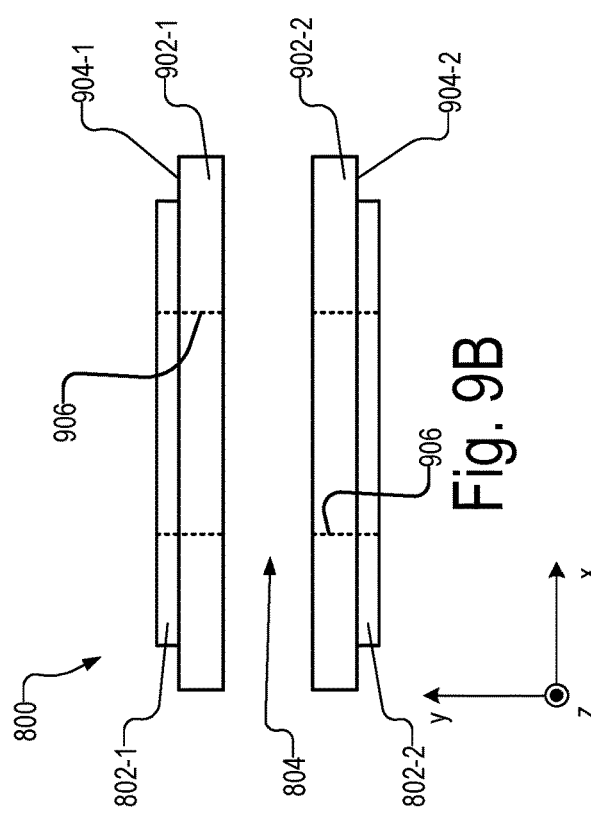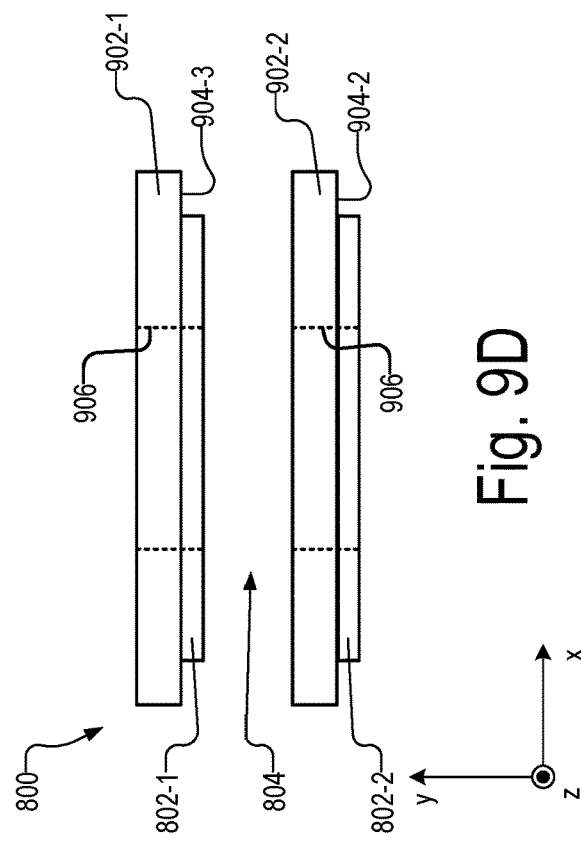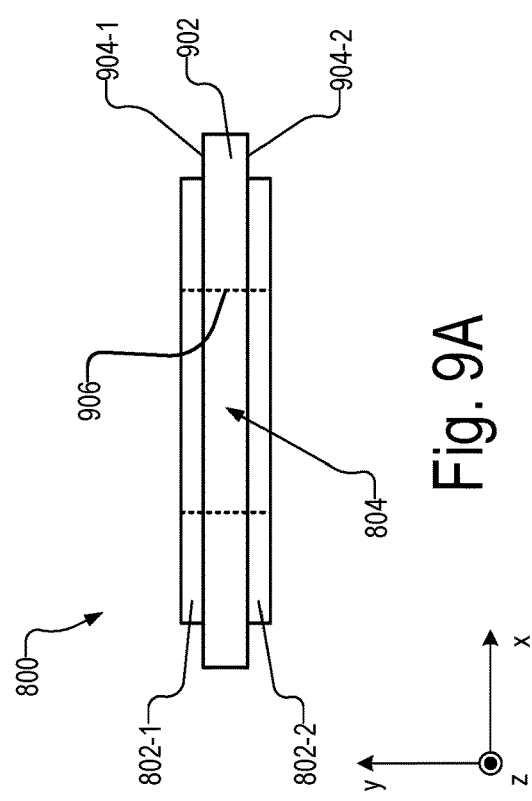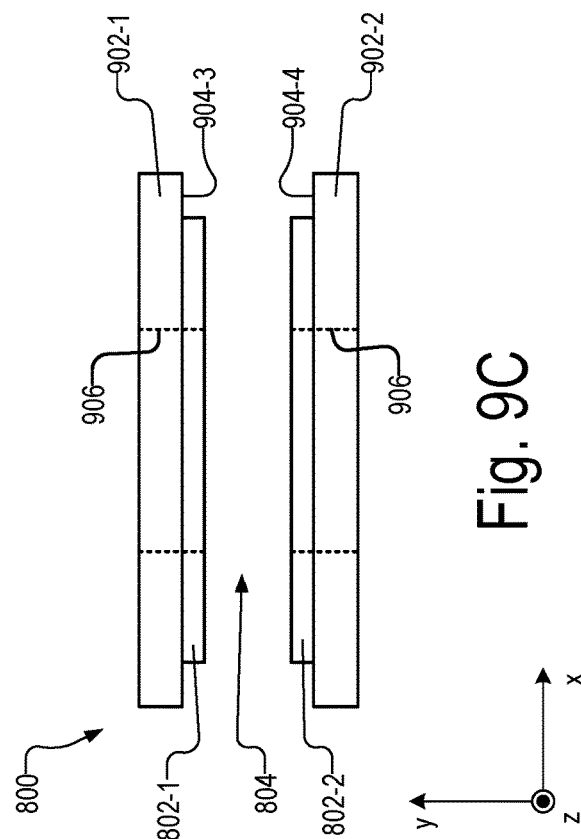

SINGLE CONTROLLER FOR WEARABLE SENSOR UNIT THAT INCLUDES AN ARRAY OF MAGNETOMETERS

RELATED APPLICATIONS

The present application claims priority under 35 U.S.C. § 119(e) to U.S. Provisional Patent Application No. 62/842,818, filed on May 3, 2019, and to U.S. Provisional Patent Application No. 62/933,160, filed on Nov. 8, 2019, and to U.S. Provisional Patent Application No. 62/933,167, filed on Nov. 8, 2019, and to U.S. Provisional Patent Application No. 62/933,169, filed on Nov. 8, 2019, and to U.S. Provisional Patent Application No. 62/933,170, filed on Nov. 8, 2019, and to U.S. Provisional Patent Application No. 62/933,287, filed on Nov. 8, 2019, and to U.S. Provisional Patent Application No. 62/933,288, filed on Nov. 8, 2019, and to U.S. Provisional Patent Application No. 62/933,289, filed on Nov. 8, 2019, and to U.S. Provisional Patent Application No. 62/933,174, filed on Nov. 8, 2019, and to U.S. Provisional Patent Application No. 62/967,787, filed on Jan. 30, 2020, and to U.S. Provisional Patent Application No. 62/967,797, filed on Jan. 30, 2020, and to U.S. Provisional Patent Application No. 62/967,803, filed on Jan. 30, 2020, and to U.S. Provisional Patent Application No. 62/967,804, filed on Jan. 30, 2020, and to U.S. Provisional Patent Application No. 62/967,813, filed on Jan. 30, 2020, and to U.S. Provisional Patent Application No. 62/967,818, filed on Jan. 30, 2020, and to U.S. Provisional Patent Application No. 62/967,823, filed on Jan. 30, 2020. These applications are incorporated herein by reference in their respective entireties.

BACKGROUND INFORMATION

Existing systems for observing or measuring weak magnetic fields (e.g., magnetic fields generated by the brain) typically utilize Superconductive Quantum Interference Devices (SQUIDs) or optical magnetometry. SQUID systems require cryogenic cooling, which is prohibitively costly and bulky and requires a lot of maintenance, which preclude their use in mobile or wearable devices. Optical magnetometry uses optical methods to measure a magnetic field with very high accuracy—on the order of $1 \times 10^{-15}$ Tesla. Of particular interest for their high-sensitivity, Optically Pumped Magnetometers (OPMs) have an alkali vapor gas cell that contains alkali metal atoms in a combination of gas, liquid, or solid states (depending on temperature). The gas cell may contain a quenching gas, buffer gas, or specialized antirelaxation coatings or any combination thereof. The size of the gas cells can vary from a fraction of a millimeter up to several centimeters.

Magnetoencephalography (MEG), the measurement of magnetic fields generated by the brain, and other types of magnetic field sensing may be performed by a plurality of magnetometers (e.g., a collection of discrete OPMs). A conventional magnetometer is controlled by a dedicated controller, which has an independent clock used to drive various components within the magnetometer and receive signals from various components within the magnetometer. Accordingly, in a conventional configuration that has an array of magnetometers, an array of controllers (and hence an array of independent clocks) are used. The clocks are not perfectly synchronized, which may lead to crosstalk between signals. This is disadvantageous for many reasons.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements. Furthermore, the figures are not necessarily drawn to scale as one or more elements shown in the figures may be enlarged or resized to facilitate recognition and discussion.

FIGS. 9A-9D illustrate exemplary functional diagrams of various configurations of the Bz' component generator of FIG. 8A according to principles described herein.

DETAILED DESCRIPTION

Magnetic field measurement systems for use in MEG and/or other applications are described herein. For example, an exemplary magnetic field measurement system includes a wearable sensor unit and a single controller. The wearable sensor unit includes a plurality of magnetometers and a magnetic field generator configured to generate a compensation magnetic field configured to actively shield the magnetometers from ambient background magnetic fields. The controller is configured to interface with the magnetometers and the magnetic field generator. For example, the controller may be configured to direct the magnetometers to detect magnetic fields generated within a user (e.g., within a brain of the user) wearing the wearable sensor unit, control various operating parameters of the magnetometers, and measure signals output by the magnetometers. The controller may be further configured to direct the magnetic field generator to generate the compensation magnetic field that actively shields the magnetometers from ambient background magnetic fields, control various operating parameters of the magnetic field generator, and measure various signals output by the magnetic field generator. These and other manners in which the controller may interface with the magnetometers and the magnetic field generator are described herein.

Advantageously, the controller uses a single common clock signal to communicate with the magnetometers and the magnetic field generator of the wearable sensor unit described herein. In this manner, the controller may ensure that communication with the magnetometers and the magnetic field generator is synchronized, thereby reducing or eliminating crosstalk between signals transmitted between the controller and the wearable sensor unit. Moreover, use of a single controller (and therefore a common clock signal) may result in more efficient and reliable communication between the controller and the wearable sensor unit compared to conventional configurations, less latency compared to conventional configurations, increased mobility of the wearable sensor unit compared to conventional configurations, and/or other benefits that will be made apparent herein.

Figure 1:
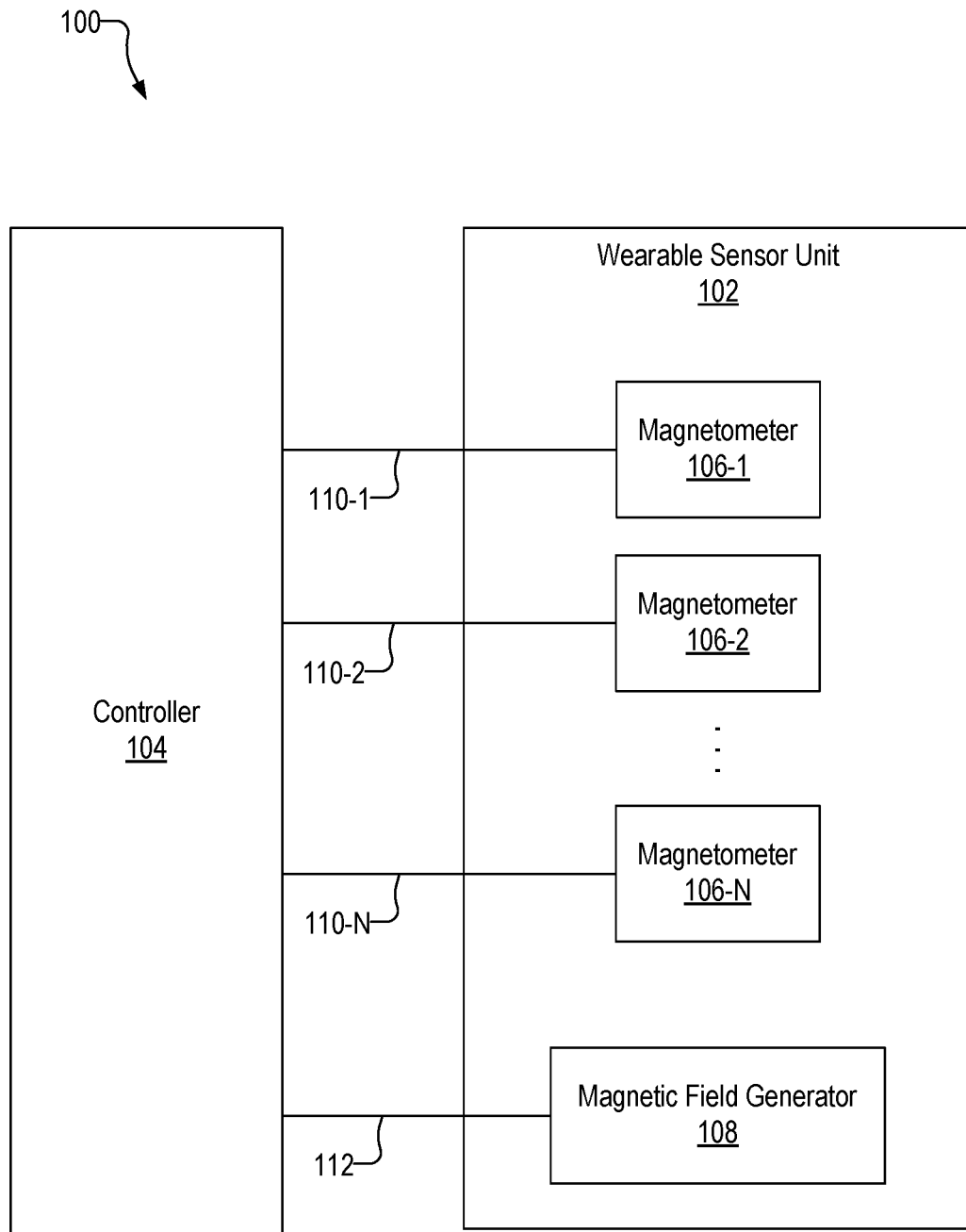
FIG. 1 illustrates an exemplary magnetic field measurement system according to principles described herein.

FIG. 1 shows an exemplary magnetic field measurement system 100 ("system 100"). As shown, system 100 includes a wearable sensor unit 102 and a controller 104. Wearable sensor unit 102 includes a plurality of magnetometers 106-1 through 106-N (collectively "magnetometers 106") and a magnetic field generator 108. Wearable sensor unit 102 may include additional components (e.g., one or more magnetic field sensors, position sensors, orientation sensors, accelerometers, image recorders, detectors, etc.) as may serve a particular implementation. System 100 may be used in MEG and/or any other application that measures relatively weak magnetic fields.

Wearable sensor unit 102 is configured to be worn by a user (e.g., on a head of the user). In some examples, wearable sensor unit 102 is portable. In other words, wearable sensor unit 102 may be small and light enough to be easily carried by a user and/or worn by the user while the user moves around and/or otherwise performs daily activities.

Any suitable number of magnetometers 106 may be included in wearable sensor unit 102. For example, wearable sensor unit 102 may include an array of nine, sixteen, twenty-five, or any other suitable plurality of magnetometers 106 as may serve a particular implementation.

Magnetometers 106 may each be implemented by any suitable combination of components configured to be sensitive enough to detect a relatively weak magnetic field (e.g., magnetic fields that come from the brain). For example, each magnetometer may include a light source, a vapor cell such as an alkali metal vapor cell (the terms "cell", "gas cell", "vapor cell", and "vapor gas cell" are used interchangeably herein), a heater for the vapor cell, and a photodetector (e.g., a signal photodiode). Examples of suitable light sources include, but are not limited to, a diode laser (such as a vertical-cavity surface-emitting laser (VCSEL), distributed Bragg reflector laser (DBR), or distributed feedback laser (DFB)), light-emitting diode (LED), lamp, or any other suitable light source. In some embodiments, the light source may include two light sources: a pump light source and a probe light source. These magnetometer components, and manners in which they operate to detect magnetic fields, are described in more detail herein, as well as in in co-pending U.S. patent application Ser. No. 16/457,655, filed Jun. 28, 2019, which application is incorporated by reference herein in its entirety.

Magnetic field generator 108 may be implemented by one or more components configured to generate one or more compensation magnetic fields that actively shield magnetometers 106 (including respective vapor cells) from ambient background magnetic fields (e.g., the Earth's magnetic field, magnetic fields generated by nearby magnetic objects such as passing vehicles, electrical devices and/or other field generators within an environment of magnetometers 106, and/or magnetic fields generated by other external sources). For example, magnetic field generator 108 may be configured to generate compensation magnetic fields in the Z direction, X direction, and/or Y direction (all directions are with respect to one or more planes within which the magnetic field generator 108 is located). The compensation magnetic fields are configured to cancel out, or substantially reduce, ambient background magnetic fields in a magnetic field sensing region with minimal spatial variability. As used herein, magnetic fields generated by magnetic field generator 108 in the Z direction are referred to as a Bz' component of the compensation magnetic field, magnetic fields generated by magnetic field generator 108 in the X direction are referred to as a Bx' component of the compensation magnetic field, and magnetic fields generated by magnetic field generator 108 in the Y direction are referred to as a By' component of the compensation magnetic field. Specific implementations of magnetic field generator 108 are described in more detail herein.

Controller 104 is configured to interface with (e.g., control an operation of, receive signals from, etc.) magnetometers 106 and the magnetic field generator 108. Controller 104 may also interface with other components that may be included in wearable sensor unit 102.

In some examples, controller 104 is referred to herein as a "single" controller 104. This means that only one controller is used to interface with all of the components of wearable sensor unit 102. For example, controller 104 is the only controller that interfaces with magnetometers 106 and magnetic field generator 108. This is in contrast to conventional configurations in which discrete magnetometers each have their own discrete controller associated therewith. It will be recognized, however, that any number of controllers may interface with components of magnetic field measurement system 100 as may suit a particular implementation.

As shown, controller 104 may be communicatively coupled to each of magnetometers 106 and magnetic field generator 108. For example, FIG. 1 shows that controller 104 is communicatively coupled to magnetometer 106-1 by way of communication link 110-1, to magnetometer 106-2 by way of communication link 110-2, to magnetometer 106-N by way of communication link 110-N, and to magnetic field generator 108 by way of communication link 112. In this configuration, controller 104 may interface with magnetometers 106 by way of communication links 110-1 through 110-N (collectively "communication links 110") and with magnetic field generator 108 by way of communication link 112.

Communication links 110 and communication link 112 may be implemented by any suitable wired connection as may serve a particular implementation. For example, communication links 110 may be implemented by one or more twisted pair cables while communication link 112 may be implemented by one or more coaxial cables. Advantages of such an implementation are described in more detail herein. Other communication links between controller 104 and wearable sensor unit 102 may additionally be included to facilitate control of and/or communication with other components included in wearable sensor unit 102.

Controller 104 may be implemented in any suitable manner. For example, controller 104 may be implemented by a field-programmable gate array (FPGA), an application specific integrated circuit (ASIC), a digital signal processor (DSP), a microcontroller, and/or other suitable circuit together with various control circuitry.

In some examples, controller 104 is implemented on one or more printed circuit boards (PCBs) included in a single housing. In cases where controller 104 is implemented on a PCB, the PCB may include various connection interfaces configured to facilitate communication links 110 and 112. For example, the PCB may include one or more twisted pair cable connection interfaces to which one or more twisted pair cables may be connected (e.g., plugged into) and/or one or more coaxial cable connection interfaces to which one or more coaxial cables may be connected (e.g., plugged into).

Figure 2:
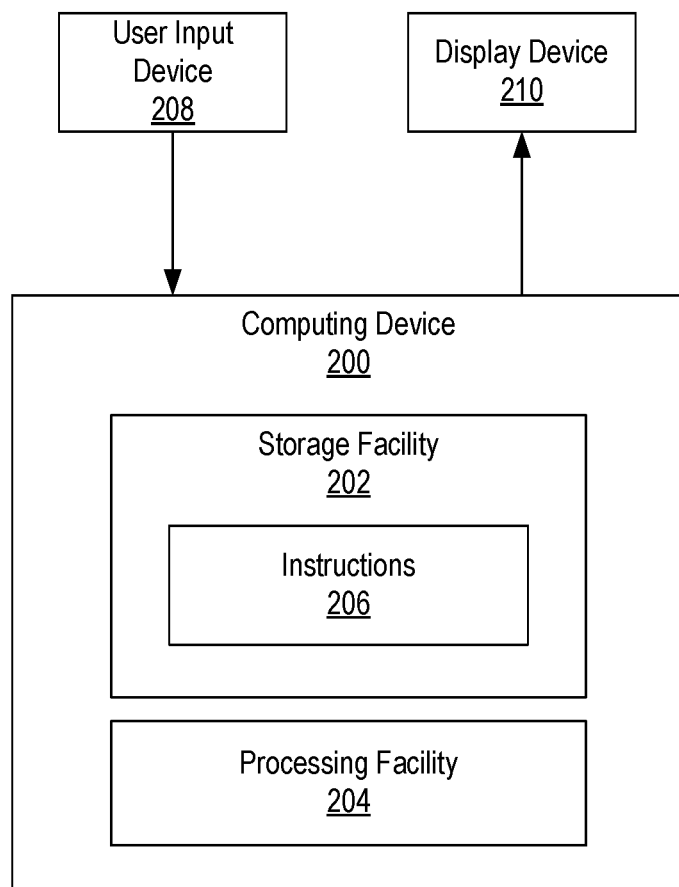
FIG. 2 illustrates an exemplary computing device that may implement a controller of the magnetic field measurement system of FIG. 1 according to principles described herein.

In some examples, controller 104 may be implemented by or within a computing device. FIG. 2 illustrates an exemplary computing device 200 that may implement controller 104. Computing device 200 may be implemented by a desktop computer, a mobile device, a server, and/or any other single computing device having a single housing for components of the computing device.

As shown, computing device 200 may include, without limitation, a storage facility 202 and a processing facility 204 selectively and communicatively coupled to one another. Facilities 202 and 204 may each include or be implemented by hardware and/or software components (e.g., processors, memories, communication interfaces, instructions stored in memory for execution by the processors, etc.).

Storage facility 202 may maintain (e.g., store) executable data used by processing facility 204 to perform one or more of the operations described herein. For example, storage facility 202 may store instructions 206 that may be executed by processing facility 204 to perform one or more of the operations described herein. Instructions 206 may be implemented by any suitable application, software, code, and/or other executable data instance. Storage facility 202 may also maintain any data received, generated, managed, used, and/or transmitted by processing facility 204.

Processing facility 204 may be configured to perform (e.g., execute instructions 206 stored in storage facility 202 to perform) various operations described herein.

As shown, computing device 200 may be communicatively coupled to a user input device 208 and to a display device 210. User input device 208 may be implemented by a keyboard, a mouse, a touch screen, a track ball, a joystick, a voice recognition system, and/or any other component configured to facilitate providing of user input to computing device 200. Display device 210 may be implemented by a monitor, a screen, a printer, and/or any other device configured to display output provided by computing device 200. In some examples, display device 210 is integrated into a single unit with computing device 200.

Figure 3:
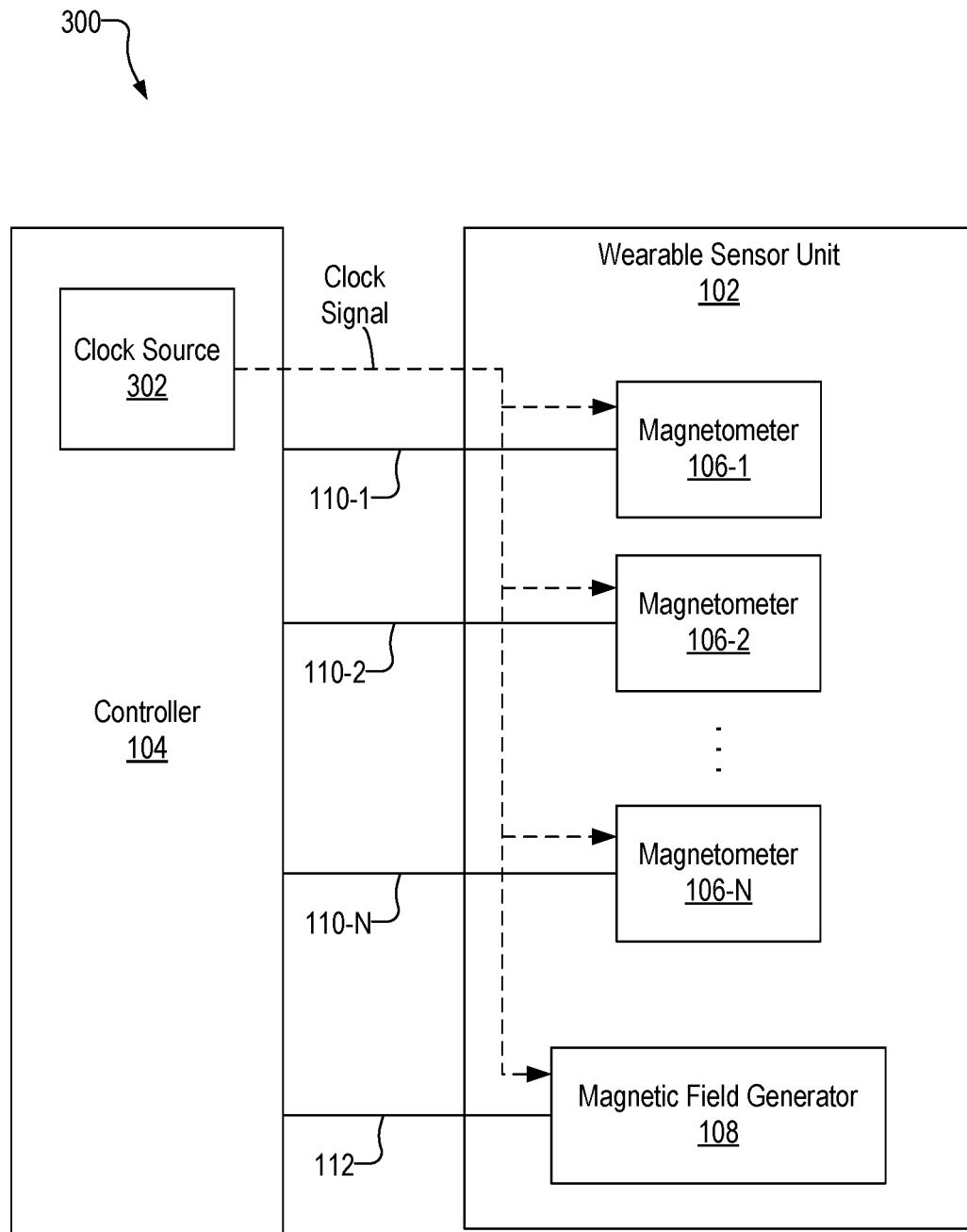
FIG. 3 illustrates an exemplary configuration of the magnetic field measurement system of FIG. 1 according to principles described herein.

FIG. 3 illustrates an exemplary configuration 300 of system 100 in which controller 104 includes a clock source 302 configured to generate a common clock signal used by controller 104 to interface with the components of wearable sensor unit 102. For example, controller 104 may use the common clock signal to drive or otherwise control various components within each of magnetometers 106 and drive or otherwise control magnetic field generator 108. Use of the common clock signal to interface with magnetometers 106 and magnetic field generator 108 is illustrated in FIG. 3 (and various other figures) by dashed lines interconnecting clock source 302 and magnetometers 106 and magnetic field generator 108.

By using a single common clock signal (as opposed to an array of independent clocks as done in conventional configurations), controller 104 may ensure that communication with magnetometers 106 and magnetic field generator 108 (and, in some implementations, other components within wearable sensor unit 102) is synchronized, thereby reducing or eliminating crosstalk between signals transmitted between controller 104 and wearable sensor unit 102, as well as providing other benefits described herein.

In some implementations, as illustrated in FIGS. 1 and 3, controller 104 is remote from (i.e., not included within) wearable sensor unit 102. For example, in these implementations, controller 104 may be implemented by or included in a standalone computing device not configured to be worn by a user (e.g., computing device 200). The computing device may interface with one or more user input devices (e.g., user input device 208) and one or more display devices (e.g., display device 210). In this manner, a user may provide user input by way of the computing device to control, program, configure, and/or otherwise interface with controller 104. The computing device may present information (e.g., output data generated by wearable sensor unit 102) by way of the one or more display devices.

Figure 4:
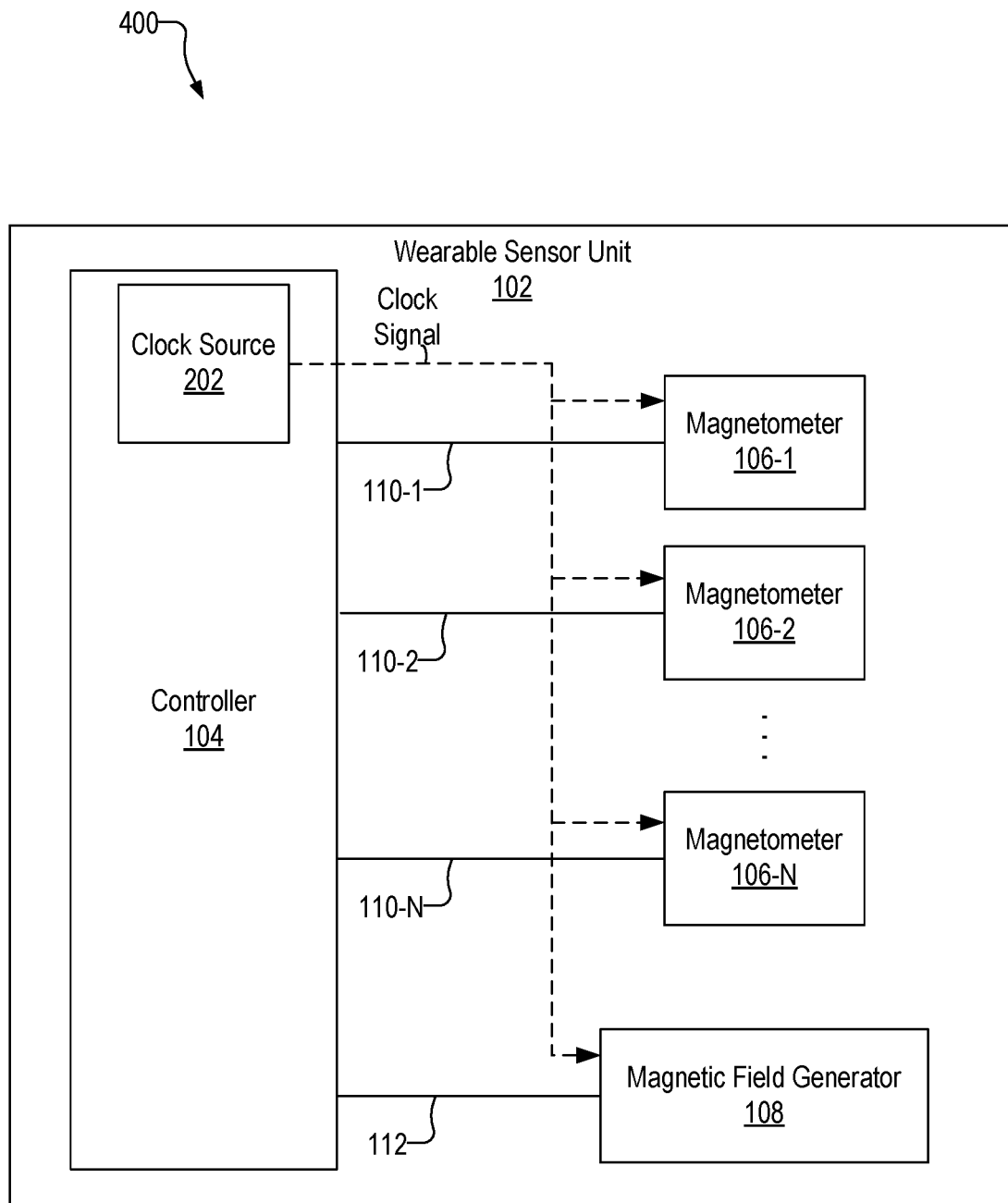
FIG. 4 illustrates another exemplary configuration of the magnetic field measurement system of FIG. 1 according to principles described herein.

FIG. 4 shows an alternative configuration 400 in which controller 104 is included within wearable sensor unit 102. Configuration 400 may allow a user of wearable sensor unit 102 to travel or otherwise move freely while still wearing wearable sensor unit 102 without having to ensure that wearable sensor unit 102 is connected to a separate non-wearable controller.

In configuration 400, controller 104 may include one or more interfaces (e.g., wired or wireless interfaces) configured to facilitate communication between controller 104 and an external computing device. In this manner, a user may use the external computing device to control, program, configure, or otherwise interface with controller 104. Wearable sensor unit 102 may further include a power supply (not shown) configured to provide operating power to controller 104 and various other components included in wearable sensor unit 102.

As another exemplary configuration, controller 104 may be included in a wearable sensor unit other than wearable sensor unit 102. For example, a magnetic field measurement system may include a first wearable sensor unit and a second wearable sensor unit. A controller included in the first wearable sensor unit may be communicatively coupled to the second wearable sensor unit and configured to control both the first and second wearable sensor units. To this end, the first and second wearable sensor units may be communicatively coupled by way of any suitable communication link.

As another exemplary configuration, controller 104 may be included in a wearable device configured to be worn by a user and separate from wearable sensor unit 102. For example, controller 104 may be included in a wearable device (e.g., a device that may be worn on the head, on the back (e.g., in a backpack), and/or on the waist (e.g., in a unit configured to clip or strap to a belt of the user) and communicatively coupled to wearable sensor unit 102 by way of any suitable communication link. Examples of this are described herein.

Figure 5:
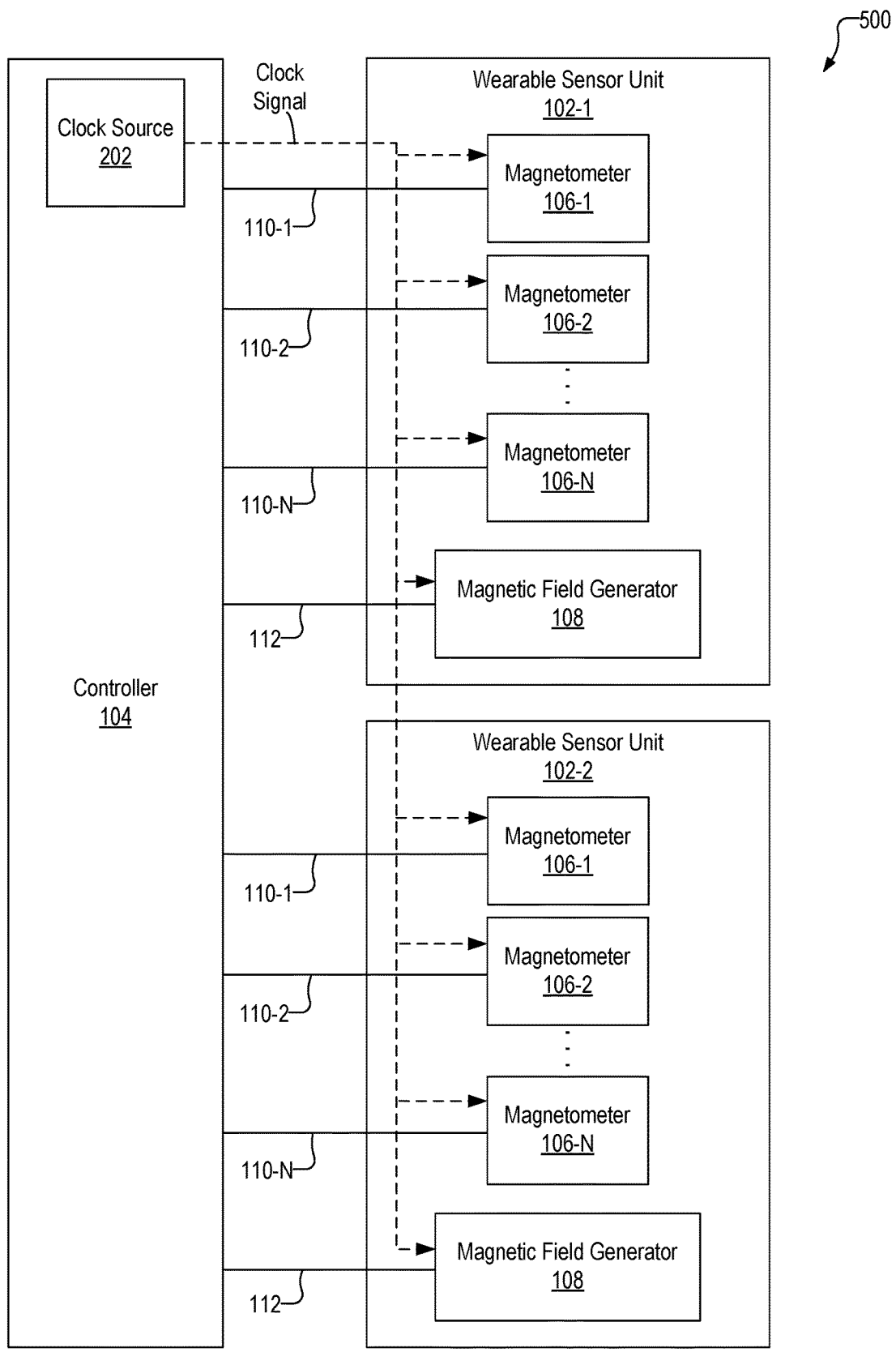
FIG. 5 illustrates yet another exemplary configuration of the magnetic field measurement system of FIG. 1 according to principles described herein.

FIG. 5 shows an exemplary configuration 500 in which controller 104 is configured to concurrently interface with multiple wearable sensor units (e.g., multiple wearable sensor units configured to be worn concurrently by a user). For example, as shown, controller 104 is communicatively coupled to wearable sensor unit 102-1 and wearable sensor unit 102-2 (collectively "wearable sensor units 102"). As shown, both wearable sensor units 102 include a plurality of magnetometers 106 and a magnetic field generator 108. As shown, controller 104 may interface with magnetometers 106 by way of communication links 110 and with magnetic field generators 108 by way of communication links 112.

As shown, the common clock signal output by clock source 202 is configured to be used by controller 104 to control or otherwise interface with all of the components of both wearable sensor units 102. In this manner, operation of and data output by wearable sensor units 102 may be synchronized.

In the examples described above, controller 104 of system 100 may control or interface with various components of one or more wearable sensor units 102 to measure biological or other magnetic fields. As explained above, a wearable sensor unit 102 may include, in some examples, one or more magnetometers 106 and a magnetic field generator 108. These components will now be described.

Magnetometers 106 may be any suitable magnetometers, such as but not limited to optically pumped magnetometers (OPMs), nitrogen vacancy (NV) diamond sensors, and magnetoresistance sensors. OPMs may operate in a vector mode and/or a scalar mode. In some examples, vector mode OPMs may operate at zero-fields and may utilize a spin exchange relaxation free (SERF) mode to reach femto-Tesla sensitivities.

Figure 6:
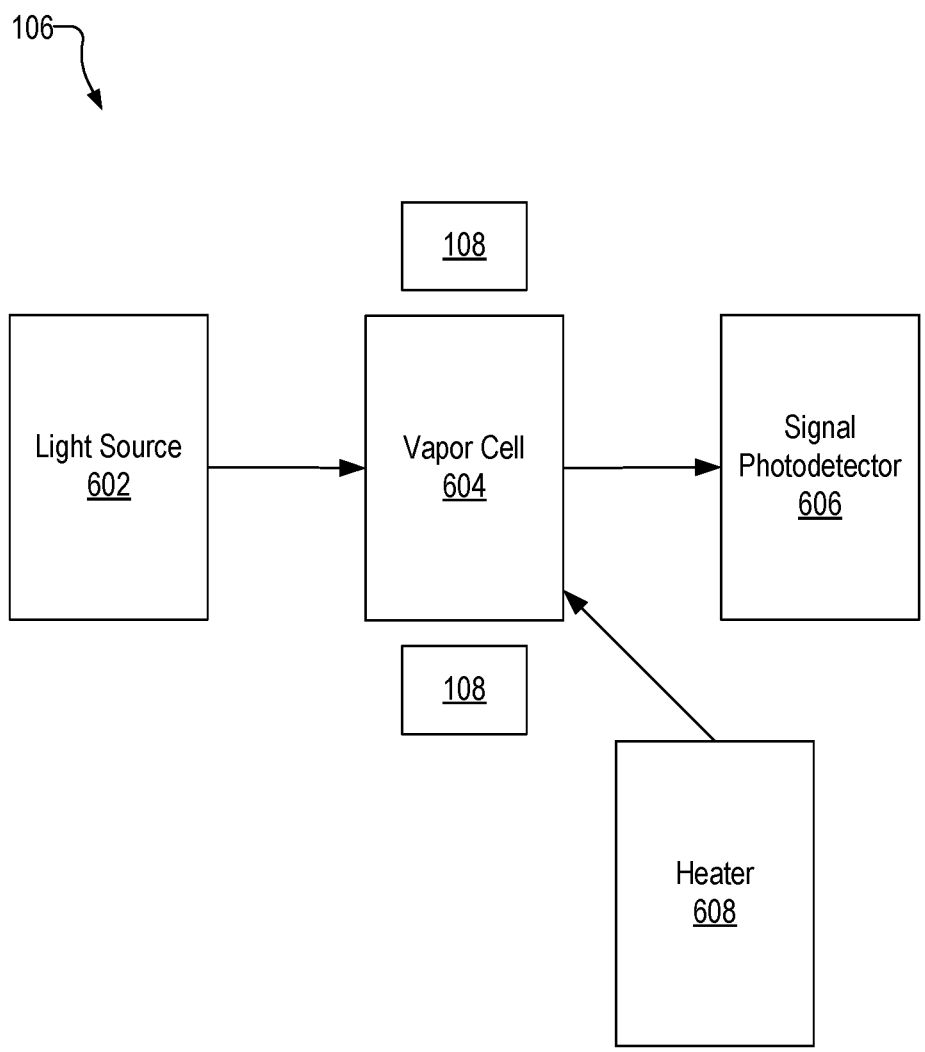
FIG. 6 illustrates a block diagram of an exemplary magnetometer according to principles described herein.

FIG. 6 illustrates a block diagram of an exemplary magnetometer 106. As shown, magnetometer 106 is an OPM. Magnetometer 106 includes a light source 602, a vapor cell 604, a signal photodetector 606, and a heater 608. In addition, the magnetic field generator 108 can be positioned around the vapor cell 604. Magnetometer 106 may include additional or alternative components as may suit a particular implementation, such as optics (e.g., lenses, waveplates, collimators, polarizers, and/or objects with reflective surfaces for beam shaping and polarization control and for directing light from light source 602 to vapor cell 604 and to signal photodetector 606) and/or any other suitable components.

Light source 602 is configured to generate and emit light (e.g., laser light) to optically pump alkali metal atoms in vapor cell 604 and to probe vapor cell 604. Examples of suitable light source devices include, but are not limited to, a diode laser (e.g., a vertical-cavity surface-emitting laser (VCSEL), a distributed Bragg reflector laser (DBR), a distributed feedback laser (DFB), etc.), a light-emitting diode (LED), a lamp, or any other suitable light source.

Vapor cell 604 contains an alkali metal vapor (e.g., rubidium in natural abundance, isotopically enriched rubidium, potassium, or cesium, or any other suitable alkali metal such as lithium, sodium, potassium, rubidium, cesium, or francium) and, optionally, a quenching gas (e.g., nitrogen) and/or a buffer gas (e.g., nitrogen, helium, neon, or argon). It will be recognized that vapor cell 604 can contain additional or other gases or vapors as may suit a particular implementation. Heater 608 is configured to heat vapor cell 604.

Signal photodetector 606 is configured to detect and measure optical properties (e.g., amplitude, phase, and/or polarization) of light emitted by light source 602 that has passed through vapor cell 604. Examples of suitable signal photodetectors include, but are not limited to, a photodiode, a charge coupled device (CCD) array, a CMOS array, a camera, a photodiode array, a single photon avalanche diode (SPAD) array, an avalanche photodiode (APD) array, and/or any other suitable optical sensor array that can measure a change in transmitted light at the optical wavelengths of interest.

Operation of magnetometer 106 will now be described. Light emitted by light source 602 enters vapor cell 604 where it induces a transparent steady state in the alkali metal vapor. In the transparent steady state the light is allowed to pass through the vapor cell 604 with minimal absorption by the alkali metal vapor and, hence, maximal detection by signal photodetector 606. Magnetic fields generated from a target source (e.g., magnetic fields generated by a user's brain) cause the transparency of the alkali metal vapor to decrease so that less light is detected at signal photodetector 606. The change in light detected at signal photodetector 606 is correlated to magnetic fields generated by the target source.

However, ambient background magnetic fields may interfere with the measurement by magnetometer 106 of magnetic fields generated by a target source. As used herein, the term "ambient background magnetic fields" refers to a magnetic field or magnetic fields associated with (e.g., generated by) sources other than system 100 and the sources of interest (e.g., magnetic fields associated with neural signals from a user's brain). The ambient background magnetic fields can include, for example, the Earth's magnetic field as well as magnetic fields from magnets, electromagnets, electrical devices, and other signal or field generators in the environment other than magnetic field generator 108 that is part of system 100.

Figure 7:
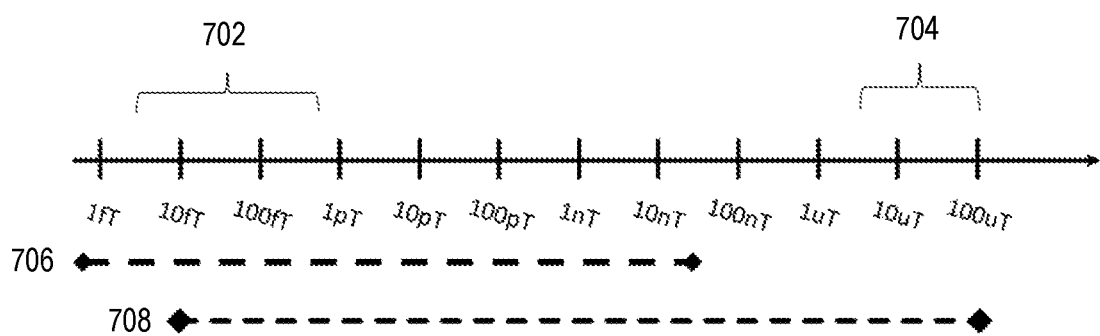
FIG. 7 shows a magnetic spectrum in magnetic field strength on a logarithmic scale according to principles described herein.

FIG. 7 shows the magnetic spectrum from 1 fT to 100 µT in magnetic field strength on a logarithmic scale. The magnitude of magnetic fields generated by the human brain are indicated by range 702 and the magnitude of ambient background magnetic fields, including the Earth's magnetic field, by range 704. The strength of the Earth's magnetic field covers a range as it depends on the position on the Earth as well as the materials of the surrounding environment where the magnetic field is measured. Range 706 indicates the approximate measurement range of a magnetometer (e.g., an OPM) operating in the SERF mode (e.g., a SERF magnetometer) and range 708 indicates the approximate measurement range of a magnetometer operating in the scalar mode (e.g., a scalar magnetometer.) Typically, a SERF magnetometer is more sensitive than a scalar magnetometer, but many conventional SERF magnetometers typically only operate up to about 0 to 200 nT while the scalar magnetometer starts in the 10 to 100 fT range but extends above 10 to 100 µT. At very high magnetic fields the scalar magnetometer typically becomes nonlinear due to a nonlinear Zeeman splitting of atomic energy levels.

As can be seen from FIG. 7, SERF magnetometers have high sensitivity but, conventionally, cannot function in a magnetic field higher than about 50 nT, which is approximately $\frac{1}{1000}$ of the magnetic field strength generated by the Earth. For a SERF magnetometer to accurately measure biological and other weak signals, the strength of ambient background magnetic fields, including the Earth's magnetic field, need to be canceled or reduced to at least less than about 10-20 nT. Accordingly, wearable sensor unit 102 includes one or more active magnetic field shields (e.g., magnetic field generator 108) and, optionally, one or more passive magnetic field shields. An active magnetic field shield generates, for example, an equal and opposite magnetic vector that cancels out, or substantially reduces, the ambient background magnetic fields. A passive magnetic field shield redirects magnetic fields away from magnetic field sensors (e.g., away from magnetometers 106). Exemplary passive magnetic field shields are described in more detail in U.S. patent application Ser. No. 16/457,655, which is incorporated herein by reference in its entirety.

Magnetic field generator 108 is configured to generate a compensation magnetic field configured to actively shield a magnetic field sensing region from ambient background magnetic fields. An ambient background magnetic field B is a vector magnetic field that has magnitude and direction at each point in space. Using the Cartesian coordinate system, ambient background magnetic field B can be expressed as:

$$B = i \cdot Bx + j \cdot By + k \cdot Bz$$

where Bx, By and Bz are the Cartesian components of the ambient background magnetic field and i, j, and k are unit vectors along the x-, y-, and z-axes. The compensation magnetic field B' generated by magnetic field generator 108 is expressed as:

$$B' = i \cdot Bx' + j \cdot By' + k \cdot Bz'$$

where Bx', By' and Bz' are the Cartesian components of the compensation magnetic field and i, j, and k are unit vectors along the x-, y-, and z-axes. In some examples, controller 104 may determine the compensation magnetic field to be generated by magnetic field generator 108. For example, controller 104 may interface with one or more magnetic field sensors included in wearable sensor unit 102 to measure the ambient background magnetic field B. Controller 104 may determine the compensation magnetic field B' (e.g., determine the Bx' component, the By' component, and/or the Bz' component of compensation magnetic field B') based on the measured ambient background magnetic field B. Exemplary methods for determining a compensation magnetic field are described in detail in U.S. patent application Ser. No. 16/213,980, which is incorporated by reference herein in its entirety. Controller 104 may then drive magnetic field generator 108 to generate the compensation magnetic field.

The compensation magnetic field generated by magnetic field generator 108 may actively shield the magnetic field sensing region by canceling or substantially reducing (e.g., by at least 80%, 85%, 90%, 95%, or 99%, etc.) ambient background magnetic fields in one, two, or three dimensions. For example, magnetic field generator 108 may include one or more of a Bz' component generator, a Bx' component generator, and/or a By' component generator configured to cancel or substantially reduce ambient background magnetic fields along a z-axis, an x-axis, and/or a y-axis associated with magnetic field generator 108.

Figure 8A:
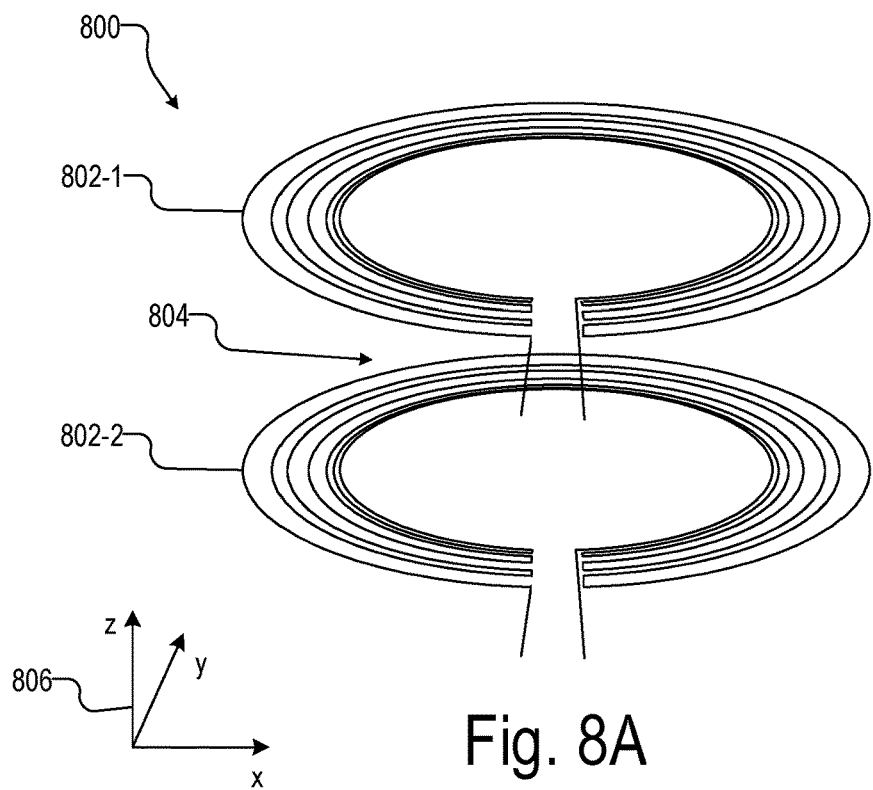
FIG. 8A illustrates an exemplary Bz' component generator of a magnetic field generator according to principles described herein.

FIG. 8A illustrates an exemplary Bz' component generator 800 of magnetic field generator 108. As shown, Bz' component generator 800 includes a plurality of conductive windings 802 arranged in opposing parallel planes. For example, Bz' component generator 800 includes a first conductive winding 802-1 arranged in a first plane and a second conductive winding 802-2 arranged in a second plane that is substantially parallel to the first plane. A magnetic field sensing region 804 is located between conductive winding 802-1 and conductive winding 802-2. Magnetic field sensing region 804 is a region where one or more magnetometers 106 (e.g., vapor cells 604) may be located.

Bz' component generator 800 is configured to actively shield magnetic field sensing region 804 (and hence magnetometers 106) from ambient background magnetic fields along a z-axis, such as by substantially reducing or canceling a Bz component of ambient background magnetic fields at magnetic field sensing region 804. Legend 806 indicates an orientation of x-, y-, and z-axes, which have been arbitrarily assigned relative to components of magnetic field generator 108. As indicated by legend 806, the z-axis is a direction normal to the first plane and the second plane, the x-axis is a direction orthogonal to the z-axis and parallel to the first plane and the second plane, and the y-axis is a direction orthogonal to the z-axis and the x-axis and parallel to the first plane and the second plane.

Figure 8B:
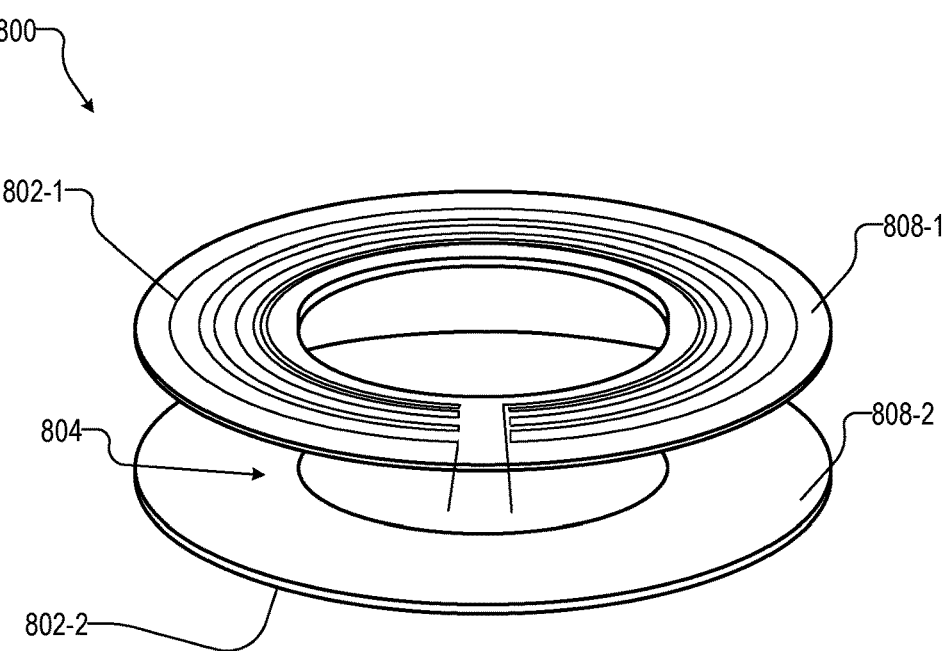
FIG. 8B illustrates an exemplary configuration of the Bz' component generator of FIG. 8A.

Each conductive winding 802 comprises one or more coils, half coils, loops, and/or turns of conductive wiring forming a continuous electrical path arranged substantially in a single plane. Conductive windings 802 may be formed of any suitable conductor of electrical current, such as metallic conductors (e.g., copper, silver, and/or gold) and non-metallic conductors (e.g., carbon). Each conductive winding 802 may be arranged in a plane in any suitable way. In some examples, each conductive winding 802 is arranged (e.g., etched, printed, soldered, deposited, or otherwise attached) on a planar substrate. The planar substrate may be formed of any suitable material, such as but not limited to alumina, ceramics, glass, and/or PCB material. FIG. 8B illustrates an exemplary configuration of Bz' component generator 800 in which conductive winding 802-1 is arranged on an upper surface of a first PCB 808-1 and conductive winding 802-2 (not shown) is arranged on a bottom surface of a second PCB 808-2. Second PCB 808-2 is substantially parallel to first PCB 808-1. While PCBs 808 are shown to be round, they may be any other shape as may suit a particular implementation. PCBs 808 may be supported and maintained in substantially parallel alignment in any suitable way, such as by one or more posts, screws, or other suitable supporting structures.

FIGS. 9A-9D show exemplary functional diagrams of Bz' component generator 800 and illustrate various configurations in which conductive windings 802 may be arranged in parallel planes. In FIGS. 9A-9D conductive windings 802 are shown to have a vertical (z-direction) dimension above substrates 902 on which they are arranged. However, this is only for illustration purposes, as conductive windings 802 may be implemented by traces on substrates 902 or otherwise be embedded within substrates 902.

FIG. 9A illustrates an exemplary configuration in which Bz' component generator 800 includes a single substrate 902. Conductive winding 802-1 is arranged on a first surface 904-1 of substrate 902 and conductive winding 802-2 is arranged on a second surface 904-2 of substrate 902. First surface 904-1 corresponds to the first plane and second surface 904-2 corresponds to the second plane. Substrate 902 has a hole 906 aligned with center openings of conductive windings 802. Magnetic field sensing region 804 is located in hole 906.

FIG. 9B illustrates another exemplary configuration in which Bz' component generator 800 includes two substrates 902 (e.g., first substrate 902-1 and second substrate 902-2). Conductive winding 802-1 is arranged on an outer surface 904-1 of first substrate 902-1 (e.g., a surface facing away from magnetic field sensing region 804) and conductive winding 802-2 is arranged on an outer surface 904-2 of second substrate 902-2 (e.g., a surface facing away from magnetic field sensing region 804). Outer surface 904-1 corresponds to the first plane and outer surface 904-2 corresponds to the second plane.

FIG. 9C illustrates another exemplary configuration of Bz' component generator 800. FIG. 9C is the same as FIG. 9B except that conductive winding 802-1 is arranged on an inner surface 904-3 of first substrate 902-1 (e.g., a surface facing magnetic field sensing region 804) and conductive winding 802-2 is arranged on an inner surface 904-4 of second substrate 902-2 (e.g., a surface facing magnetic field sensing region 804). Inner surface 904-3 corresponds to the first plane and inner surface 904-4 corresponds to the second plane.

FIG. 9D illustrates another exemplary configuration of Bz' component generator 800. FIG. 9D is the same as FIG. 9B except that conductive winding 802-1 is arranged on inner surface 904-3 of first substrate 902-1 (e.g., a surface facing magnetic field sensing region 804), while conductive winding 802-2 is arranged on outer surface 904-2 of second substrate 902-2 (e.g., a surface facing away from magnetic field sensing region 804). Inner surface 904-3 corresponds to the first plane and outer surface 904-2 corresponds to the second plane.

Figure 10:
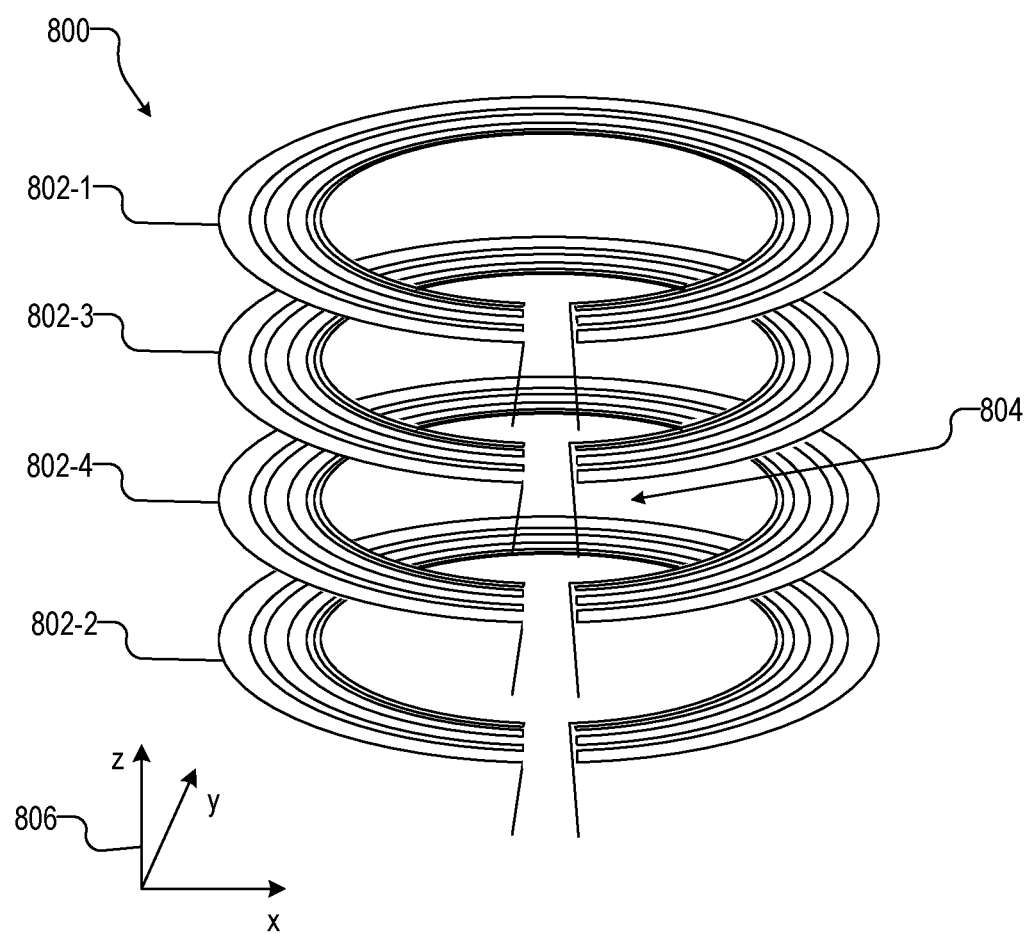
FIG. 10 illustrates another exemplary Bz' component generator of a magnetic field generator according to principles described herein.

In the foregoing examples, Bz' component generator 800 has two conductive windings. However, Bz' component generator 800 may have any other number of conductive windings as may suit a particular implementation, as illustrated in FIG. 10. FIG. 10 is the same as FIG. 8A except that the plurality of conductive windings 802 further includes a conductive winding 802-3 arranged in a third plane and a conductive winding 802-4 arranged in a fourth plane. The third plane and the fourth plane are substantially parallel to the first plane and the second plane. Magnetic field sensing region 804 is located between conductive windings 802-3 and 802-4. However, magnetic field sensing region 804 may be located in any other suitable location.

Figure 11A:
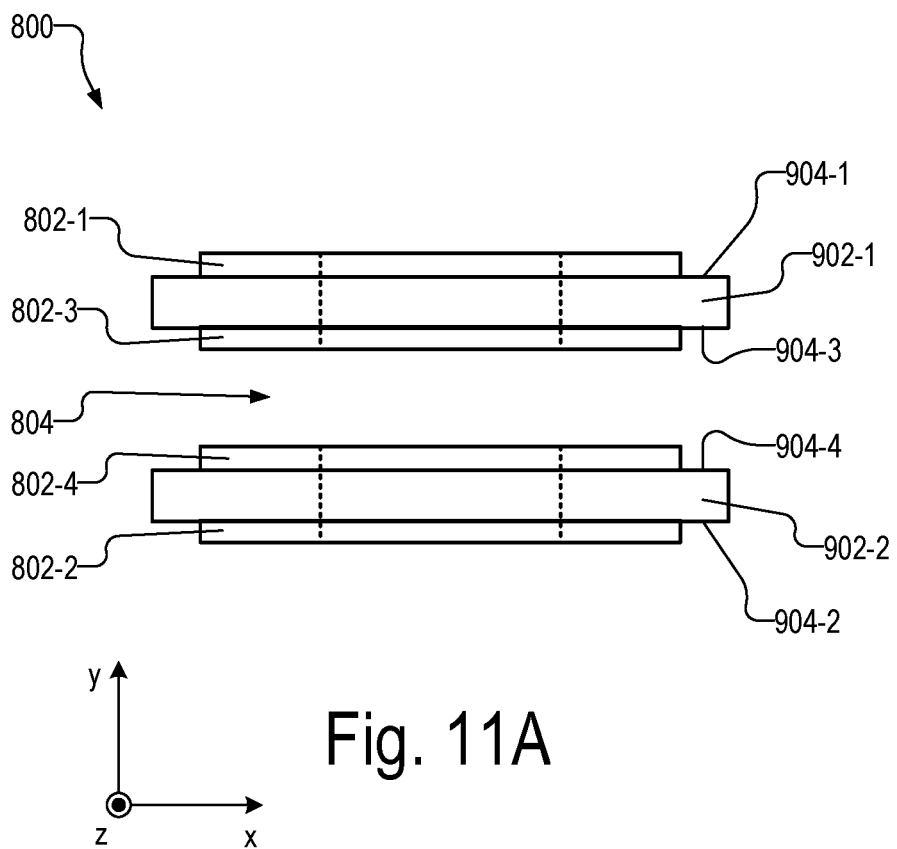
FIG. 11A illustrates a functional diagram of an exemplary configuration of the Bz' component generator of FIG. 10 according to principles described herein.
Figure 11B:
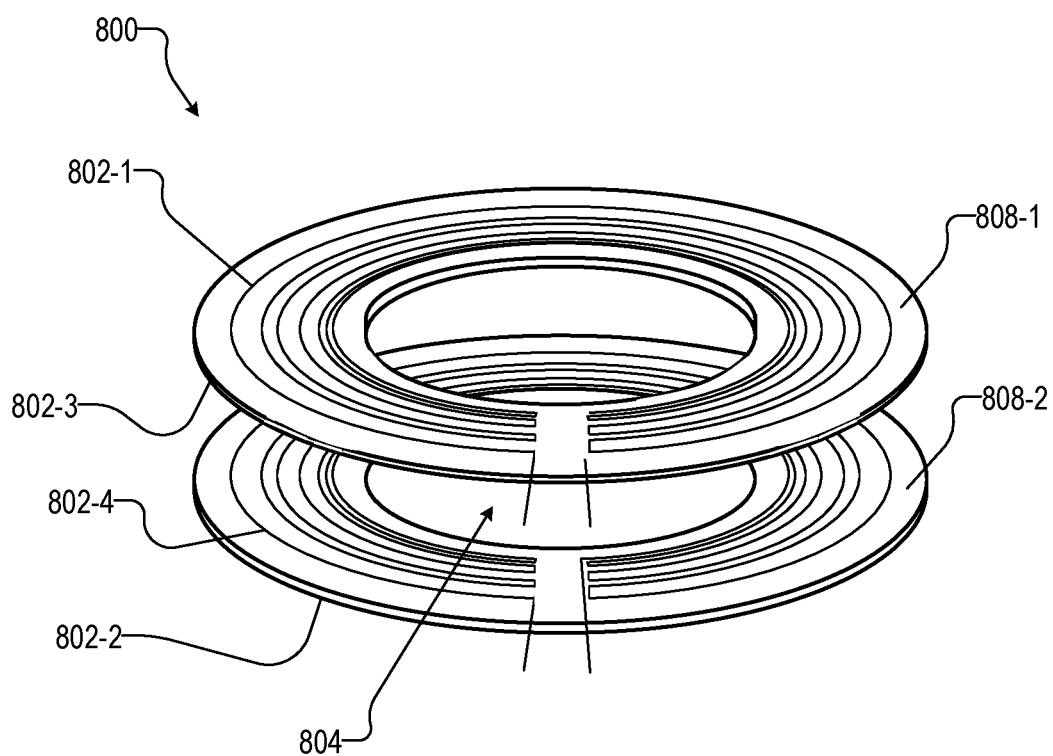
FIG. 11B illustrates an exemplary configuration of the Bz' component generator 800 of FIGS. 10 and 11A according to principles described herein.

Conductive windings 802-3 and 802-4 may be arranged on the third plane and the fourth plane in any manner described herein. FIG. 11A shows a functional diagram of another exemplary configuration of Bz' component generator 800. FIG. 11A is the same as FIG. 9B except that conductive winding 802-3 is arranged on inner surface 904-3 of first substrate 902-1 and conductive winding 802-4 is arranged on inner surface 904-4 of second substrate 902-2. Inner surface 904-3 corresponds to the third plane and inner surface 904-4 corresponds to the fourth plane. FIG. 11B illustrates an exemplary configuration of Bz' component generator 800 shown in FIGS. 10 and 11A. FIG. 11B is the same as FIG. 8B except that conductive winding 802-3 (not visible in FIG. 11B) is arranged on an inner surface of first PCB 808-1 (e.g., a surface facing magnetic field sensing region 804) and conductive winding 802-4 is arranged on an inner surface of second PCB 808-2 (e.g., a surface facing magnetic field sensing region 804).

The foregoing examples show conductive windings 802-1 through 802-4 arranged on two substrates (e.g., PCBs 808 or substrates 902). In other examples conductive windings 802-1 through 802-4 may be arranged on more than two substrates. For instance, each conductive winding 802 may each be arranged on a separate substrate. However, arranging multiple conductive windings 802 on a single substrate (e.g., on opposite surfaces of a substrate, as illustrated in FIGS. 11A and 11B) fixes the alignment of the conductive windings 802 relative to one another and thus prevents inadvertent misalignments.

In the examples described above, conductive windings 802 may have any winding pattern as may suit a particular implementation. As used herein, a winding pattern may refer to the path of conductive wiring, the spacing between adjacent wires, a width/thickness of wires, the number of loops or turns, the direction of current flow, and the like. In some examples the winding patterns of conductive windings 802 may be automatically generated by a magnetic field generator design system configured to optimize the winding patterns based on a set of inputs. An exemplary magnetic field generator design system will be described below in more detail. Generally, the winding patterns of conductive windings 802 are configured to generate a homogeneous magnetic field at the magnetic field sensing region. The winding patterns may be configured to generate a homogeneous magnetic field that is approximately 30% the size of conductive windings 802, as measured along the x- or y-direction.

In some examples, winding patterns of the plurality of conductive windings are substantially identical (e.g., mirror images of one another). For example, conductive winding 802-1 may be substantially identical to conductive winding 802-2. Additionally, conductive windings 802-3 and 802-4 may be substantially identical to each other and/or to conductive windings 802-1 and 802-2.

In some examples, conductive windings 802 may grouped into pairs (e.g., based on a drive current supplied, a location of conductive windings 802, etc.) such that conductive windings 802 within a particular pair have the same winding patterns, but different pairs of conductive windings 802 have different winding patterns. For instance, winding patterns of conductive windings 802-1 and 802-2 may be substantially identical, and winding patterns of conductive windings 802-3 and 802-4 may be substantially identical but different from the winding patterns of conductive windings 802-1 and 802-2.

In some examples, conductive windings 802 within a particular pair of conductive windings have different winding patterns. For instance, winding patterns of conductive windings 802-1 and 802-2 may be different from one another. This may be desirable when magnetic sensing region 804 is off-center in the z-direction (e.g., is closer to first substrate 902-1 or second substrate 902-2). Winding patterns of conductive windings 802-3 and 802-4 may be substantially identical or may also be different from one another.

Figure 12:
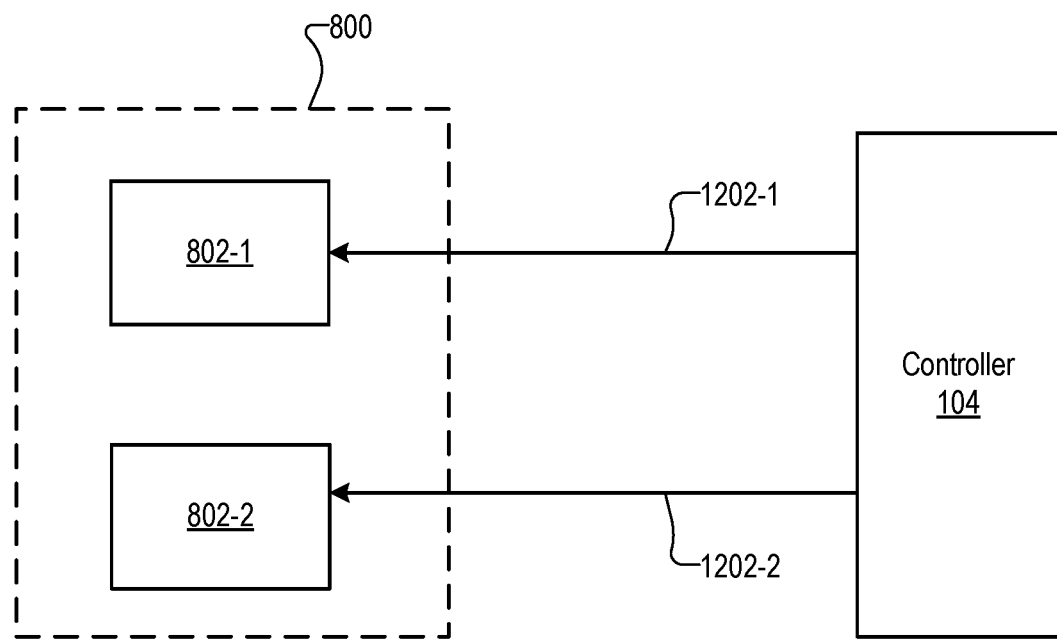
FIG. 12 illustrates an exemplary functional diagram for driving a Bz' component generator according to principles described herein.

Controller 104 is configured is to drive conductive windings 802 by supplying one or more drive currents to conductive windings 802. FIG. 12 shows an exemplary functional diagram indicating how controller 104 may drive Bz' component generator 800. As shown, controller 104 may supply a first drive current 1202-1 to conductive winding 802-1 and supply a second drive current 1202-2 to conductive winding 802-2. Drive currents 1302 may be supplied, for example, by way of communication link 112.

Figure 13:
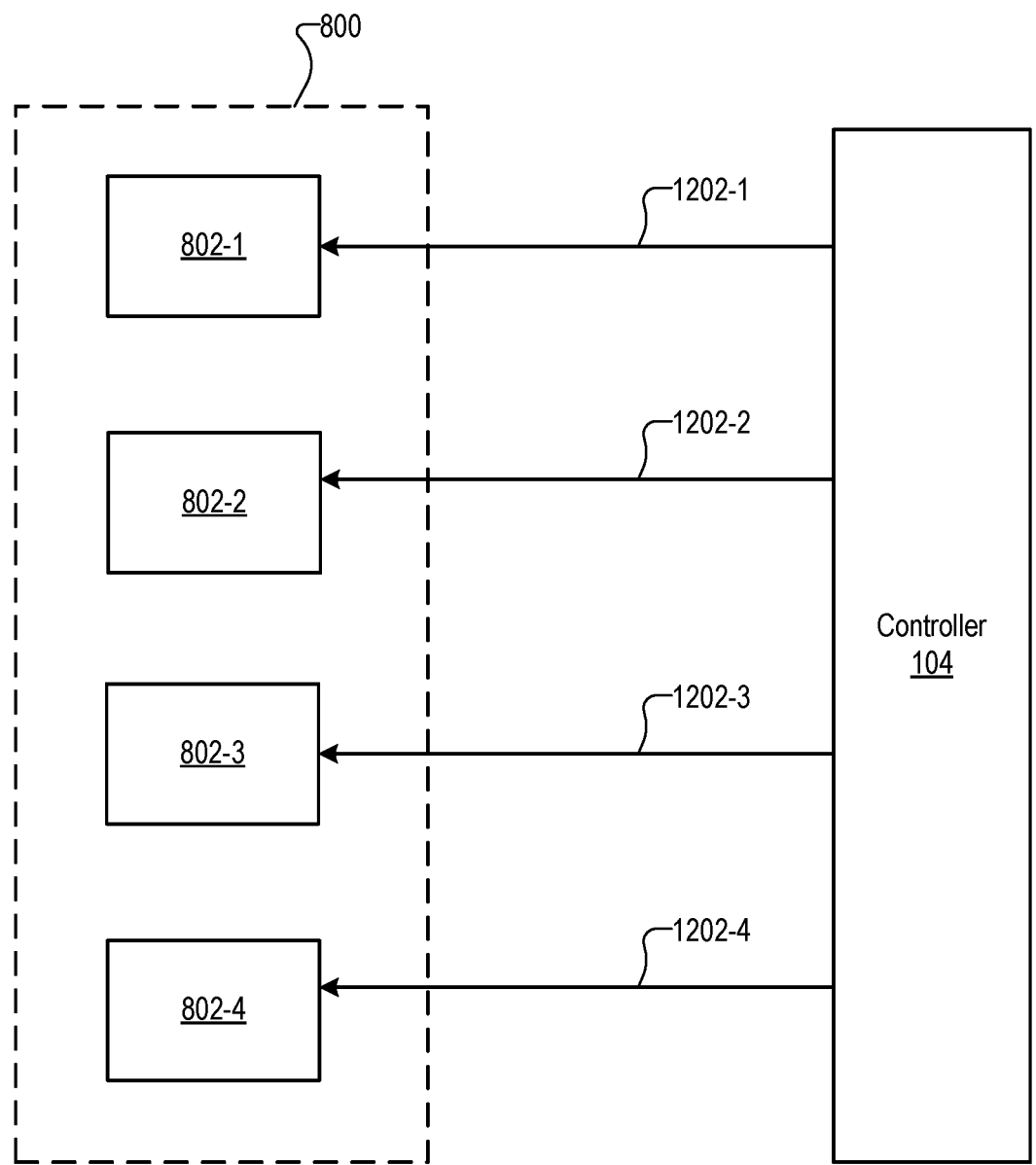
FIG. 13 illustrates another exemplary functional diagram for driving a Bz' component generator according to principles described herein.

FIG. 13 illustrates another exemplary schematic illustrating how controller 104 may drive Bz' component generator 800. FIG. 13 is the same as FIG. 12 except that Bz' component generator 800 further includes conductive windings 802-3 and 802-4. Accordingly, controller 104 is configured to supply a third drive current 1202-3 to conductive winding 802-3 and supply a fourth drive current 1202-4 to conductive winding 802-4. Drive currents 1202-3 and 1202-4 may be supplied by way of communication link 112.

Conductive windings 802 are configured to generate a Bz' component of a compensation magnetic field when conductive windings 802 are supplied with drive currents 1202. The Bz' component of the compensation magnetic field is configured to actively shield magnetic field sensing region 804 from ambient background magnetic fields along the z-axis, such as by reducing or canceling a Bz component of ambient background magnetic fields. In some examples, the Bz' component of the compensation magnetic field is substantially equal and opposite to the Bz component of the ambient background magnetic fields.

Controller 104 may drive conductive windings 802 in any suitable way. For example, controller 104 may supply conductive windings 802 with the same drive current 1202. In other words, drive currents 1202 may all be the same current. In some examples controller 104 includes a single driver configured to supply all drive currents 1202 to conductive windings 802. In alternative examples, controller 104 includes a plurality of individual drivers each configured to supply a drive current 1202, but controller 104 controls the drivers to supply the same drive current to conductive windings 802. By driving conductive windings 802 such that drive currents 1202 are the same, conductive windings 802 generate a uniform magnetic field along the z-direction in magnetic field sensing region 804.

Alternatively to supplying conductive windings 802 with the same drive current, controller 104 may supply one or more of conductive windings 802 with a drive current that is different from drive currents supplied to other conductive windings 802. For example, drive current 1202-1 may be different from drive current 1202-2. Additionally or alternatively, drive current 1202-3 may be different from drive current 1202-4. When conductive windings 802-1 and 802-2 are driven with different drive currents, Bz' component generator 800 generates a gradient magnetic field (e.g., a dBz'/dz gradient). When conductive windings 802-1 and 802-2 are driven with different drive currents and conductive windings 802-3 and 802-4 are driven with the same drive (or vice versa), Bz' component generator 800 generates a gradient magnetic field in addition to the Bz' component of the compensation magnetic field. The gradient magnetic field is configured to actively shield magnetic field sensing region from fields that linearly vary along the z-axis, as will be explained below in more detail.

As mentioned above, magnetic field generator 108 may include, in addition to or in place of Bz' component generator 800, a Bx' component generator and/or a By' component generator configured to cancel or substantially reduce ambient background magnetic fields along the x-axis and/or the y-axis.

Figures 14A, 14B:
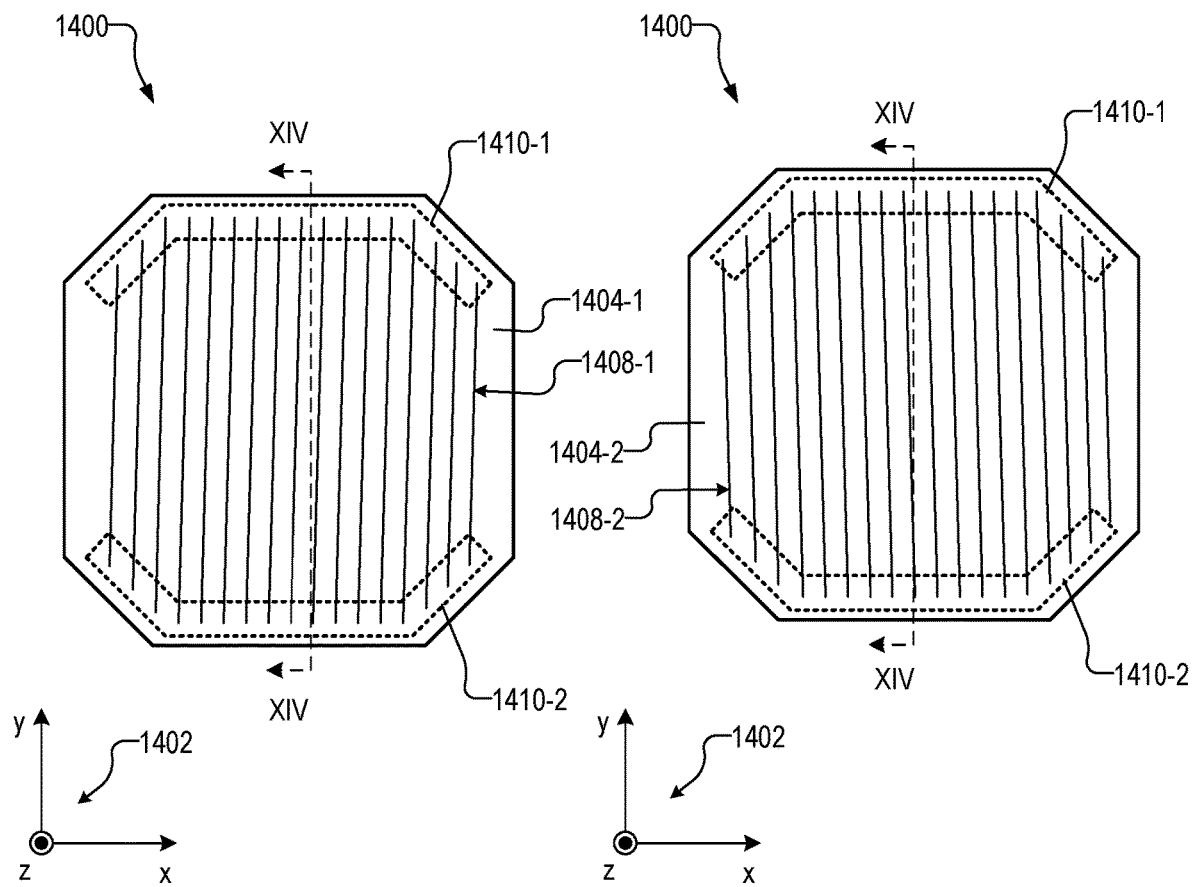
FIGS. 14A and 14B show plan views of an exemplary Bx'/By' component generator according to principles described herein.
Figure 14C:
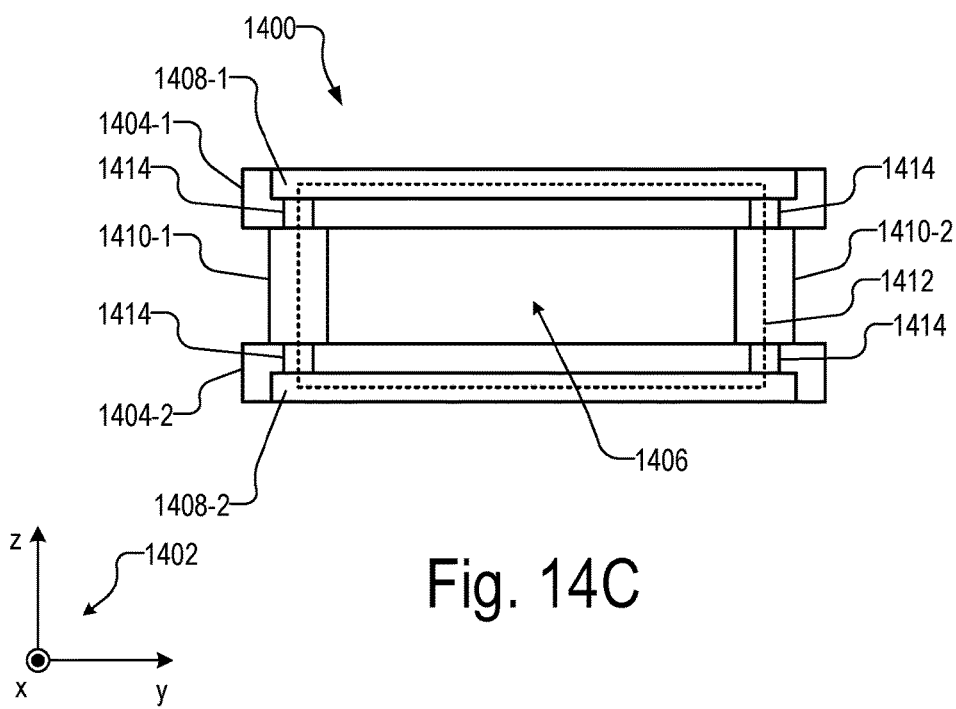
FIG. 14C shows a side view functional diagram of the Bx'/By' component generator of FIGS. 14A and 14B taken along the dashed lines labeled XIV-XIV according to principles described herein.

FIGS. 14A-14C illustrate an exemplary configuration of a Bx'/By' component generator 1400 of magnetic field generator 108. FIGS. 14A and 14B show plan views (e.g., views in the z-direction) of Bx'/By' component generator 1400, and FIG. 14C is a side view functional diagram of Bx'/By' component generator 1400 (e.g., as viewed in the y-direction) taken along the dashed lines labeled XIV-XIV. Legend 1402 indicates an orientation of x-, y-, and z-axes. The orientation of legend 1402 is the same as the orientation of legend 806 relative to magnetic field generator 108.

As shown, Bx'/By' component generator 1400 includes a first substrate 1404-1 and a second substrate 1404-2 positioned opposite to first substrate 1404-1 and separated from first substrate 1404-1 in the z-direction by a gap. Substrates 1404 may be formed of any suitable material, such as but not limited to alumina, ceramics, glass, and/or PCB board. In some examples in which magnetic field generator 108 includes Bx'/By' component generator 1400 in addition to Bz' component generator 800, substrates 1404 and substrates 902 are the same (e.g., substrate 1404-1 is implemented by substrate 902-1 and substrate 1404-2 is implemented by substrate 902-2). In alternative examples, substrates 1404 are different than substrates 902. Exemplary configurations of magnetic field generator 108 will be described below in more detail. Substrates 1404 are shown to have an octagonal shape. However, substrates 1404 may have any shape as may suit a particular implementation.

A magnetic field sensing region 1406 is located in the gap (see FIG. 14C). Magnetic field sensing region 1406 is a region where one or more magnetometers 106 (including respective vapor cells 604) may be located. In some examples in which Bx'/By' component generator 1400 is used in combination with Bz' component generator 800, magnetic field sensing region 1406 is the same as magnetic field sensing region 804.

A first wiring set 1408-1 is arranged on first substrate 1404-1 and a second wiring set 1408-2 is arranged on second substrate 1404-2. Each wiring set 1408 comprises a plurality of electrically unconnected wires extending generally along the y-direction. Wiring sets 1408 may be formed of any suitable conductor of electrical current, such as metallic conductors (e.g., copper, silver, and/or gold) and non-metallic conductors (e.g., carbon). Wiring sets 1408 may be arranged on substrates 1404 in any suitable manner (e.g., etched, printed, soldered, deposited, or otherwise attached).

Interconnects 1410 (e.g., first interconnect 1410-1 and second interconnect 1410-2) are positioned between first substrate 1404-1 and second substrate 1404-2. Interconnects 1410 electrically connect first wiring set 1408-1 with second wiring set 1408-2 to thereby form a continuous electrical path (as represented by the dashed line in FIG. 14C) through first wiring set 1408-1 and second wiring set 1408-2. Interconnects 1410 may electrically connect to wiring sets 1408 in by connections 1414 (e.g., one or more relays, contact pads, wires, etc.). Interconnects 1410 may comprise any suitable electrical connector configured to electrically connect first wiring set 1408-1 on first substrate 1404-1 with second wiring set 1408-2 on second substrate 1404-2. In some examples, each interconnect 1410 is an elastomeric connector that is anisotropically conductive in the z-direction. Suitable elastomeric connectors may include, for example, zebra connectors commercially available from Fujipoly America Corp.

Figure 15A:
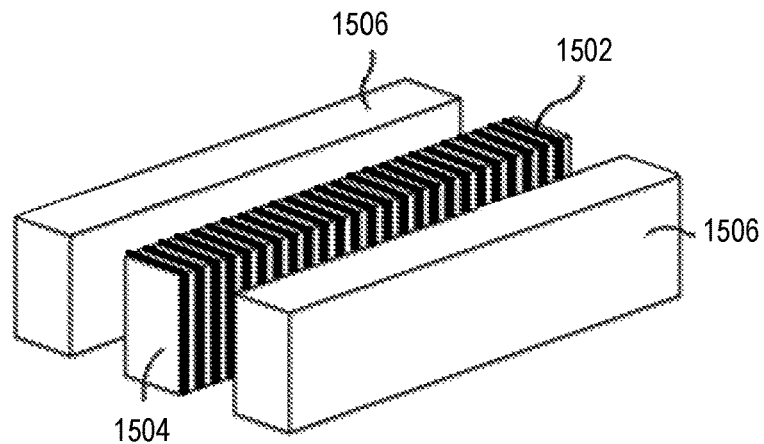
FIGS. 15A and 15B illustrate exemplary configurations of an elastomeric connector that may be used as interconnects in the Bx'/By' component generator of FIGS. 14A-14C according to principles described herein.
Figure 15B:
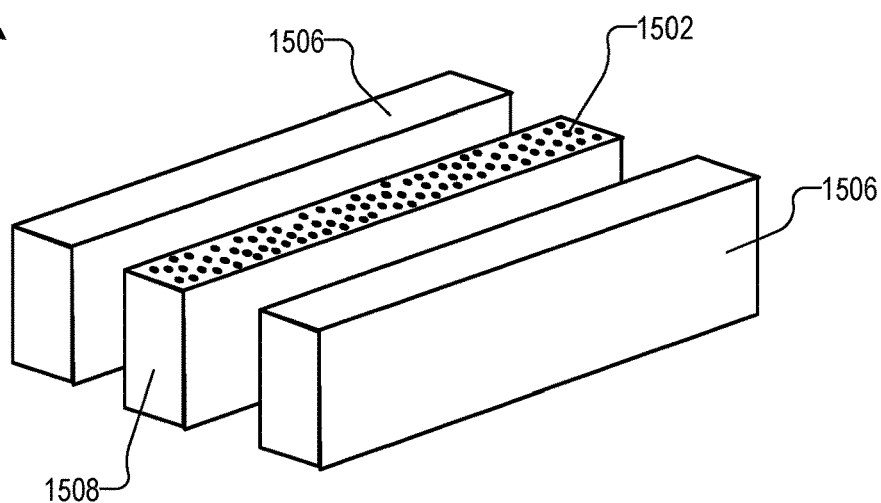

FIGS. 15A and 15B illustrate exemplary configurations of an elastomeric connector that may be used as interconnects 1410. As shown in FIG. 15A, a lamination-type elastomeric connector 1500A includes a plurality of thin, planar conductive elements 1502, each of which is electrically isolated from other conductive elements 1502 by intervening isolation elements 1504. Conductive elements 1502 may be formed of any suitable conductive material (e.g., silver, gold, copper, etc.). Isolation elements 1504 may be formed of any suitable electrically insulating material (e.g., an elastomeric material). Conductive elements 1502 and isolation elements 1504 are stacked in an alternating pattern. In some examples, as shown in FIG. 15A, conductive elements 1502 and isolation elements 1504 are enclosed between side support barriers 1506-1 and 1506-2. Side support barriers 1506 may also be formed of a suitable electrically insulating material. When elastomeric connector 1500A is positioned between substrates 1404, each conductive element 1502 is oriented in the z-direction and makes contact with first substrate 1404-1 and second substrate 1404-2 (e.g., with contact pads on first substrate 1404-1 and second substrate 1404-2).

FIG. 15B illustrates an exemplary matrix-type elastomeric connector 1500B. Elastomeric connector 1500B is the same as elastomeric connector 1500A except that conductive elements 1502 comprise fine conductive wires embedded within an elastomer matrix 1508.

Referring again to FIGS. 14A-14C, continuous electrical path 1412 forms a conductive winding configured to generate, when supplied with a drive current, a Bx' component of a compensation magnetic field. The Bx' component of the compensation magnetic field is configured to actively shield magnetic field sensing region 1406 from ambient background magnetic fields along the x-axis. For example, Bx'/By' component generator 1400 may substantially reduce or cancel a Bx component of ambient background magnetic fields at magnetic field sensing region 1406. In some examples, the Bx' component of the compensation magnetic field is substantially equal and opposite to the Bx component of the ambient background magnetic fields.

Figures 16A, 16B:
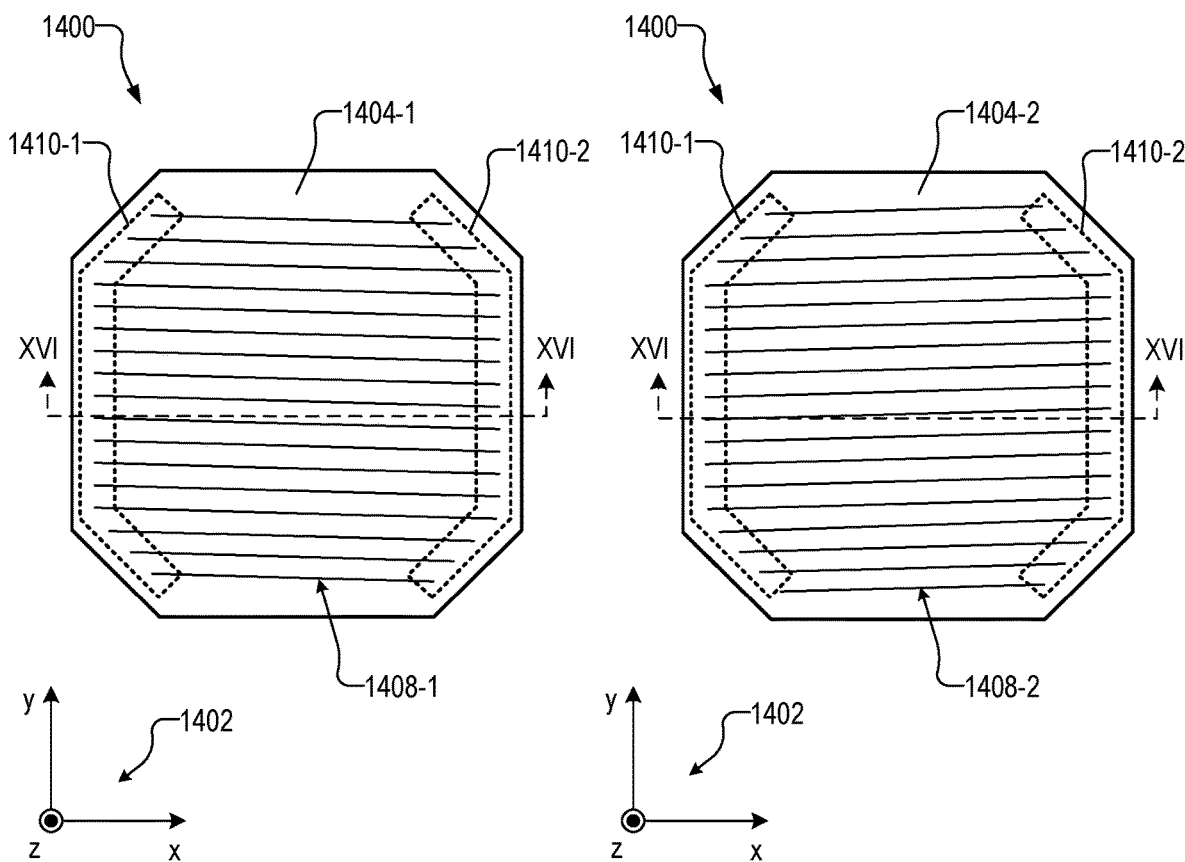
FIGS. 16A and 16B show plan views of another exemplary Bx'/By' component generator according to principles described herein.
Figure 16C:
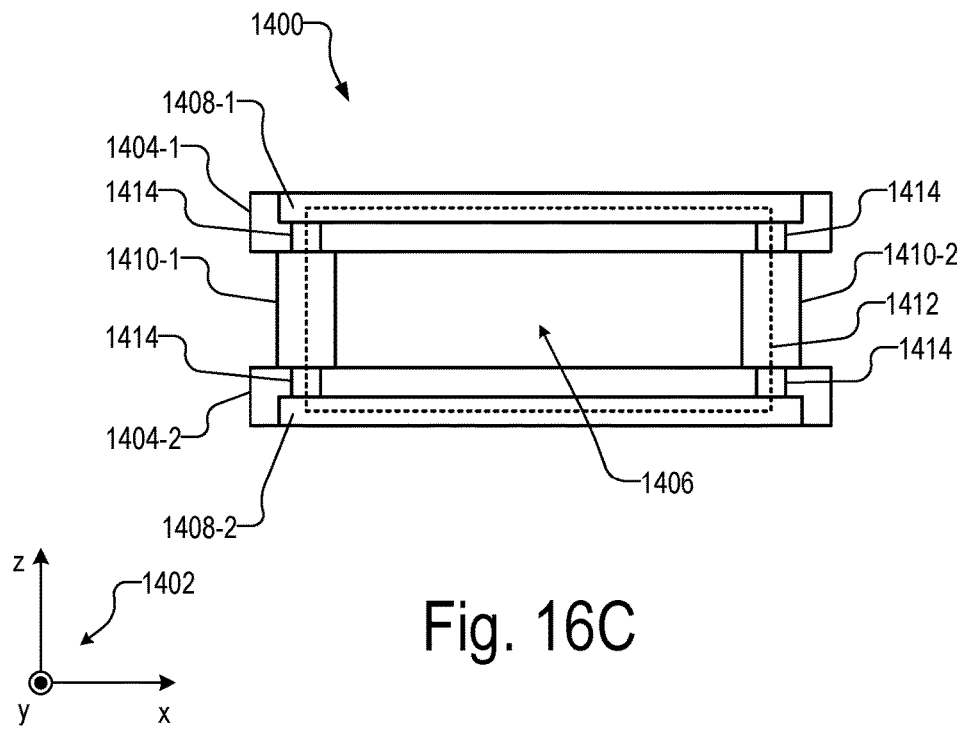
FIG. 16C shows a side view functional diagram of the Bx'/By' component generator of FIGS. 16A and 16B taken along the dashed lines labeled XVI-XVI according to principles described herein.

In alternative embodiments, Bx'/By' component generator 1400 may be configured to generate a By' component of the compensation magnetic field. FIGS. 16A-16C illustrate another exemplary configuration of Bx'/By' component generator 1400. FIGS. 16A-16C are the same as FIGS. 14A-14C except that wiring sets 1408 extend generally in the x-direction. Thus, continuous electrical path 1412 forms a conductive winding configured to generate, when supplied with a drive current, a By' component of a compensation magnetic field. The By' component of the compensation magnetic field is configured to actively shield magnetic field sensing region 1406 from ambient background magnetic fields along the y-axis. For example, Bx'/By' component generator 1400 may substantially reduce or cancel a By component of ambient background magnetic fields at magnetic field sensing region 1406. In some examples, the By' component of the compensation magnetic field is substantially equal and opposite to the By component of the ambient background magnetic fields.

Figures 17A, 17B:
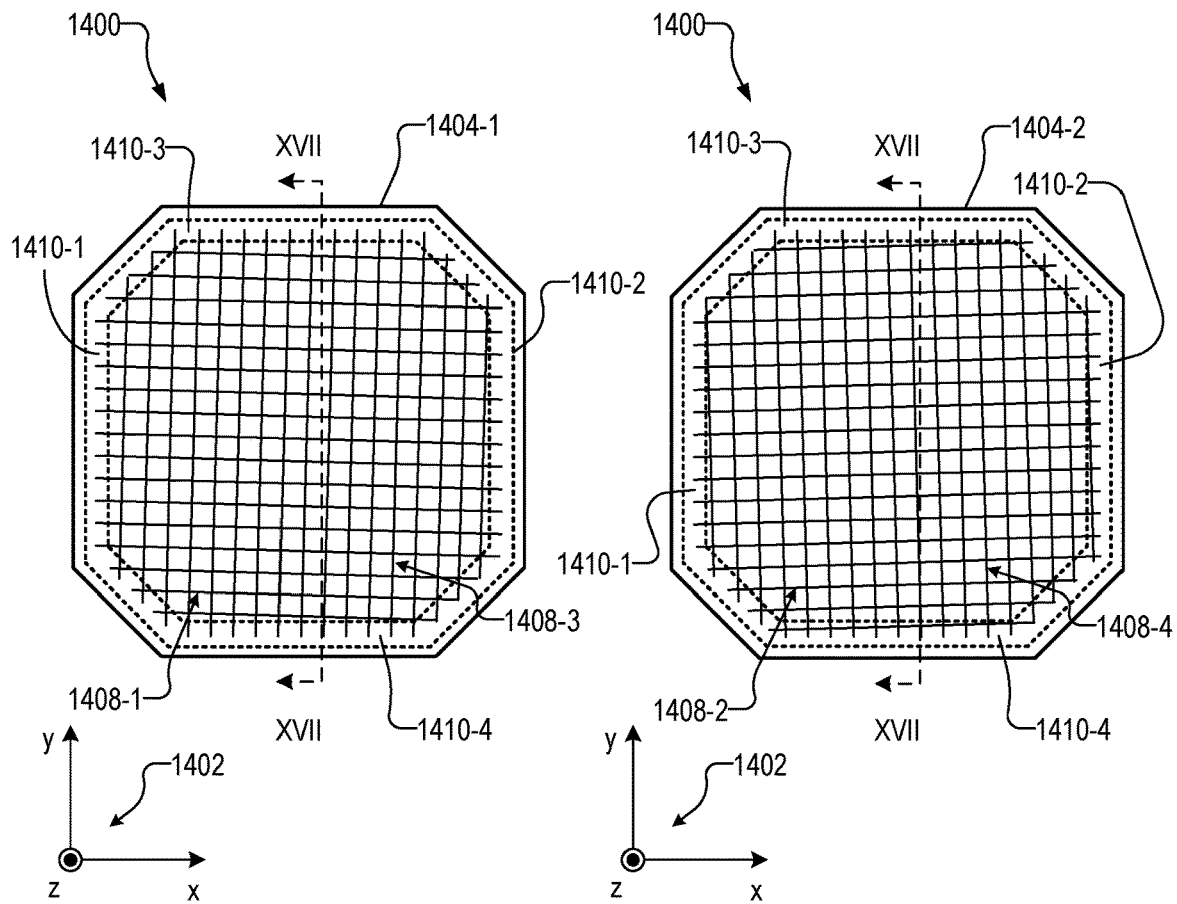
FIGS. 17A and 17B show plan views of another exemplary Bx'/By' component generator according to principles described herein.
Figure 17C:
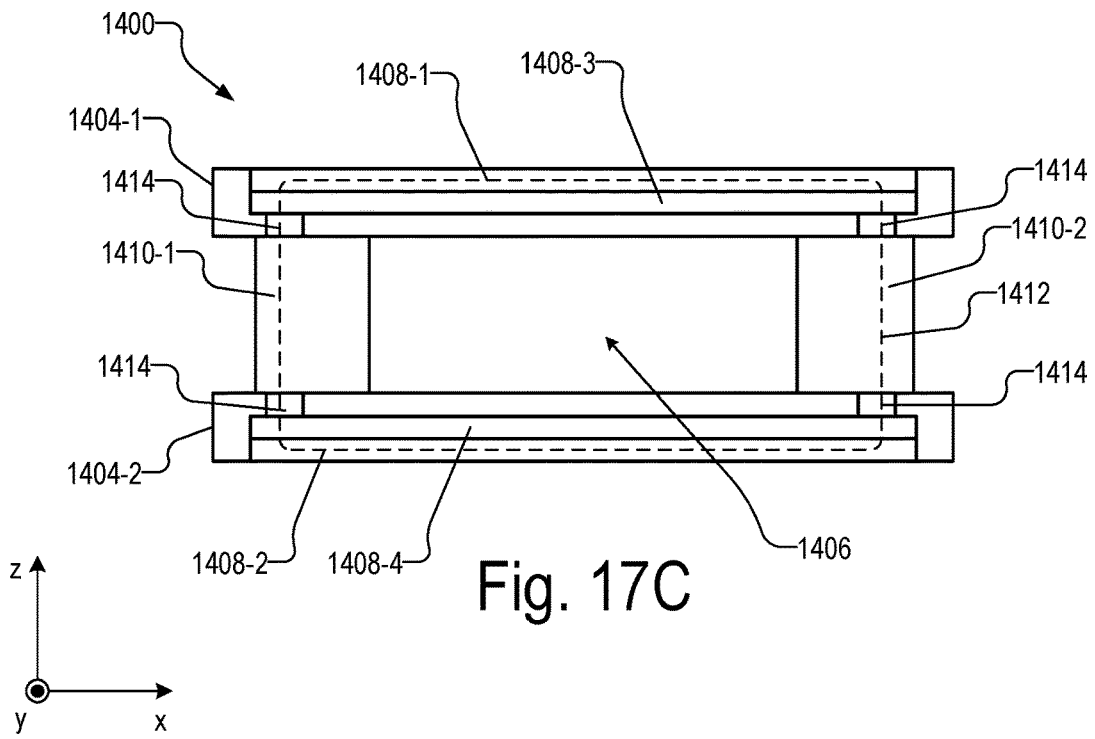
FIG. 17C shows a side view functional diagram of the Bx'/By' component generator of FIGS. 17A and 17B taken along the dashed lines labeled XVII-XVII according to principles described herein.

In some embodiments, Bx'/By' component generator 1400 is configured to actively shield magnetic field sensing region 1406 from ambient background magnetic fields in both the x-direction and the y-direction. FIGS. 17A-17C show another exemplary configuration of Bx'/By' component generator 1400. FIGS. 17A-17C are the same as FIGS. 14A-14C except that a third wiring set 1408-3 is arranged on first substrate 1404-1 in addition to first wiring set 1408-1, and a fourth wiring set 1408-4 is arranged on second substrate 1404-2 in addition to second wiring set 1408-2. First wiring set 1408-1 and second wiring set 1408-2 extend generally in the y-direction while third wiring set 1408-3 and fourth wiring set 1408-4 extend generally in the x-direction. Interconnects 1410-1 and 1410-2 electrically connect first wiring set 1408-1 with second wiring set 1408-2 to form a first continuous electrical path 1412 through first wiring set 1408-1 and second wiring set 1408-2, and interconnects 1410-3 and 1410-4 electrically connect third wiring set 1408-3 with fourth wiring set 1408-4 to thereby form a second continuous electrical path (not shown in FIG. 17C) through third wiring set 1408-3 and fourth wiring set 1408-4. Interconnects 1410-3 and 1410-4 may be implemented, for example, by an elastomeric connector, as described above. As shown in FIGS. 17A and 17B, interconnects 1410 are formed by a single elastomeric connector that surrounds magnetic field sensing region 1406. In other embodiments, interconnects 1410 are not connected to one another but are separate structures.

As shown in FIG. 17C, first continuous electrical path 1412 forms a first conductive winding configured to generate, when supplied with a drive current, a Bx' component of a compensation magnetic field. The second continuous electrical path (not shown) forms a second conductive winding configured to generate, when supplied with a drive current, a By' component of the compensation magnetic field.

As shown in FIG. 17C, first wiring set 1408-1 and third wiring set 1408-3 are both arranged on first substrate 1404-1, and second wiring set 1408-2 and fourth wiring set 1408-4 are both arranged on second substrate 1404-2. In this embodiment, first wiring set 1408-1 is separated from third wiring set 1408-3 by an electrical insulator (not shown) and second wiring set 1408-2 is separated from fourth wiring set 1408-4 by an electrical insulator (not shown). In alternative embodiments, first wiring set 1408-1 and third wiring set 1408-3 are arranged on opposite surface of first substrate 1404-1, and second wiring set 1408-2 and fourth wiring set 1408-4 are arranged on opposite surface of second substrate 1404-2. In yet other embodiments, each wiring set 1408 is arranged on a different substrate.

In the examples described above, wiring sets 1408 (and hence conductive windings formed by wiring sets 1408) may have any winding pattern as may suit a particular implementation. In some examples the winding patterns of wiring sets 1408 may be automatically generated by a magnetic field generator design system configured to optimize the winding patterns based on a set of inputs. An exemplary magnetic field generator design system will be described below in more detail. Generally, the winding patterns of the Bx' component and/or By' component conductive windings are configured to generate a homogeneous magnetic field at the magnetic field sensing region. The winding patterns may be configured to generate a homogeneous magnetic field that is approximately 30% the size of wiring sets 1408, as measured along the x- or y-direction.

As mentioned above, in some embodiments magnetic field generator 108 includes both Bz' component generator 800 and Bx'/By' component generator 1400. With this configuration magnetic field generator 108 is configured to actively shield magnetic field sensing region 804/1406 from ambient background magnetic fields along the x-, y-, and z-axes. In some examples, conductive windings 802 of Bz' component generator 800 are arranged on substrates 1404 of Bx'/By' component generator 1400. In such examples conductive windings 802 are electrically insulated from wiring sets 1408. In alternative examples, conductive windings 802 of Bz' component generator 800 are arranged on substrates (e.g., substrates 902 of Bz' component generator 800) that are different from substrates 1404 of Bx'/By' component generator 1400. An exemplary physical implementation of magnetic field generator 108 will be described below in more detail.

As mentioned, magnetic field generator 108 is configured to actively shield a magnetic sensing region from ambient magnetic fields along the x-, y, and/or z-axes. In some examples, magnetic field generator 108 is further configured to actively shield the magnetic sensing region from first-order gradient magnetic fields, e.g., ambient background magnetic fields that linearly vary in the x-, y-, and/or z-direction. The ambient background magnetic field B is a vector magnetic field that has magnitude and direction at each point in space. Using the Cartesian coordinate system, ambient background magnetic field B can be expressed as:

$$B = i \cdot Bx + j \cdot By + k \cdot Bz$$

where Bx, By and Bz are the Cartesian components of the ambient background magnetic field and i, j, and k are unit vectors along the x-, y-, and z-axes. The gradient of B, denoted ∇B, is a second order tensor, a matrix of nine partial derivatives of the three principal components of B (Bx, By, and Bz) with respect to the three cardinal axes (x, y, and z):

$$\nabla B = \begin{bmatrix} \frac{dBx}{dx} & \frac{dBy}{dx} & \frac{dBz}{dx} \\ \frac{dBx}{dy} & \frac{dBy}{dy} & \frac{dBz}{dy} \\ \frac{dBx}{dz} & \frac{dBy}{dz} & \frac{dBz}{dz} \end{bmatrix}$$

As can be seen from ∇B, there are nine possible gradient components of the ambient background magnetic fields. Accordingly, magnetic field generator 108 may further be configured to actively shield magnetic field sensing regions 804 and/or 1406 from any one or more of the gradient components of the ambient background magnetic fields. However, in some examples it is not necessary to generate every gradient component of the compensation magnetic field. Instead, the gradients components of the ambient background magnetic fields can be actively shielded by generating a subset of gradient components of the compensation magnetic field, as will now be described.

As mentioned above, Bz' component generator 800 is configured to generate one or more z-axis gradient components of the compensation magnetic field when at least two conductive windings 802 (e.g., conductive windings 802-1 and 802-2) are driven with different drive currents. For example, controller 104 may be configured to drive Bz' component generator 800 to generate a dBz'/dz gradient component, a dBz'/dx gradient component, and/or a dBz'/dy gradient component of the compensation magnetic field.

Figure 18A:
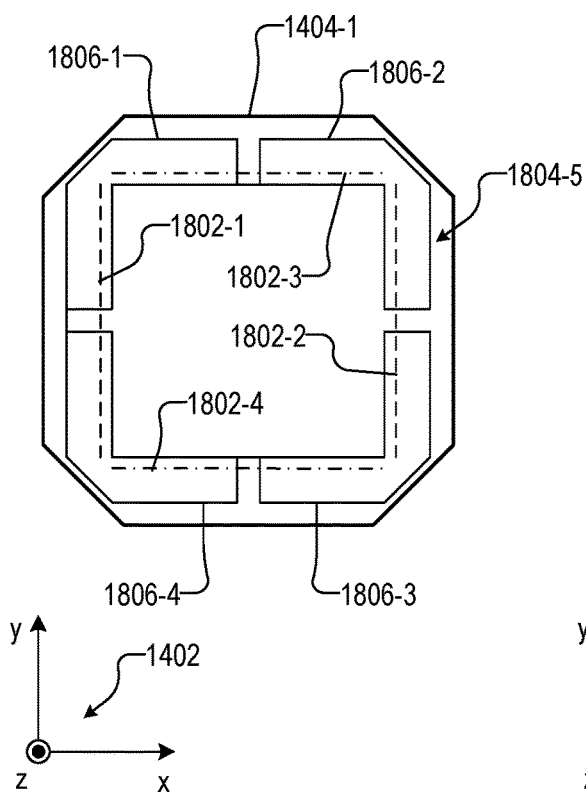
FIGS. 18A and 18B show plan views of an exemplary configuration of a Bx'/By' component generator according to principles described herein.
Figure 18B:
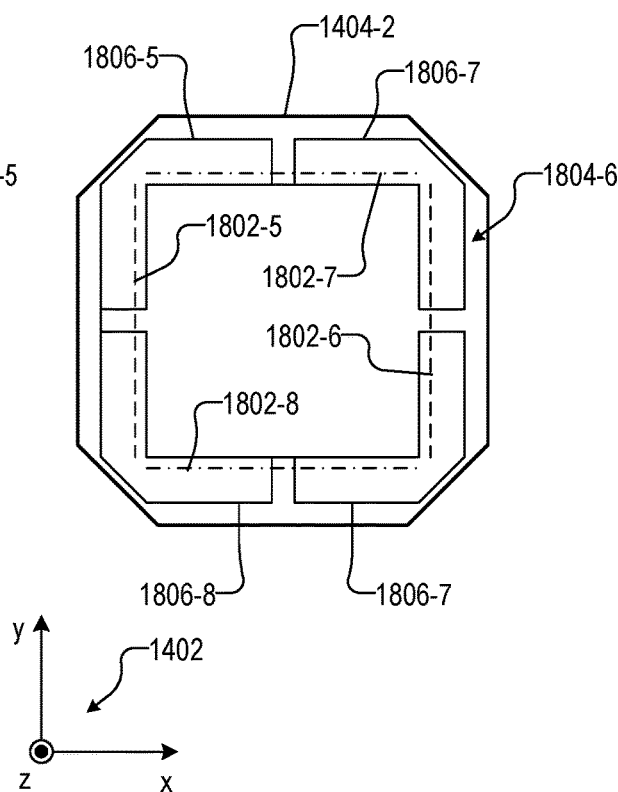
Figure 18C:
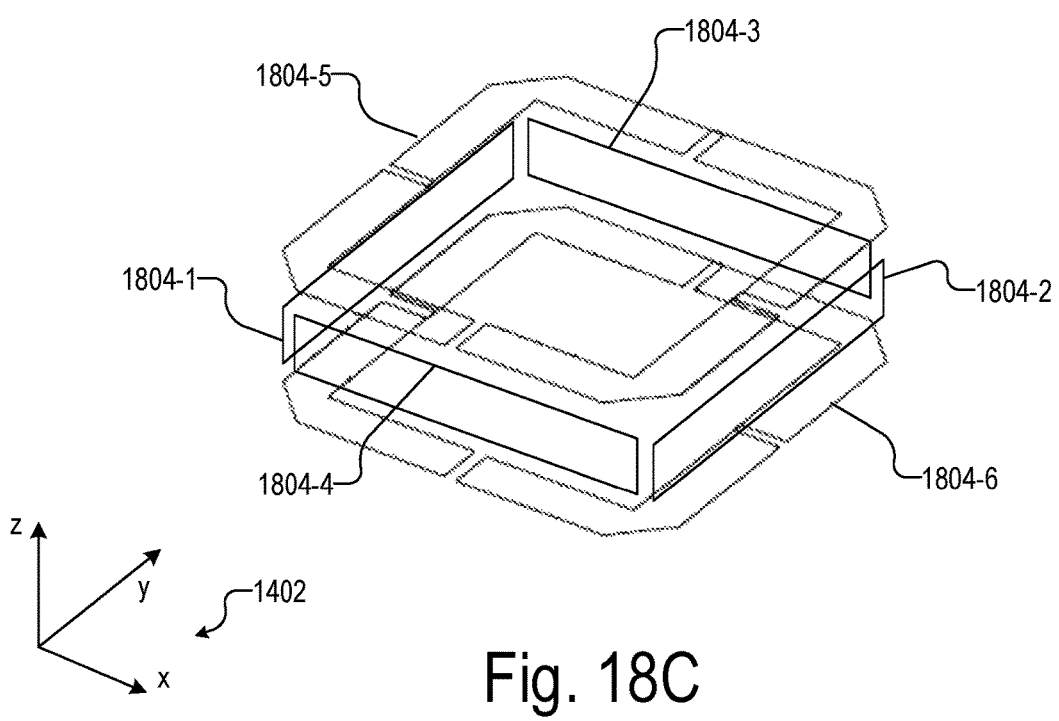
FIG. 18C shows a perspective view of various conductive windings that may be included in the Bx'/By' component generator of FIGS. 18A and 18B according to principles described herein.

In some embodiments, Bx'/By' component generator 1400 may also be configured to generate one or more gradient components of the compensation magnetic field. FIGS. 18A-18C illustrate an exemplary configuration of Bx'/By' component generator 1400 having conductive windings configured to generate gradient components of the compensation magnetic field. FIGS. 18A and 18B show plan views (e.g., views in the z-direction) of Bx'/By' component generator 1400, and FIG. 18C is a perspective view of various conductive windings included in Bx'/By' component generator 1400. Legend 1402 indicates an orientation of x-, y-, and z-axes. In FIGS. 18A-18C, wiring sets 1408 have been omitted to facilitate discussion of the gradient component conductive windings.

As shown in FIG. 18A, first substrate 1404-1 includes a first gradient wiring 1802-1 extending generally in the y-direction along a first edge of first substrate 1404-1 and a second gradient wiring 1802-2 extending generally in the y-direction along a second edge of first substrate 1404-1. First gradient wiring 1802-1 and second gradient wiring 1802-2 are substantially parallel to each other and are represented by dashed lines. First substrate 1404-1 also includes a third gradient wiring 1802-3 extending generally in the x-direction along a third edge of first substrate 1404-1 and a fourth gradient wiring 1802-4 extending generally in the x-direction along a fourth edge of first substrate 1404-4. Third gradient wiring 1802-3 and fourth gradient wiring 1802-4 are substantially parallel to each other and are represented by dash-dot-dash lines. Third gradient wiring 1802-3 and fourth gradient wiring 1802-4 are not electrically connected to first gradient wiring 1802-1 or second gradient wiring 1802-1.

As shown in FIG. 18B, second substrate 1404-2 includes a fifth gradient wiring 1802-5 extending generally in the y-direction along a first edge of second substrate 1404-2 and a sixth gradient wiring 1802-6 extending generally in the y-direction along a second edge of second substrate 1404-2. Fifth gradient wiring 1802-5 and sixth gradient wiring 1802-6 are substantially parallel to each other and are represented by dashed lines. Second substrate 1404-2 also includes a seventh gradient wiring 1802-7 extending generally in the x-direction along a third edge of second substrate 1404-2 and an eighth gradient wiring 1802-8 extending generally in the x-direction along a fourth edge of second substrate 1404-2. Seventh gradient wiring 1802-7 and eighth gradient wiring 1802-8 are substantially parallel to each other and are represented by dash-dot-dash lines. Seventh gradient wiring 1802-7 and eighth gradient wiring 1802-8 are not electrically connected to fifth gradient wiring 1802-5 or sixth gradient wiring 1802-6.

Gradient wirings 1802 may each comprise one or more wires and may be formed of any suitable conductor of electrical current, such as metallic conductors (e.g., copper, silver, and/or gold) and non-metallic conductors (e.g., carbon). Gradient wirings 1802 may be arranged on substrates 1404 in any suitable manner (e.g., etched, printed, soldered, deposited, or otherwise attached). Furthermore, gradient wirings 1802 may be arranged on any surfaces of substrates 1404 as may suit a particular implementation.

When interconnects 1410 are positioned between first substrate 1404-1 and second substrate 1404-2, as shown in FIGS. 17A-17C, interconnects 1410 electrically connect gradient wirings 1802 on first substrate 1404-1 with gradient wirings 1802 on second substrate 1404-2. For example, interconnects 1410 electrically connect first gradient wiring 1802-1 with fifth gradient wiring 1802-5 to thereby form a first continuous electrical path, which forms a first conductive winding 1804-1, as shown in FIG. 18C. Similarly, interconnects 1410 electrically connect second gradient wiring 1802-2 with sixth gradient wiring 1802-6 to thereby form a second continuous electrical path, which forms a second conductive winding 1804-2. Interconnects 1410 also electrically connect third gradient wiring 1802-3 with seventh gradient wiring 1802-7 to thereby form a third continuous electrical path, which forms a third conductive winding 1804-3. Interconnects 1410 further electrically connect fourth gradient wiring 1802-4 with eighth gradient wiring 1802-8 to thereby form a fourth continuous electrical path, which forms a fourth conductive winding 1804-4.

To generate a dBx'/dx gradient component of the compensation magnetic field, controller 104 drives first conductive winding 1804-1 and second conductive winding 1804-2 with equal but opposite currents. The combination of the magnetic fields generated by conductive windings 1804-1 and 1804-2 generates a dBx'/dx gradient component that linearly varies in the x-direction. Similarly, to generate a dBy'/dy gradient component of the compensation magnetic field, controller 104 drives third conductive winding 1804-3 and fourth conductive winding 1804-4 with equal but opposite currents. The combination of the magnetic fields generated by conductive windings 1804-3 and 1804-4 generates a dBy'/dy gradient component that linearly varies in the y-direction.

Bx'/By' component generator 1400 is further configured to generate a combination gradient component that is the sum of dBx'/dy and dBy'/dx gradient components of the compensation magnetic field. To this end, first substrate 1404-1 further includes a fifth conductive winding 1804-5 that is formed of four L-shaped loops 1806 (e.g., loops 1806-1 to 1806-4) positioned at each corner of first substrate 1404-1. In some examples, as shown in FIGS. 18A-18C, loops 1806 are connected to each other in series. Second substrate 1404-2 includes a sixth conductive winding 1804-6 that is formed of four L-shaped loops 1806 (e.g., loops 1806-5 to 1806-8) positioned at each corner of second substrate 1404-2. In some examples, as shown in FIGS. 18A-18C, loops 1806 are connected to each other in series. Conductive windings 1804-5 and 1804-6 are not electrically connected to each other, whether by interconnects 1410 or otherwise. Controller 104 may drive conductive windings 1804-5 and 1804-6 with equal but opposite drive currents to thereby generate a combination gradient component that is the sum of dBx'/dy and dBy'/dx gradient components.

It will be recognized that the configuration of conductive windings 1804 described above is merely exemplary and not limiting, as conductive windings 1804 may have any other configuration or winding pattern as may suit a particular implementation. Furthermore, in alternative embodiments Bx'/By' component generator 1400 may not include all conductive windings 1804. For example, if Bx'/By' component generator 1400 is configured to actively shield magnetic field sensing region 1406 from ambient background magnetic fields in only the x-direction, Bx'/By' component generator 1400 may include only conductive windings 1804-1 and 1804-2.

Figure 19:
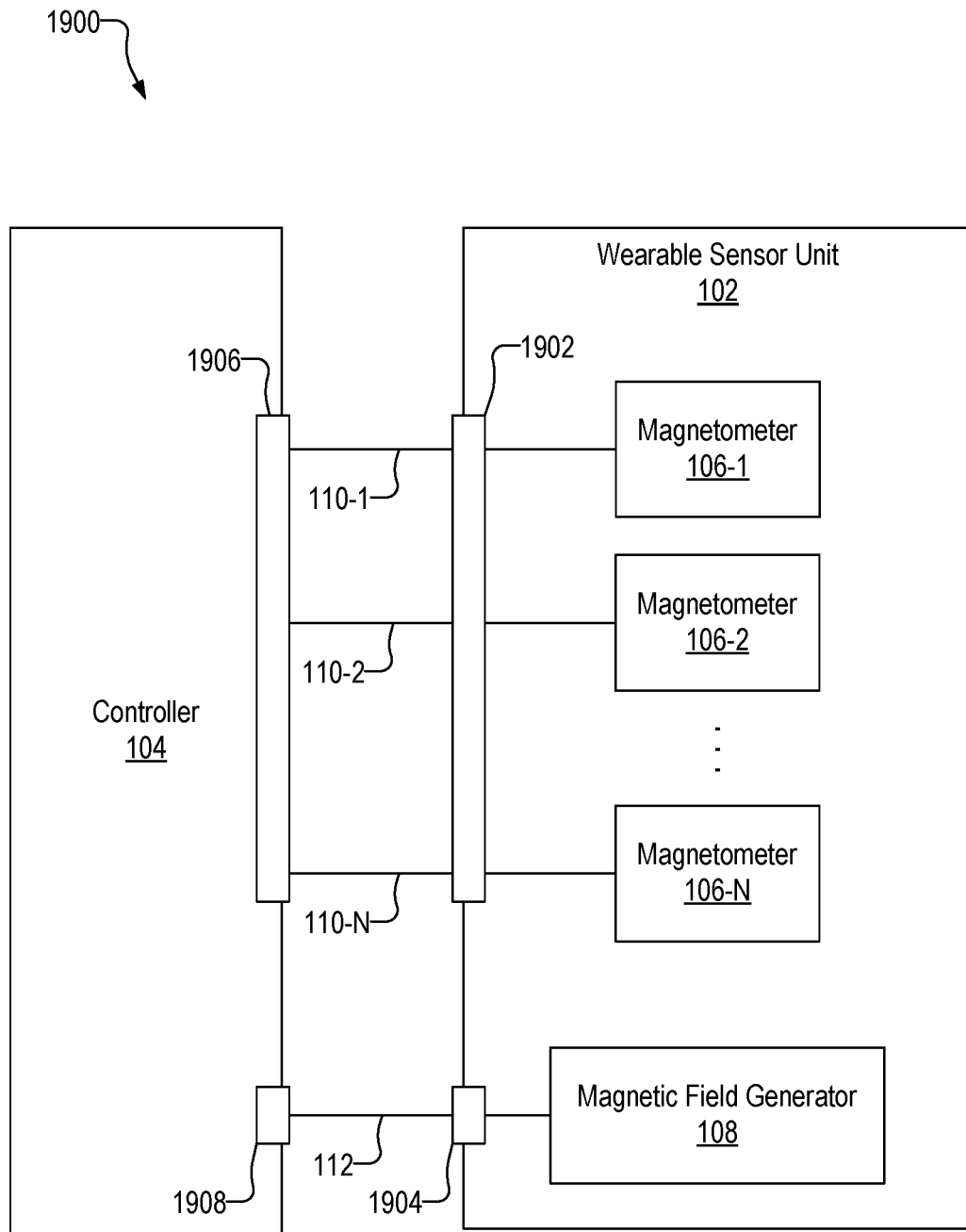
FIG. 19 shows an exemplary configuration in which a wearable sensor unit 102 and a controller each include connection interfaces configured to facilitate wired connections therebetween according to principles described herein.

FIG. 19 shows an exemplary configuration 1900 in which wearable sensor unit 102 and controller 104 each include connection interfaces configured to facilitate wired connections therebetween. As shown, wearable sensor unit 102 includes a connection interface 1902 for magnetometers 106 and a connection interface 1904 for magnetic field generator 108. Controller 104 includes a connection interface 1906 corresponding to connection interface 1902 and a connection interface 1908 corresponding to connection interface 1904. Connection interfaces 1902, 1904, 1906, and 1908 may each be implemented in any suitable manner.

To illustrate, connection interface 1902 may be implemented by one or more twisted pair cable interface assemblies electrically connected to one or more components within magnetometers 106, and connection interface 1906 may be implemented by one or more twisted pair cable interface assemblies electrically connected to one or more components within controller 104. In this configuration, communication links 110 may be implemented by one or more twisted pair cables each including one or more twisted pairs of wires that are configured to electrically connect specific components of magnetometers 106 and/or other elements of wearable sensor unit 102 with specific components of controller 104. The one or more twisted pair cable interface assemblies of wearable sensor unit 102 and controller 104 may each be configured to connect to a twisted pair cable in any suitable manner.

In this configuration, controller 104 may be configured to interface with one or more components included in magnetometers 106 and/or other elements of wearable sensor unit 102 by transmitting signals to the one or more components over one or more twisted pair cables and/or receiving signals from the one or more components over the one or more twisted pair cables.

Figure 20:
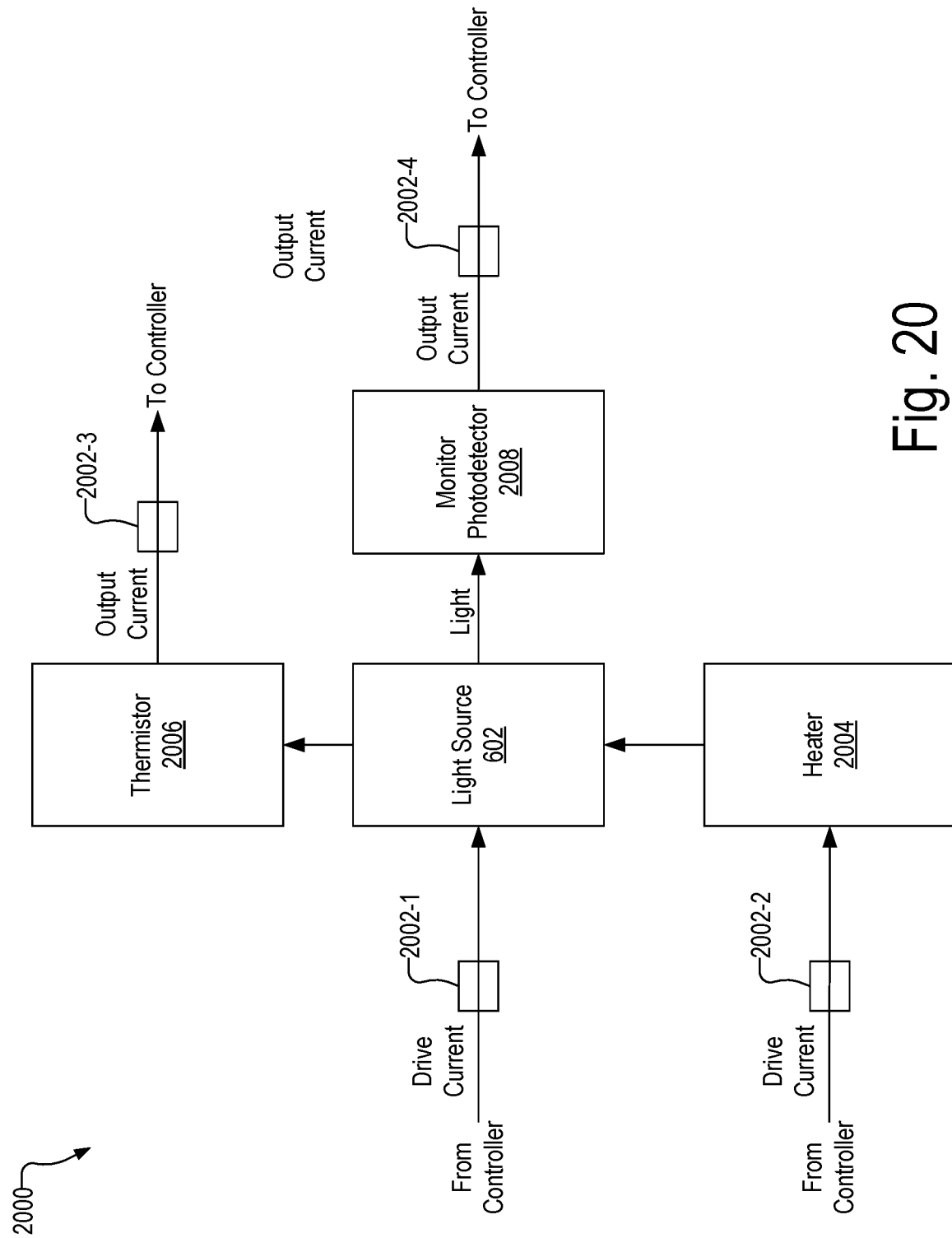
FIG. 20 shows an exemplary configuration in which a controller interfaces with various components of or associated with a particular magnetometer by way of a plurality of twisted pair cable interfaces according to principles described herein.

To illustrate, FIG. 20 shows an exemplary configuration 2000 in which controller 104 interfaces with various components of or associated with a particular magnetometer 106 by way of a plurality of twisted pair cable interfaces 2002 (e.g., twisted pair cable interfaces 2002-1 through 2002-4) included in wearable sensor unit 102. As shown, twisted pair cable interface 2002-1 is electrically connected to an input of light source 602 (described above in connection with FIG. 6), twisted pair cable interface 2002-2 is electrically connected to an input of a heater 2004 for light source 602, twisted pair cable interface 2002-3 is electrically connected to an output of a thermistor 2006 for light source 602, and twisted pair cable interface 2002-4 is electrically connected to an output of a monitor photodetector 2008 for light source 602.

As mentioned, light source 602 is configured to generate and output light that enters and exits (e.g., by passing through) vapor cell 604 (not shown in FIG. 20). To control (e.g., drive) light source 602, controller 104 may supply a drive current to the input of light source 602 by way of twisted pair cable interface 2002-1. For example, this drive current may be supplied by controller 104 over a twisted pair of wires included in a twisted pair cable connected to twisted pair cable interface 2002-1.

As shown, the light output by light source 602 may be detected by monitor photodetector 2008, which is configured to detect the light before the light enters vapor cell 604 and output current representative of the detected light. Controller 104 may use the output of monitor photodetector 2008 to monitor and compensate for a behavior of light source 602 in any suitable manner. For example, based on the output of monitor photodetector 2008, controller 104 may adjust the drive current provided to light source 602.

Controller 104 may be configured to read an output of monitor photodetector 2008 by way of twisted pair cable interface 2002-4. For example, controller 104 may receive the current output by monitor photodetector 2008 over a twisted pair of wires included in a twisted pair cable connected to twisted pair cable interface 2002-4.

Heater 2004 may be configured to apply heat to light source 602. To this end, heater 2004 may be thermally coupled to light source 602. To control (e.g., drive) heater 2004, controller 104 may supply a drive current to the input of heater 2004 by way of twisted pair cable interface 2002-2. For example, this drive current may be supplied by controller 104 over a twisted pair of wires included in a twisted pair cable connected to twisted pair cable interface 2002-2.

Thermistor 2006 may be configured to detect the operating temperature of light source 602 and output current representative of the operating temperature. To this end, thermistor 2006 may be thermally coupled to light source 602. Controller 104 may be configured to read an output of thermistor 2006 by way of twisted pair cable interface 2002-3. For example, controller 104 may receive the current output by thermistor 2006 over a twisted pair of wires included in a twisted pair cable connected to twisted pair cable interface 2002-3.

Heater 2004 and thermistor 2006 may be used by controller 104 to control an operating temperature of light source 602. For example, heater 2004 and thermistor 2006 may be used to temperature control light source 602 down to a particular threshold (e.g., within one millikelvin of temperature stability).

Any of the twisted pair cable interfaces 2002 shown in FIG. 20 may be used by controller 104 to interface with multiple components within wearable sensor unit 102. For example, twisted pair cable interface 2002-1 may be used to supply drive current to all of the light sources 602 included in an array of magnetometers 106. To illustrate, if there are twenty-five light sources 602 included in wearable sensor unit 102, twisted pair cable interface 2002-1 may include twenty-five pairs of twisted wire each configured to be used by controller 104 to supply drive current to a different one of the twenty-five light sources 602. Likewise, twisted pair cable interface 2002-2 may be used to interface with a plurality of heaters 2004, twisted pair cable interface 2002-3 may be used to interface with a plurality of thermistors 2006, and twisted pair cable interface 2002-4 may be used to interface with a plurality of monitor photodiodes 2008.

Figure 21:
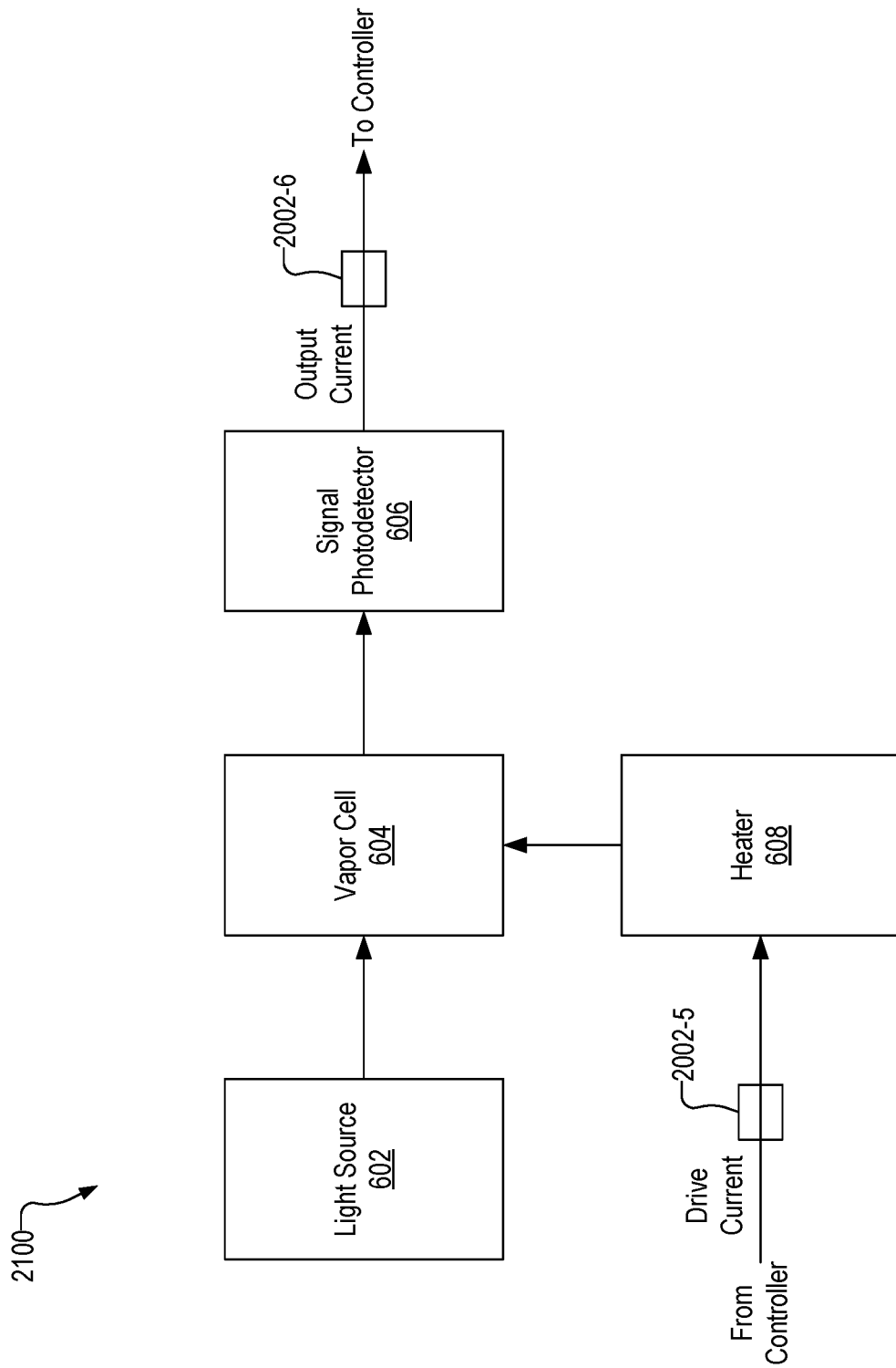
FIG. 21 shows another exemplary configuration in which a controller interfaces with various components of a particular magnetometer by way of a plurality of twisted pair cable interfaces according to principles described herein.

FIG. 21 shows another exemplary configuration 2100 in which controller 104 interfaces with various components of a particular magnetometer 106 by way of a plurality of twisted pair cable interfaces 2002 included in wearable sensor unit 102. FIG. 21 is similar to FIG. 6 in that it depicts light source 602, vapor cell 604, signal photodetector 606, and heater 608. However, FIG. 21 further shows that a twisted pair cable interface 2002-5 is electrically connected to an input of heater 608 and a twisted pair cable interface 2002-6 is electrically connected to an output of signal photodetector 606.

In configuration 2100, controller 104 may control (e.g., drive) heater 608 by supplying a drive current to the input of heater 608 by way of twisted pair cable interface 2002-5. For example, this drive current may be supplied by controller 104 over a twisted pair of wires included in a twisted pair cable connected to twisted pair cable interface 2002-5. Controller 104 may read an output of signal photodetector 606 by way of twisted pair cable interface 2002-6. For example, controller 104 may receive the current output by signal photodetector 606 over a twisted pair of wires included in a twisted pair cable connected to twisted pair cable interface 2002-6. As described above, twisted pair cable interfaces 2002-5 and 2002-6 may in some examples be used to interface with multiple heaters 608 and signal photodetectors 606, respectively.

Returning to FIG. 19, in some examples, connection interface 1904 and connection interface 1908 are each implemented by one or more coaxial cable interface assemblies. In this configuration, communication link 112 may be implemented by one or more coaxial cables each configured to electrically connect specific components of magnetic field generator 108 with specific components of controller 104. The one or more coaxial cable interface assemblies of wearable sensor unit 102 and controller 104 may each be configured to connect to a coaxial cable in any suitable manner.

Figure 22:
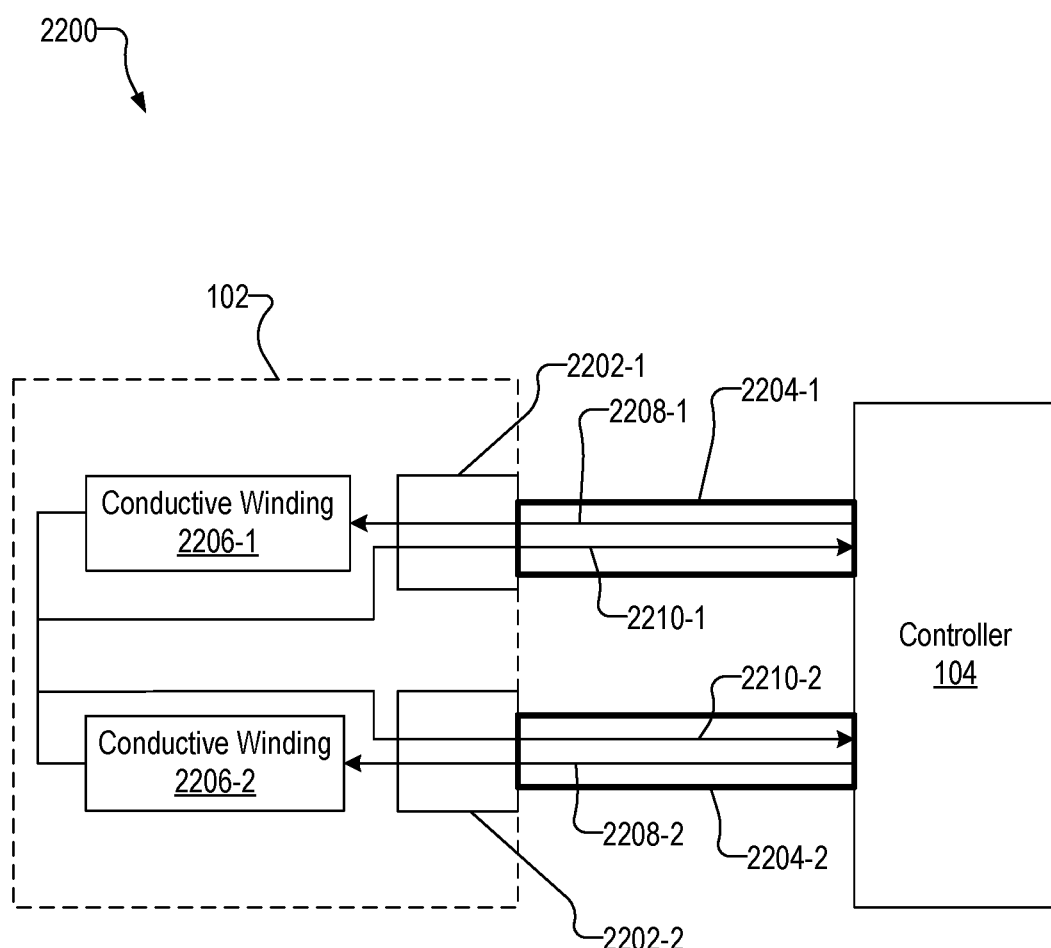
FIG. 22 shows an exemplary configuration in which a controller interfaces with various components of a magnetic field generator by way of a plurality of coaxial cable interfaces according to principles described herein.

To illustrate, FIG. 22 shows an exemplary configuration 2200 in which controller 104 interfaces with various components of magnetic field generator 108 by way of a plurality of coaxial cable interfaces 2202 (e.g., coaxial cable interfaces 2202-1 and 2202-2) included in wearable sensor unit 102. As shown, a coaxial cable 2204-1 is connected to coaxial cable interface 2202-1 and to controller 104 (e.g., a coaxial cable interface that implements connection interface 1908). Likewise, a coaxial cable 2204-2 is connected to coaxial cable interface 2202-2 and to controller 104 (e.g., another coaxial cable interface that implements connection interface 1908).

In this configuration, controller 104 may supply a drive current to a first conductive winding 2206-1 included in magnetic field generator 108 by way of conductive path 2208-1. Likewise, controller 104 may supply a drive current to a second conductive winding 2206-2 included in magnetic field generator 108 by way of conductive path 2208-2. Conductive paths 2208-1 and 2208-2 may be implemented, for example, by center pins included in coaxial cables 2204-1 and 2204-2, respectively. In some examples, as shown in FIG. 22, conductive return paths 2210-1 and 2210-2 (which may be implemented by conductive braids included in coaxial cables 2204) may be connected such that the return paths are common for both conductive windings 2206. In this manner, the potential of all of the return paths is maintained at ground, which may be advantageous for suppression of fringe magnetic fields. Moreover, this configuration may prevent conductive windings 2206 from having to be insulated from each other to maintain a nonzero potential with respect to each other. However, in some alternative embodiments, the return paths for conductive windings 2206 are not conductively connected.

In the configuration shown in FIG. 22, conductive windings 2206 are configured to generate one of the components (e.g., the Bz' component) of the compensation magnetic field used to actively shield magnetometers 106 from ambient background magnetic fields. Such conductive windings may be implemented by two half-coils and/or in any other suitable manner. Other conductive winding configurations may be driven over coaxial cables in any suitable manner.

Use of twisted pair cables to interface with magnetometers 106 and coaxial cables to interface with magnetic field generator 108 is beneficial for a number of reasons. For example, intended operation of a magnetometer, such as an OPM, may include a modulated drive current applied to conductive windings, resulting in a modulated magnetic field, resulting in a modulated optical transmission by alkali metal atoms, resulting in modulated light intensity at the signal photodetector, resulting in modulated output of the photodetector measurement circuitry. Any alternate path for the modulation signal to couple into the photodetector measurement may degrade the quality of the magnetometer measurement. Hence, by using coaxial cables to drive magnetic field generator 108 and twisted pair cables to read the output of the signal photodetectors 606, the coupling potential of the relatively long parallel cables that carry the conductive winding drive currents and the signal photodetector signals may be minimized or eliminated.

Moreover, by using coaxial cables to drive magnetic field generator 108 with the coaxial cable shields held at a constant electric potential, the electric field external to the coaxial cables is not affected by the modulation signal inside the coaxial cables. The result is that the twisted pair cable used to read the output of the signal photodetectors 606 will not be affected by the modulation signal.

Furthermore, by using coaxial cables to drive magnetic field generator 108, no magnetic fields are generated by signals carried by the coaxial cables that would interfere with the operation of magnetometers 106. The twisted pair cables that interface with the magnetometers 106 may generate magnetic fields, but because the signals on the twisted pair cables are alternating current (AC), the resultant magnetic fields generated by the twisted pair cables are at a relatively high frequency that is out of the sensitivity range of magnetometers 106. Moreover, although coaxial cables are susceptible to environmental noise, such environmental noise is rejected by twisted pair cables. Hence, crosstalk between the coaxial and twisted pair cables may be minimized or prevented.

Referring again to FIG. 19, connection interface 1904 and connection interface 1908 may alternatively be implemented by one or more twisted pair interface assemblies. In these alternative configurations, communication link 112 may be implemented by one or more twisted pair cables each configured to electrically connect specific components of magnetic field generator 108 with specific components of controller 104. In these alternative configurations, magnetic field generator 108 may be driven by controller 104 in a balanced manner so that the common mode voltage on the twisted pair cables are minimized. Moreover, in this configuration, electrical coupling from the twisted pairs of wires that are used to drive magnetic field generator 108 to the twisted pairs of wires that are used to read signal photodetectors 608 may not result in the modulation signal being measured on the signal photodetectors 608. However, for illustrative purposes, it will be assumed in the examples provided herein that connection interface 1904 and connection interface 1908 are each implemented by one or more coaxial cable interface assemblies.

Figure 23:
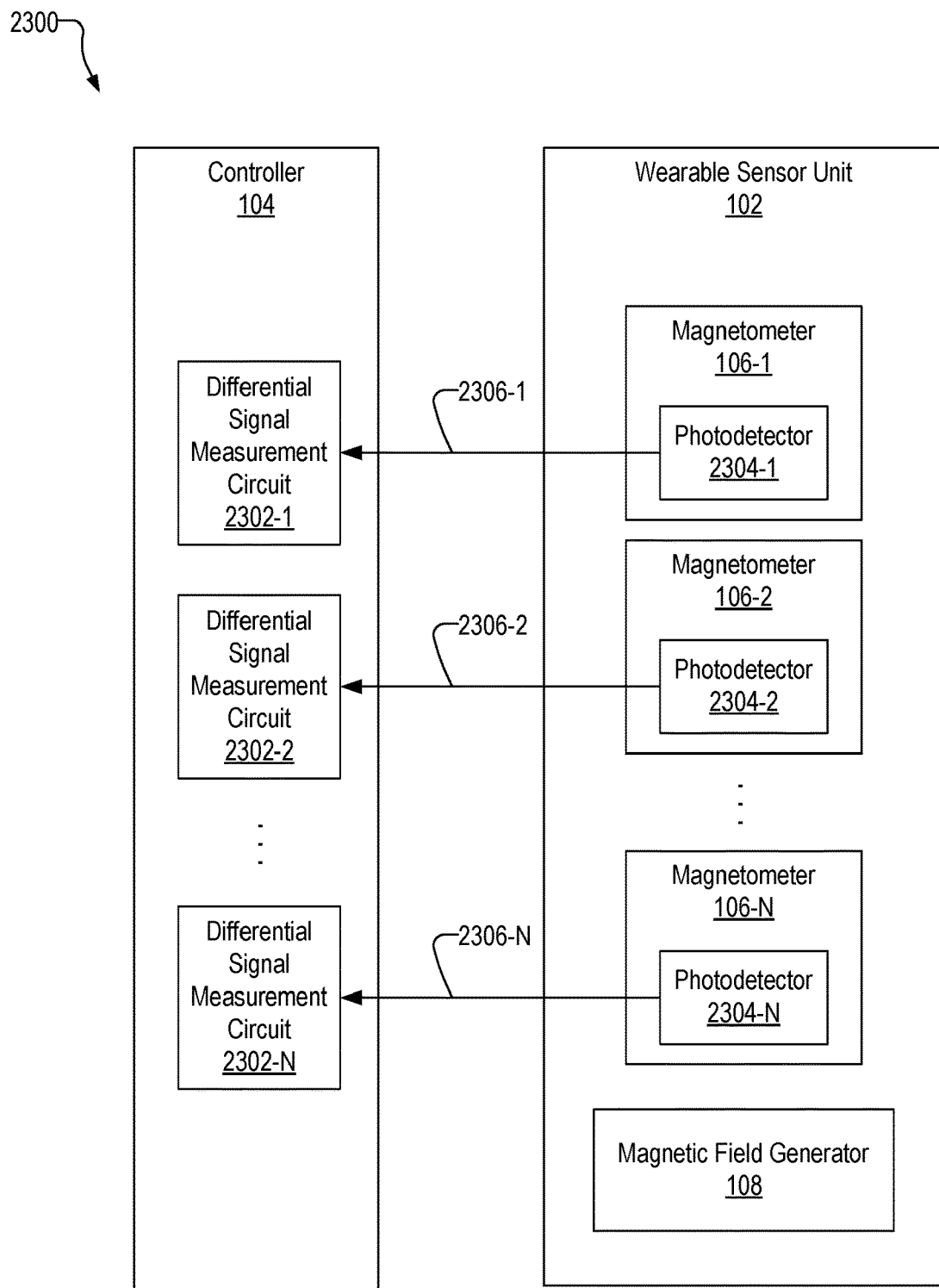
FIG. 23 illustrates an exemplary configuration in which a controller includes a plurality of differential signal measurement circuits according to principles described herein.

Exemplary manners in which controller 104 may measure current output by one or more photodetectors included in wearable sensor unit 102 will now be described. FIG. 23 illustrates an exemplary configuration 2300 in which controller 104 includes a plurality of differential signal measurement circuits 2302 (e.g., differential signal measurement circuits 2302-1 through 2302-N) configured to measure current output by photodetectors 2304 (e.g., photodetectors 2304-1 through 2304-N) included in magnetometers 106 (e.g., magnetometers 106-1 through 106-N). Differential signal measurement circuits 2302 may be included, for example, on one or more PCBs included in a housing of controller 104.

In configuration 2300, photodetectors 2304 may each be implemented by a signal photodetector (e.g., signal photodetector 606) or by a monitor photodetector (e.g., monitor photodetectors 2008). As described herein, a signal photodetector is configured to detect light output by a light source (e.g., light source 602) in a magnetometer after the light enters and exits (e.g., by passing through) a vapor cell (e.g., vapor cell 604) of the magnetometer. A monitor photodetector is configured to detect the light output by the light source before the light enters the vapor cell.

In configurations where magnetometers 106 each include a signal photodetector and a monitor photodetector, controller 104 may include a different differential signal measurement circuit 2302 for each of the photodetectors. For example, if wearable sensor unit 102 includes an array of twenty-five magnetometers 106 each having a signal photodetector and a monitor photodetector, controller 104 may include twenty-five differential signal measurement circuits 2302 for the twenty-five signal photodetectors and twenty-five differential signal measurement circuits 2302 for the twenty-five monitor photodetectors.

As shown in FIG. 23, differential signal measurement circuits 2302 may each be electrically connected to the output of its corresponding photodetector 2304 by way of a communication link 2306. For example, differential signal measurement circuit 2302-1 is electrically connected to the output of photodetector 2304-1 by way of communication link 2306-1, differential signal measurement circuit 2302-1 is electrically connected to the output of photodetector 2304-2 by way of communication link 2306-2, and differential signal measurement circuit 2302-N is electrically connected to the output of photodetector 2304-N by way of communication link 2306-N. In some examples, communication links 2306 are each implemented by twisted pairs of wires. The twisted pairs of wires may be included in one or more twisted pair cables, as described herein.

Differential signal measurement circuits 2302 may each be implemented in any suitable manner. For example, differential signal measurement circuits 2302 may each be implemented by a differential transimpedance amplifier (TIA) circuit.

Figure 24:
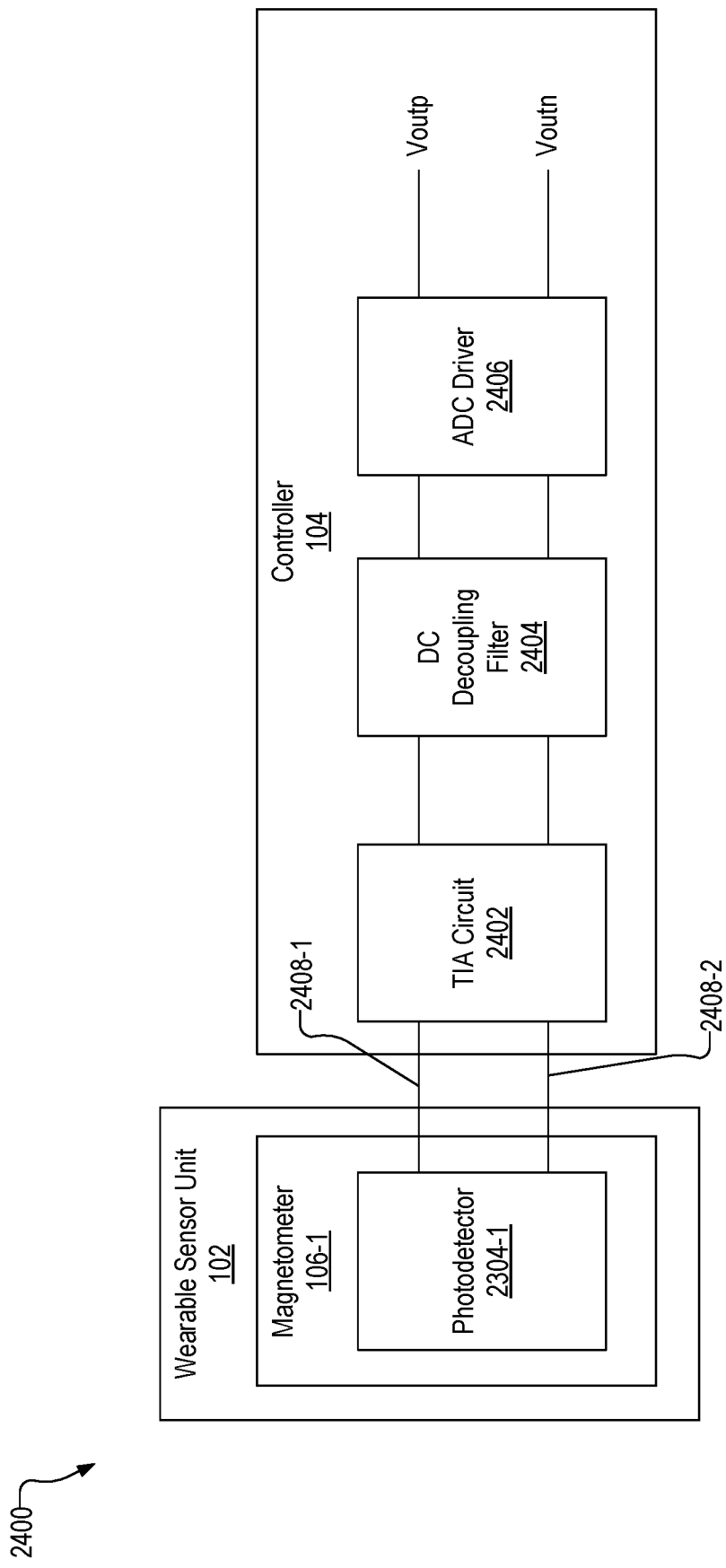
FIG. 24 shows an exemplary configuration in which a controller includes circuitry configured to measure current output by photodetector according to principles described herein.

To illustrate, FIG. 24 shows an exemplary configuration 2400 in which controller 104 includes circuitry configured to measure current output by photodetector 2304-1. As shown, the circuitry includes a TIA circuit 2402, a DC decoupling filter 2404, and an analog-to-digital (ADC) driver 2406.

TIA circuit 2402 is connected to photodetector 2304-1 by way of a twisted pair of wires 2408-1 and 2408-2. TIA circuit 2402 is configured to measure a difference between current coming in to TIA circuit 2402 on wire 2408-1 and current going out from TIA circuit 2402 on wire 2408-2. TIA circuit 2402 may be implemented by any suitable combination of electronic components and is merely illustrative of the many different manners in which differential signal measurement circuits 2302 may be implemented.

DC decoupling filter 2404 may be implemented in any suitable manner and may be configured to perform one or more DC decoupling filtering operations as may serve a particular implementation. ADC driver 2406 may be implemented in any suitable manner and may be configured to output voltages Voutp and Voutn, which may be used to drive an ADC that outputs a digital representation of the current measured by TIA circuit 2402.

By measuring a difference between current coming in to TIA circuit 2402 on wire 2408-1 and current going out from TIA circuit 2402 on wire 2408-2, TIA circuit 2402 (or, alternatively, any other implementation of differential signal measurement circuits 2302) may minimize or eliminate an effect of environmental noise (e.g., noise currents induced by external electrical fields) that may couple onto the twisted pair of wires 2408. This is because such noise couples equally into both sides of TIA circuit 2402 due to matched input impedances of the TIA circuit 2402. Hence, when the difference between the currents on wires 2408-1 and 2408-2 is measured, the noise shows up as a common mode signal and is rejected.

Because of this, a cable (e.g., a twisted pair cable) used to connect photodetectors 2304 to differential signal measurement circuits 2302 does not need to be shielded to prevent environmental noise from being coupled into the cable. By not having to shield the cable, the cable may be less thick and/or more flexible compared to a shielded cable, which is beneficial to a user of the wearable sensor unit 102. Hence, in some configurations, one or more cables (e.g., twisted pair cables) used to electrically connect controller 104 to wearable sensor unit 102 are unshielded.

In some examples, interfacing by controller 104 with various components of wearable sensor unit 102 is performed using AC instead of direct current (DC). This may prevent magnetic fields generated by DC from interfering with an operation of magnetometers 106. Although AC also generates magnetic fields, these magnetic fields are at a relatively high frequency (e.g., 200 kHz) and therefore do not affect the operation of magnetometers 106, which, in some examples, are only sensitive up to a couple hundred Hertz.

Figure 25:
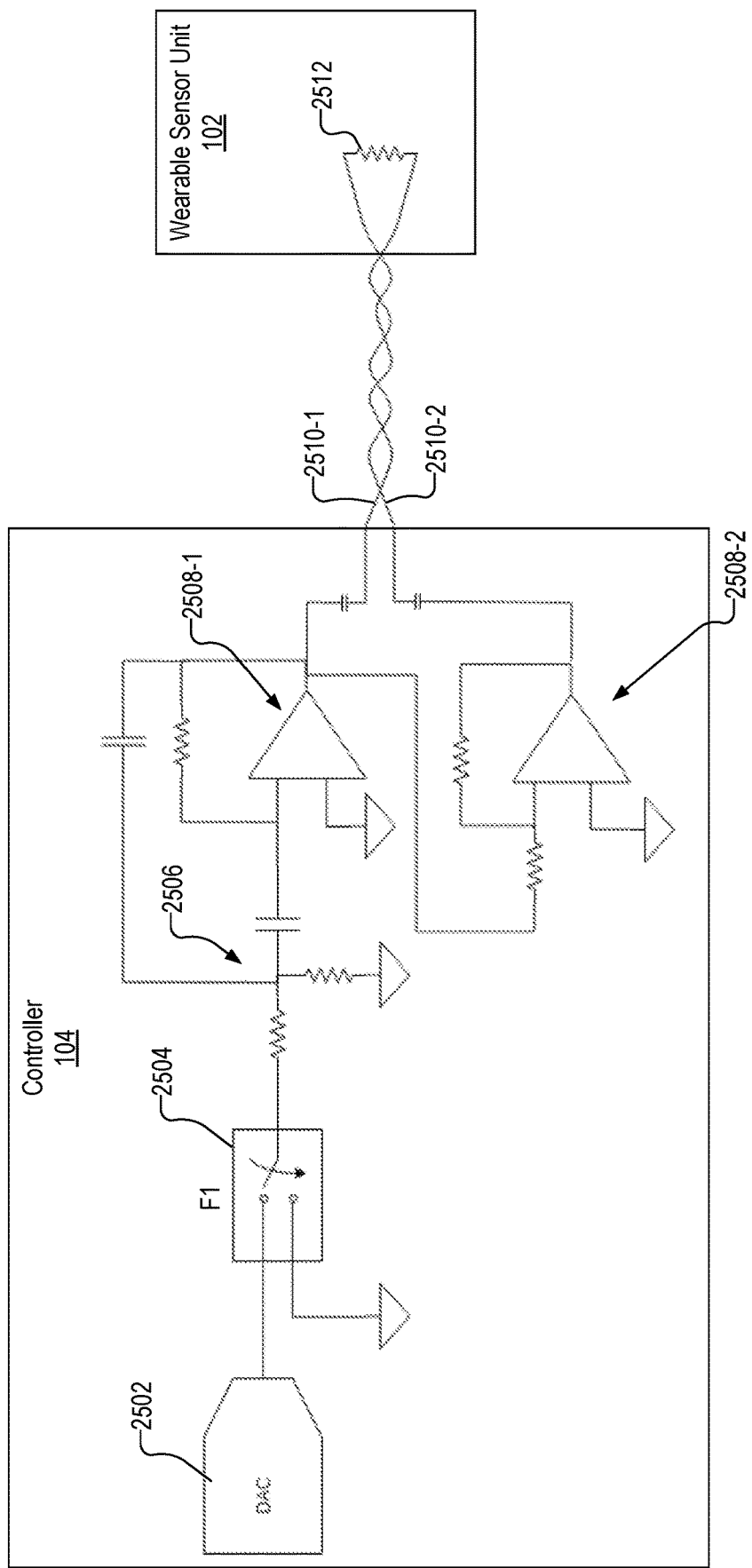
FIG. 25 shows exemplary circuitry that may be included in a controller and used to supply a drive current to a heater included in a wearable sensor unit according to principles described herein.

For example, controller 104 may be configured to supply AC drive current to light source 602, heater 2004, and/or heater 608. To illustrate, FIG. 25 shows exemplary circuitry that may be included in controller 104 and used to supply a drive current to a heater (e.g., heater 2004 or heater 608) included in wearable sensor unit 102. As shown, a DC DAC 2502 creates a DC control voltage proportional to the amount of heat that is to be produced by the heater. A square wave generator 2504 (e.g., a switch) chops the control voltage at a frequency F1 (which may be any suitable frequency) to create an AC voltage. A bandpass filter 2506 removes higher order harmonics from the AC voltage. An amplifier circuit 2508-1 uses the AC voltage to drive a first wire 2510-1 of a twisted pair of wires that interconnects controller 104 and a chip resistor 2512 included in wearable sensor unit 102 and connected to the heater. An inverting amplifier 2508-2 uses the AC voltage to drive a second wire 2510-2 of the twisted pair of wires. In this manner, the chip resistor 2512 and the heater may be driven with a desired amount of AC.

Controller 104 may also be configured to use AC to detect current output by various components of wearable sensor unit 102. For example, controller 104 may use AC to detect current output by thermistor 2006, monitor photodetector 2008, and/or signal photodetector 606. To illustrate, to read the output of thermistor 2006, controller 104 may be configured to drive an AC voltage through a Wheatstone Bridge (or any other suitable circuitry) and measure a resulting voltage across thermistor 2006.

Additionally, to minimize magnetic field spread, the physical area enclosed by an outgoing current line and a return current line on a printed circuit board (e.g., a printed circuit board that includes light sources and/or photodetectors) may be designed to be less than a threshold amount (e.g., the distance between the two current lines may be less than 2 mm).

Figure 26:
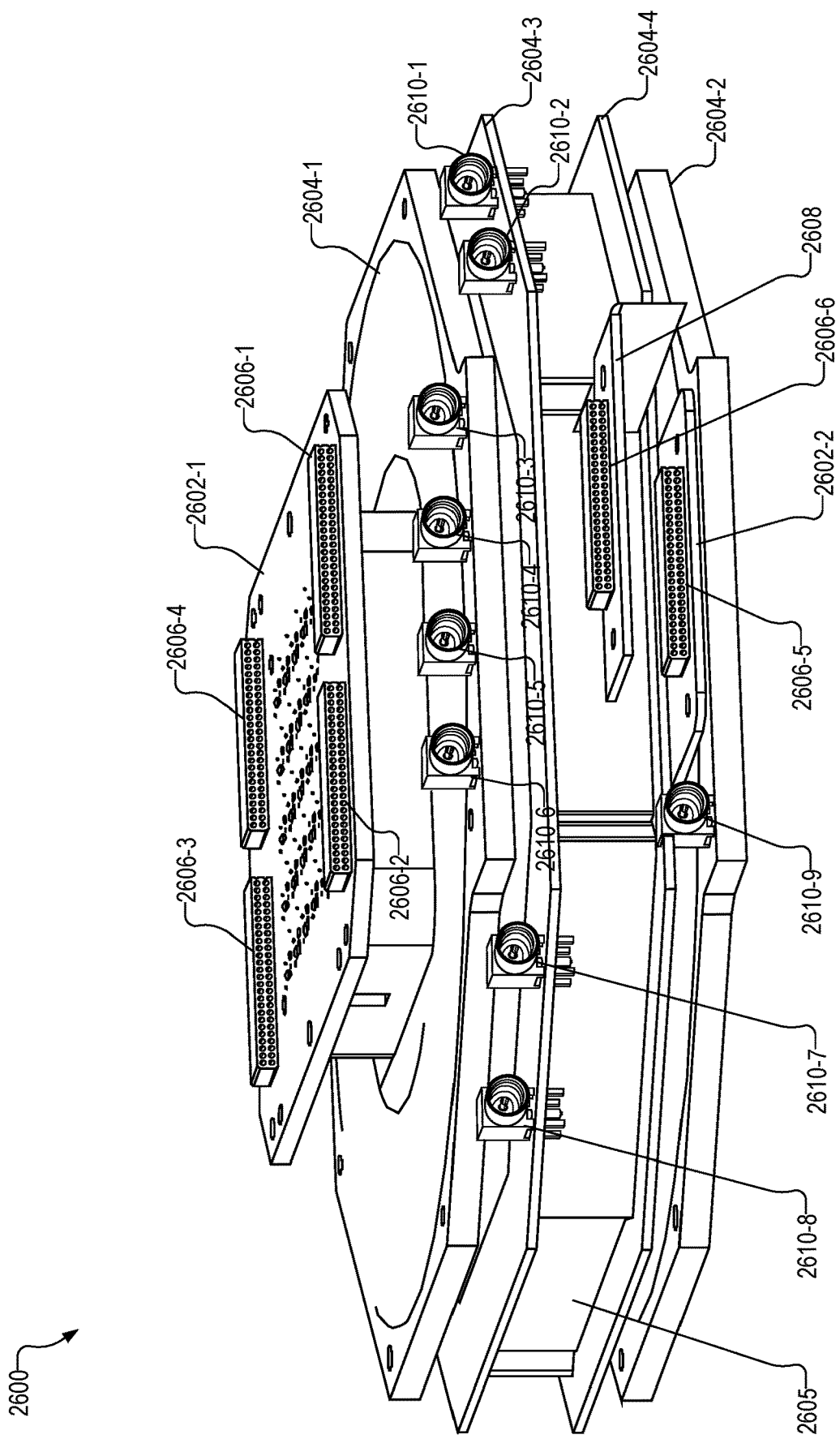
FIG. 26 shows a perspective view of an exemplary physical implementation of a wearable sensor unit according to principles described herein.

FIG. 26 shows a perspective view of an exemplary physical implementation 2600 of wearable sensor unit 102. As shown, physical implementation 2600 includes PCBs 2602-1 and 2602-2 (collectively "PCBs 2602") and substrates 2604-1 through 2604-4 (collectively "substrates 2604"). In some examples, substrates 2604 may be implemented by PCBs.

PCBs 2602 and substrates 2604 are structurally arranged as shown. In particular, PCB 2602 is located at a "top" side of physical implementation 2600 (i.e., a side furthest away from a head or other surface upon which wearable sensor unit 102 is placed to detect magnetic fields) and substrate 2604-2 is located at a "bottom" side of physical implementation 2600 (i.e., a side closest to a head or other surface upon which wearable sensor unit 102 is placed to detect magnetic fields).

Interconnect 2605 is disposed between substrates 2604-3 and 2604-5 and maintains a spacing between substrates 2604-3 and 2604-5. A magnetic field sensing region (not shown in FIG. 26) is located between substrates 2604-3 and 2604-5 and surrounded by interconnect 2605. An array of vapor cells (not shown) is located within the magnetic field sensing region.

Conductive windings that constitute magnetic field generator 108 are disposed on substrates 2604. For example, conductive windings configured to generate the Bz' component of the compensation magnetic field may be disposed on substrates 2604-1 and 2604-2. Conductive windings configured to generate the Bx' and By' components of the compensation magnetic field include wiring sets disposed on substrates 2604-3 and 2604-4 and conductive elements in interconnect 2605. Conductive windings configured to generate gradient components of the compensation magnetic field may additionally be disposed on substrates 2604-1 through 2604-4 and in interconnect 2605.

PCB 2602-1 includes various components disposed thereon that are associated with light sources included in each magnetometer 106. For example, PCB 2602-1 may include light sources (e.g., light source 602), heaters (e.g., heater 2004) for the light sources, thermistors (e.g., thermistor 2006) for the light sources, and monitor photodetectors (e.g., monitor photodetector 2008) disposed thereon. As shown, PCB 2602-1 may also include a plurality of twisted pair cable interface assemblies 2606 disposed thereon. In particular, twisted pair cable interface assembly 2606-1 is electrically connected to inputs of the light sources, twisted pair cable interface 2606-2 is electrically connected to inputs of the heaters, twisted pair cable interface 2606-3 is electrically connected to outputs of the thermistors, and twisted pair cable interface 2606-4 is electrically connected to outputs of the monitor photodetectors.

PCB 2602-2 may include signal photodetectors (e.g., signal photodetector 606) and a twisted pair cable interface 2606-5 electrically connected to outputs of the signal photodetectors. A twisted pair cable interface 2606-6 electrically connected to inputs of heaters (e.g., heater 608) for the signal photodetectors is disposed on a mount 2608 located proximate to PCB 2602-2.

As shown, coaxial cable interface assemblies 2610-1 through 2610-9 (collectively "coaxial cable interface assemblies 2610") are located on substrates 2604. Coaxial cable interface assemblies 2610 are conductively coupled to the conductive windings that constitute magnetic field generator 108. As described herein, controller 104 may drive the conductive windings by supplying drive current to the conductive windings by way of coaxial cables connected to coaxial cable interface assemblies 2610.

Physical implementation 2600 may include any additional or alternative components as may suit a particular implementation (e.g., a housing to house at least some of the components shown in FIG. 26, support structures to support substrates 2604, etc.).

Figure 27:
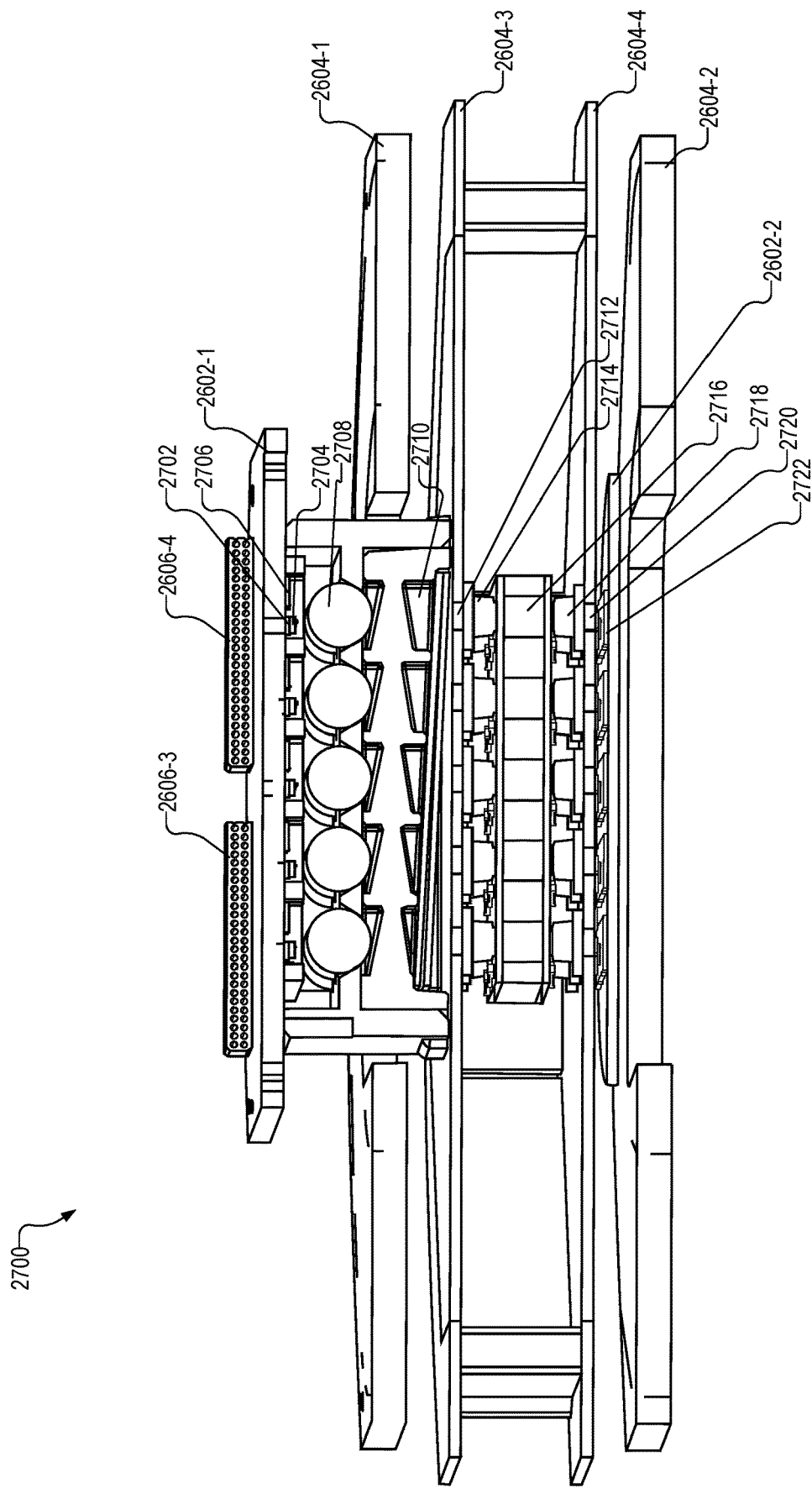
FIG. 27 shows a cross sectional side view of the physical implementation of FIG. 26 according to principles described herein.

FIG. 27 shows a cross sectional side view of physical implementation 2600 of wearable sensor unit 102 and illustrates various components of magnetometers 106 that are located within wearable sensor unit 102.

For example, FIG. 27 shows that a plurality of light sources (e.g., light source 2702, which may implement any of the light sources described herein), a plurality of thermistors (e.g., thermistor 2704, which may implement any of the thermistors described herein), and a plurality of monitor photodetectors (e.g., monitor photodetector 2706, which may implement any of the monitor photodetectors described herein) are disposed on an underneath side of PCB 2602-1.

Light generated by light sources is collimated by a plurality of collimating lenses (e.g., collimating lens 2708) and passes through optics (e.g., optics 2710). Optics may include, for example, a prism for each magnetometer that is configured to reflect the light onto the monitor photodiodes. The light also passes through the optics, then through holes (e.g., hole 2712) in substrate 2604-3, then through chimneys (e.g., chimney 2714), and into vapor cells (e.g., vapor cell 2716, which may implement any of the vapor cells described herein). The chimneys are configured to prevent heat from the vapor cells from going back up through the holes.

In the implementation of FIG. 27, the light from the light sources passes through the vapor cells, then through a second set of chimneys (e.g., chimney 2718), and then through holes (e.g., hole 2720) in substrate 2604-4. The light is then detected by signal photodetectors (e.g., signal photodetector 2722, which may implement any of the signal photodetectors described herein).

Figure 28:
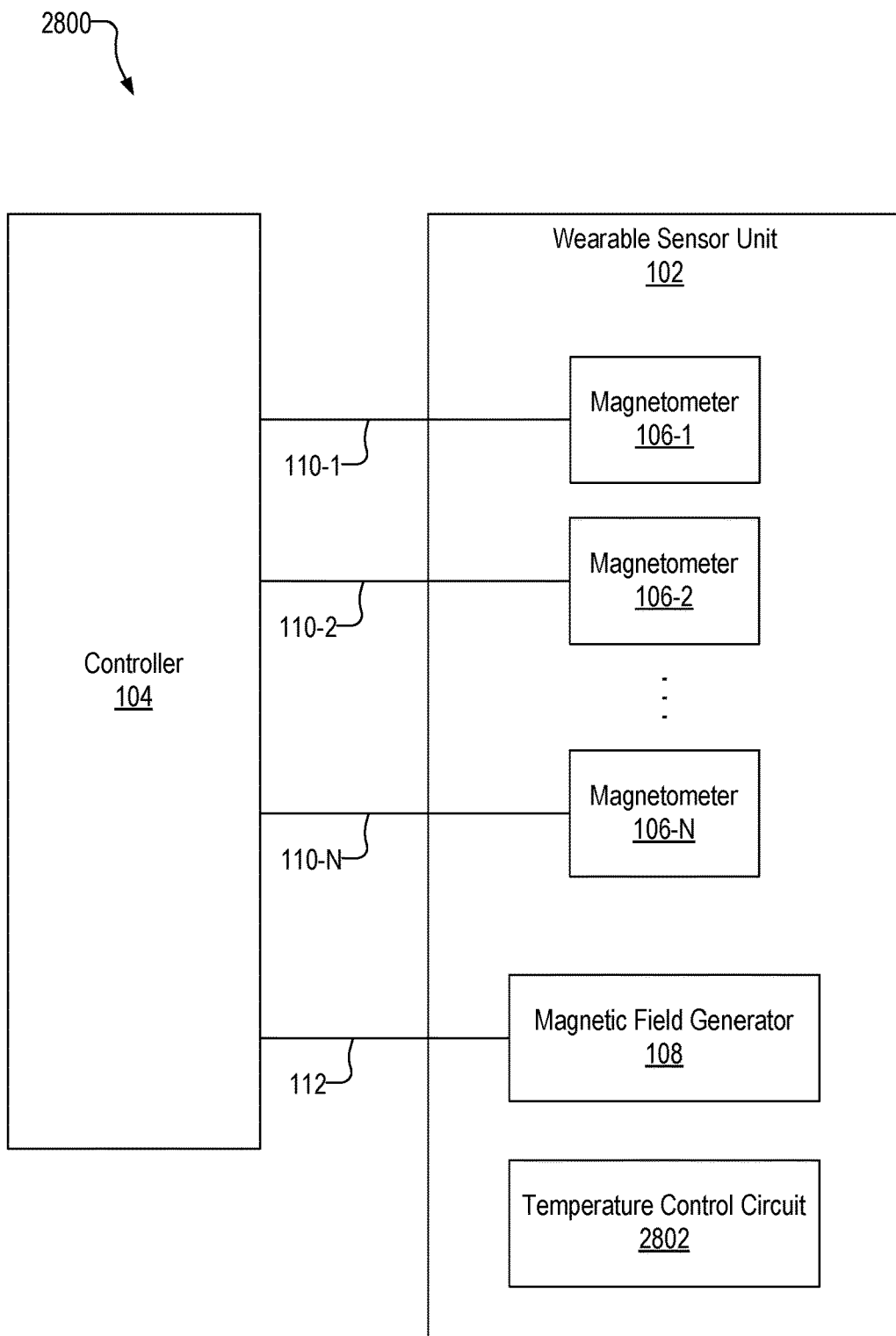
FIG. 28 shows an exemplary configuration in which a wearable sensor unit includes a temperature control circuit according to principles described herein.

FIG. 28 shows an exemplary configuration 2800 in which wearable sensor unit 102 further includes a temperature control circuit 2802. Temperature control circuit 2802 is configured to create a temperature gradient within each of the vapor cells of magnetometers 106. The temperature gradient is configured to concentrate the alkali metal within each of the vapor cells away from transit paths of light that passes into the vapor cells. As described herein, this may allow the light to properly enter and exit the vapor cells and then be detected by signal photodetectors. In some examples, controller 104 is configured to drive temperature control circuit 2802 by supplying current to temperature control circuit 2802.

Temperature control circuit 2802 may be configured to create a temperature gradient within a vapor cell in any suitable manner. For example, temperature control circuit 2802 may be configured to create the temperature gradient within the vapor cell by creating any combination of hot spots, cold spots, distributed cooling, and/or distributed heating.

To illustrate, in some examples, temperature control circuit 2802 may be configured to create a temperature gradient within a vapor cell by creating one or more hot spots on an inner surface of the vapor cell that are hotter by at least a threshold amount (e.g., a threshold number of degrees) than other locations on the inner surface of the vapor cell. In these examples, temperature control circuit 2802 may, in some embodiments, also apply distributed cooling to at least some of the other locations on the inner surface of the vapor cell and/or create one or more cold spots on the inner surface of the vapor cell that are colder by at least a threshold amount than other locations on the inner surface of the vapor cell.

In some alternative examples, temperature control circuit 2802 may be configured to create a temperature gradient within a vapor cell by creating one or more cold spots on an inner surface of the vapor cell that are colder by at least a threshold amount than other locations on the inner surface of the vapor cell. In these examples, temperature control circuit 2802 may, in some embodiments, also apply distributed heating to at least some of the other locations on the inner surface of the vapor cell and/or create one or more hot spots on the inner surface of the vapor cell that are hotter by at least an additional threshold amount than other locations on the inner surface of the vapor cell.

Figure 29:
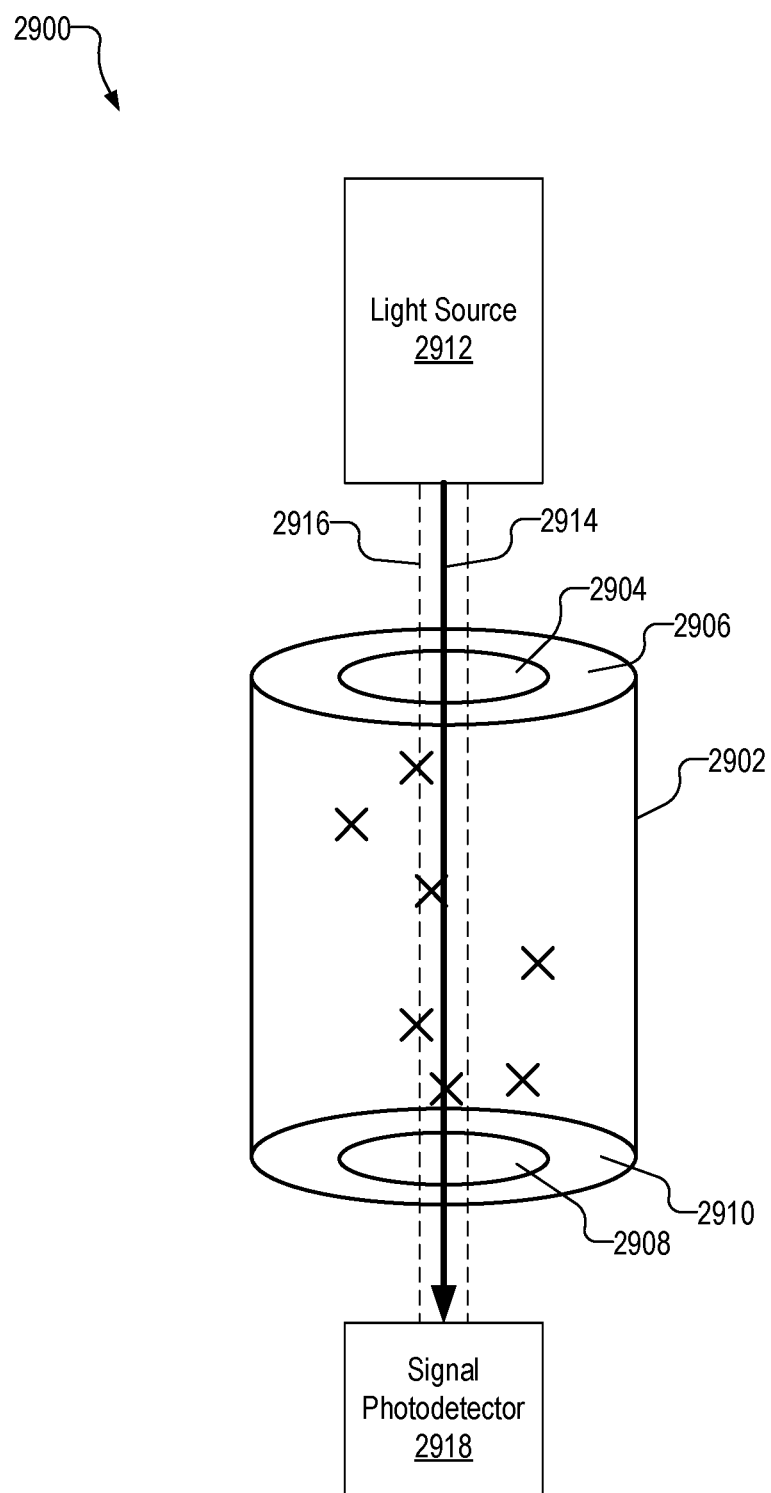
FIG. 29 shows an exemplary configuration of a vapor cell according to principles described herein.

To illustrate the benefits of creating a temperature gradient within a vapor cell, FIG. 29 shows an exemplary configuration 2900 in which a vapor cell 2902 (which may implement any of the vapor cells described herein) includes an input window 2904 on a top surface 2906 of vapor cell 2902 and an output window 2908 on a bottom surface 2910 of vapor cell 2902. Input window 2904 and output window 2908 may be made out of any suitable material that allows light to pass therethrough.

As shown, a light source 2912 (which may implement any of the light sources described herein) outputs light 2914 (e.g., a light beam) configured to enter vapor cell 2904 through input window 2904 along a transit path 2916. The light 2914 is intended to continue along transit path 2916 until it exits vapor cell 2902 through output window 2908.

The light 2914 is then detected by a signal photodetector 2918, which may implement any of the signal photodetectors described herein.

As described herein, vapor cell 2902 contains alkali metal, which is represented in FIG. 29 by a plurality of X's interspersed within vapor cell 2902. The alkali metal may have any combination of gas, liquid, and solid states, depending on temperature. In some instances during operation of the magnetometer of which vapor cell 2902 is a part, if atoms of the alkali metal are within transit path 2916, the alkali metal may potentially prevent light 2914 from properly exiting vapor cell 2902 through output window 2908.

Figure 30:
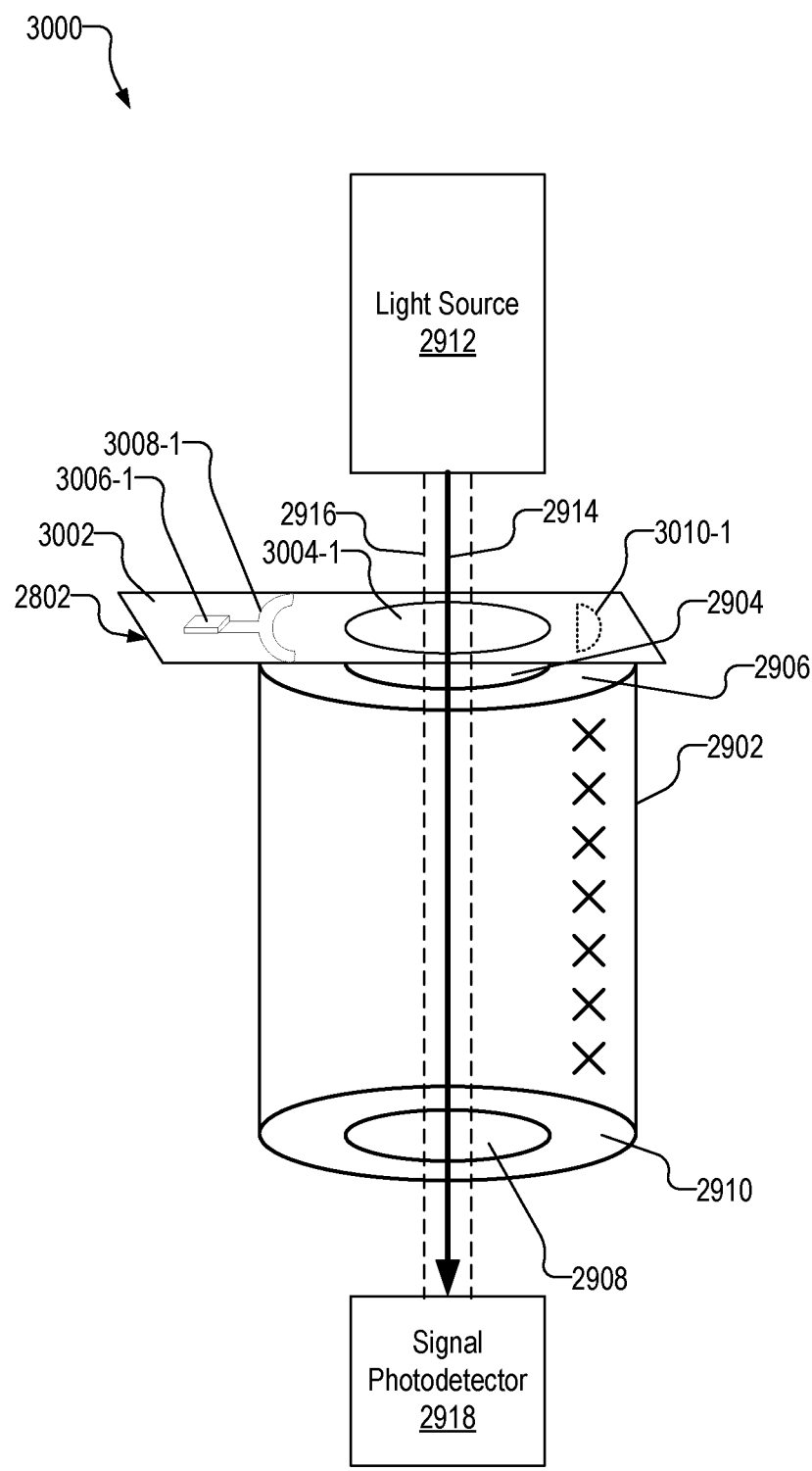
FIG. 30 shows an exemplary configuration in which a temperature control circuit creates a temperature gradient within a vapor cell according to principles described herein.

FIG. 30 shows an exemplary configuration 3000 in which temperature control circuit 2802 creates a temperature gradient within vapor cell 2902 that concentrates the alkali metal within vapor cell 2902 away from transit path 2916 of light 2914. In configuration 3000, temperature control circuit 2802 is implemented by a PCB 3002 that includes an input aperture 3004-1 configured to align with and be above input window 2904 of vapor cell 2902 such that light 2914 passes through input aperture 3004-1 before passing through input window 2904, a heat generating element 3006-1 configured to generate heat, a thermal contact 3008-1 on a first side of input aperture 3004-1 and thermally connected to heat generating element 3006-1, and a thermal path out 3010-1 on a second side of input aperture 3004-1. Heat generating element 3006-1, thermal contact 3008-1, and thermal path out 3010-1 have dashed lines in FIG. 30 to connote that they may be disposed on an underneath side of PCB 3002.

Heat generating element 3006-1 may be implemented by one or more electrical components configured to generated heat when driven with a current by controller 104. For example, heat generating element 3006-1 may be implemented by one or more resistors.

Thermal contact 3008-1 is configured to create one or more hot spots by directing the heat from heat generating element 3006-1 to vapor cell 2902. Thermal path out 3010-1 provides a path for heat to escape and is configured to assist in creating the temperature gradient within vapor cell 2902. In some examples, PCB 3002 is positioned close enough to top surface 2906 of vapor cell 2902 that thermal contact 3008-1 and thermal path out 3010-1 are in physical contact with top surface 2906.

In configuration 3000, the temperature gradient created by one or more hot spots is configured to concentrate the alkali metal within vapor cell 2902 at the relatively colder regions within vapor cell 2902, which are closer to thermal path out 3010-1 than to thermal contact 3008-1. This is illustrated in FIG. 30 by the Xs that represent the alkali metal being concentrated on the right side of vapor cell 2902, away from transit path 2916.

Figure 31:
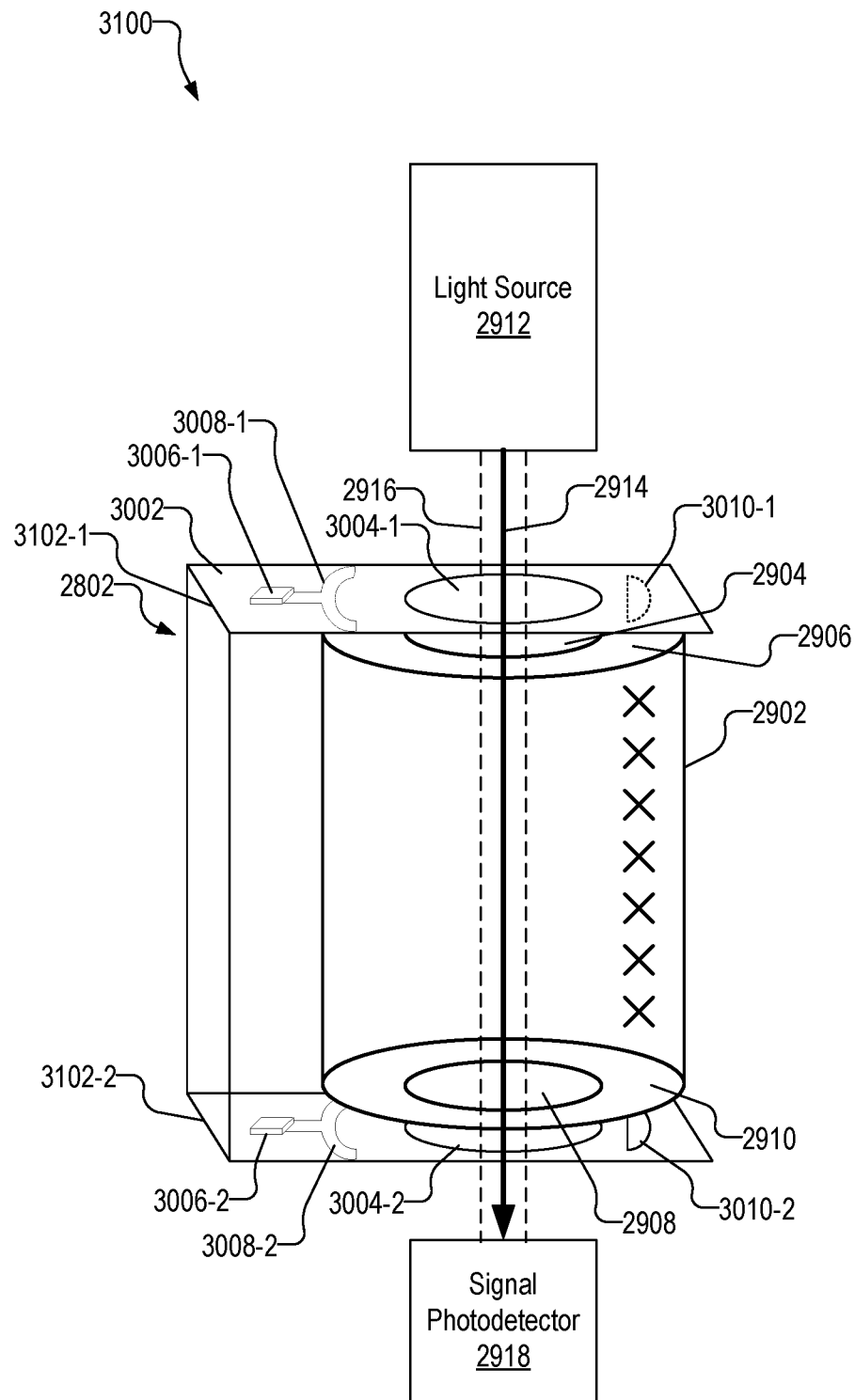
FIG. 31 illustrates another implementation of temperature control circuit according to principles described herein.

FIG. 31 illustrates another implementation 3100 of temperature control circuit 2802. In implementation 3100, PCB 3002 is flexible and configured to fold along bend lines 3102-1 and 3102-2 to surround vapor cell 2902. In this configuration, PCB 3002 further includes an output aperture 3004-2 configured to align with and be below output window 2908 of vapor cell 2902 such that light 2914 passes through output aperture 3004-2 after passing through output window 2908, a heat generating element 3006-2 configured to generate heat, a thermal contact 3008-2 on a first side of output aperture 3004-2 and thermally connected to heat generating element 3006-2, and a thermal path out 3010-2 on a second side of output aperture 3004-2.

Heat generating element 3006-2 may be implemented by one or more electrical components configured to generated heat when driven with a current by controller 104. For example, heat generating element 3006-2 may be implemented by one or more resistors. Because heat generating elements 3006-1 and 3006-2 are on the same PCB 3002, they may be driven concurrently by controller 104 with the same current.

Thermal contact 3008-2 is configured to assist in creating the one or more hot spots by directing the heat from heat generating element 3006-2 to vapor cell 2902. Thermal path out 3010-2 provides a path for heat to escape and is configured to assist in creating the temperature gradient within vapor cell 2902. In some examples, PCB 3002 is positioned close enough to bottom surface 2910 of vapor cell 2902 that thermal contact 3008-2 and thermal path out 3010-2 are in physical contact with bottom surface 2910.

Figure 32:
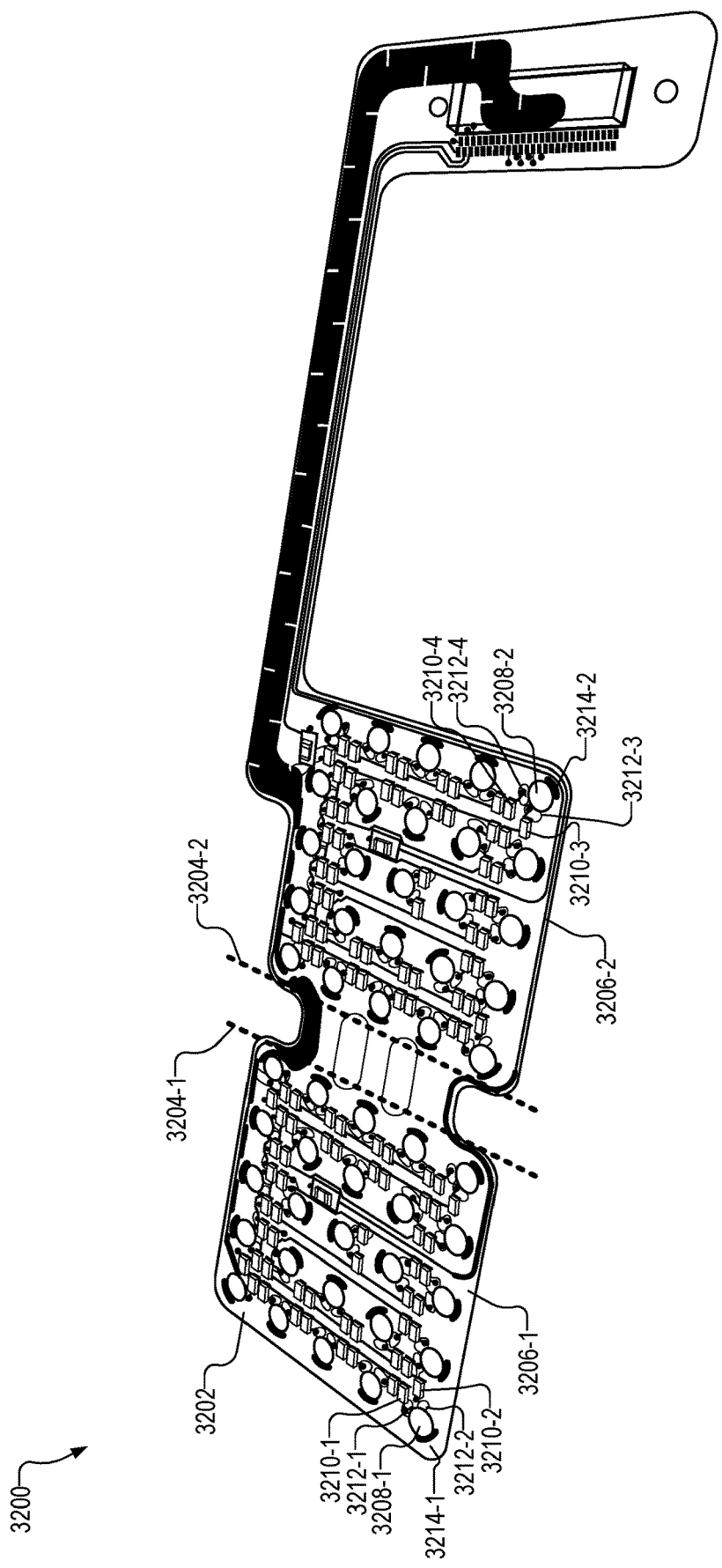
FIG. 32 is a perspective view of an exemplary implementation of a temperature control circuit according to principles described herein.

FIG. 32 is a perspective view of an exemplary flexible PCB implementation 3200 of temperature control circuit 2802 that may be used in a wearable sensor unit that includes an array of twenty-five magnetometers. As shown, implementation 3200 includes a flexible PCB 3202 configured to fold along fold lines 3204-1 and 3204-2 such that a top portion 3206-1 of flexible PCB 3202 is configured to be positioned above an array of vapor cells (e.g., an array of vapor cells similar to vapor cell 2902) and a bottom portion 3206-2 of flexible PCB 3202 is configured to be positioned below the array of vapor cells.

As shown, top portion 3206-1 of flexible PCB 3202 includes a plurality of input apertures (e.g., input aperture 3208-1), a plurality of heat generating elements (e.g., heat generating elements 3210-1 and 3210-2), a plurality of thermal contacts (e.g., thermal contacts 3212-1 and 3212-2), and a plurality of thermal paths out (e.g., thermal path out 3214-1). Likewise, bottom portion 3206-2 of flexible PCB 3202 includes a plurality of output apertures (e.g., output aperture 3208-2), a plurality of heat generating elements (e.g., heat generating elements 3210-3 and 3210-4), a plurality of thermal contacts (e.g., thermal contacts 3212-3 and 3212-4), and a plurality of thermal paths out (e.g., thermal path out 3214-2).

While flexible PCB 3202 is in the folded position, elements on top portion 3206-1 of flexible PCB 3202 corresponding to elements on bottom portion 3206-2 of flexible PCB 3202 may align with each other and with individual vapor cells included the array of vapor cells. For example, while flexible PCB 3202 is in the folded position, input aperture 3208-1 and output aperture 3208-2 are configured to be aligned with input and output windows of a particular vapor cell.

While flexible PCBs used to implement temperature control circuit 2802 are shown in FIGS. 31 and 32, in alternative implementations, separate PCBs with heating and/or cooling elements may be located above and beneath the vapor cells of wearable sensor unit 102.

Figure 33:
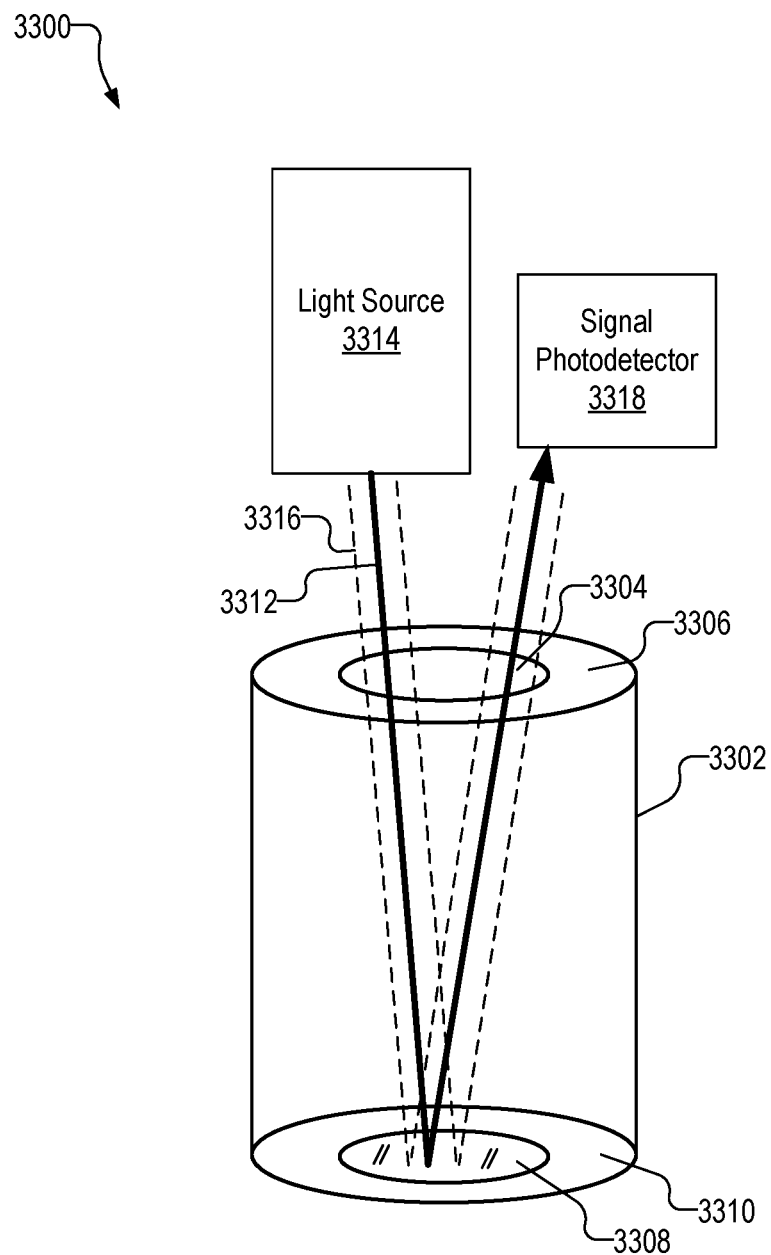
FIG. 33 illustrates a configuration in which a vapor cell includes a reflecting element according to principles described herein.

FIG. 33 illustrates an alternative configuration 3300 in which a vapor cell 3302 does not include an output window on a bottom surface of the vapor cell 3302. Instead, as shown, vapor cell 3302 includes a single window 3304 on a top surface 3306. A reflecting element 3308 (e.g., a mirror) is located on a bottom surface 3310 of vapor cell 3302 (i.e., at an opposite end of vapor cell 3302 than window 3304).

In configuration 3300, light 3312 output by a light source 3314 enters vapor cell 3302 through window 3304, reflects off of reflecting element 3308, and exits vapor cell 3302 through the same window 3304. A signal photodetector 3318 may then detect reflected light 3316. The temperature control circuit 2802 described herein may be used to concentrate alkali metal within vapor cell 3302 away from a transit path 3316 of light 3312 in any of the ways described herein.

FIGS. 34-39 illustrate embodiments of a wearable device 3400 that includes elements of the wearable sensor units described herein. In particular, the wearable devices 3400 include a plurality of magnetometers 3402 and a magnetic field generator (not shown). The wearable devices 3400 may each also include a controller (e.g., controller 104) and/or be communicatively connected to a controller. In general, wearable device 3400 may be implemented by any suitable headgear and/or clothing article configured to be worn by a user. The headgear and/or clothing article may include batteries, cables, and/or other peripherals for the components of the wearable sensor units described herein.

Figure 34:
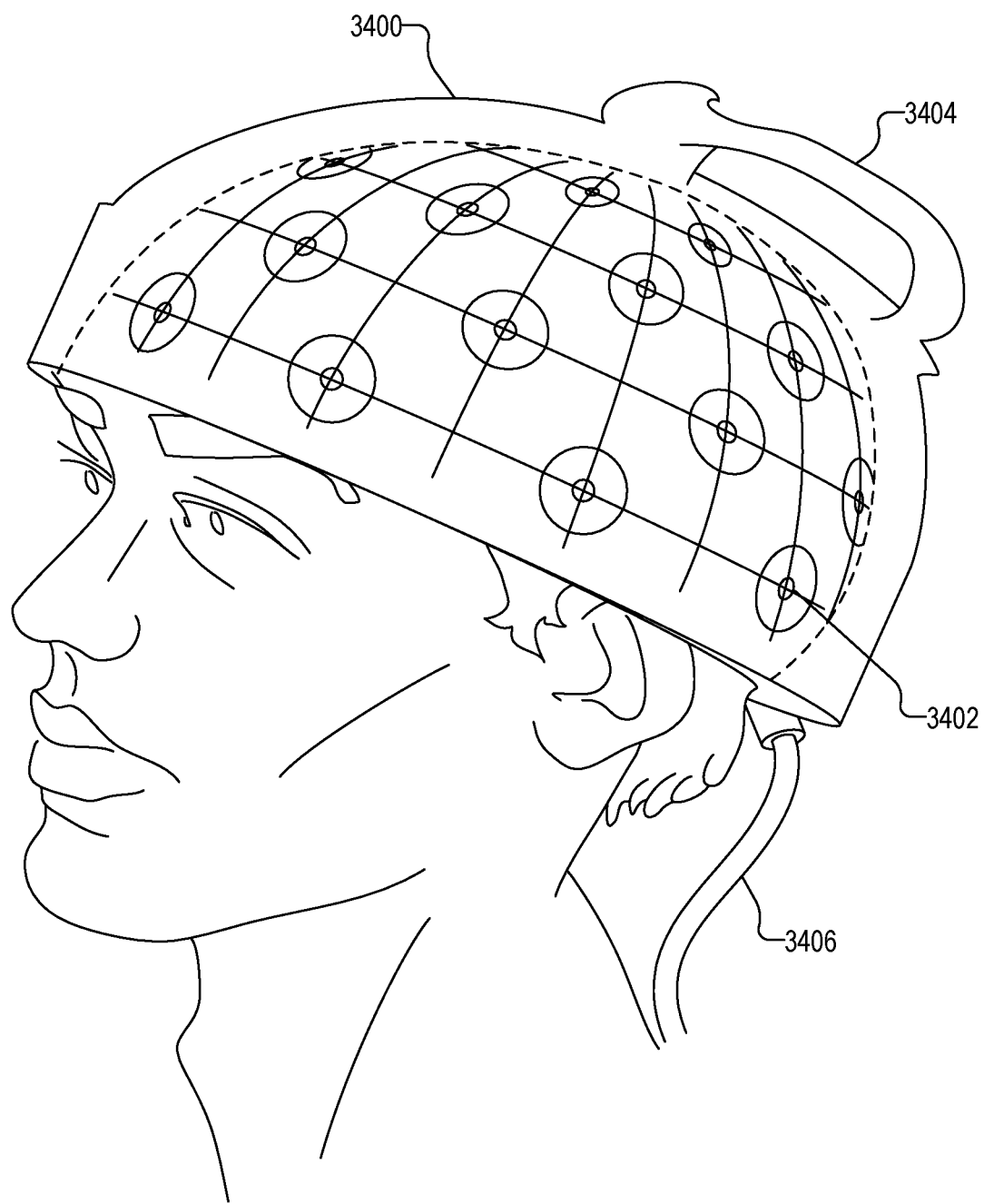
FIGS. 34-39 illustrate embodiments of a wearable device that includes elements of wearable sensor units described herein according to principles described herein.
Figure 35:
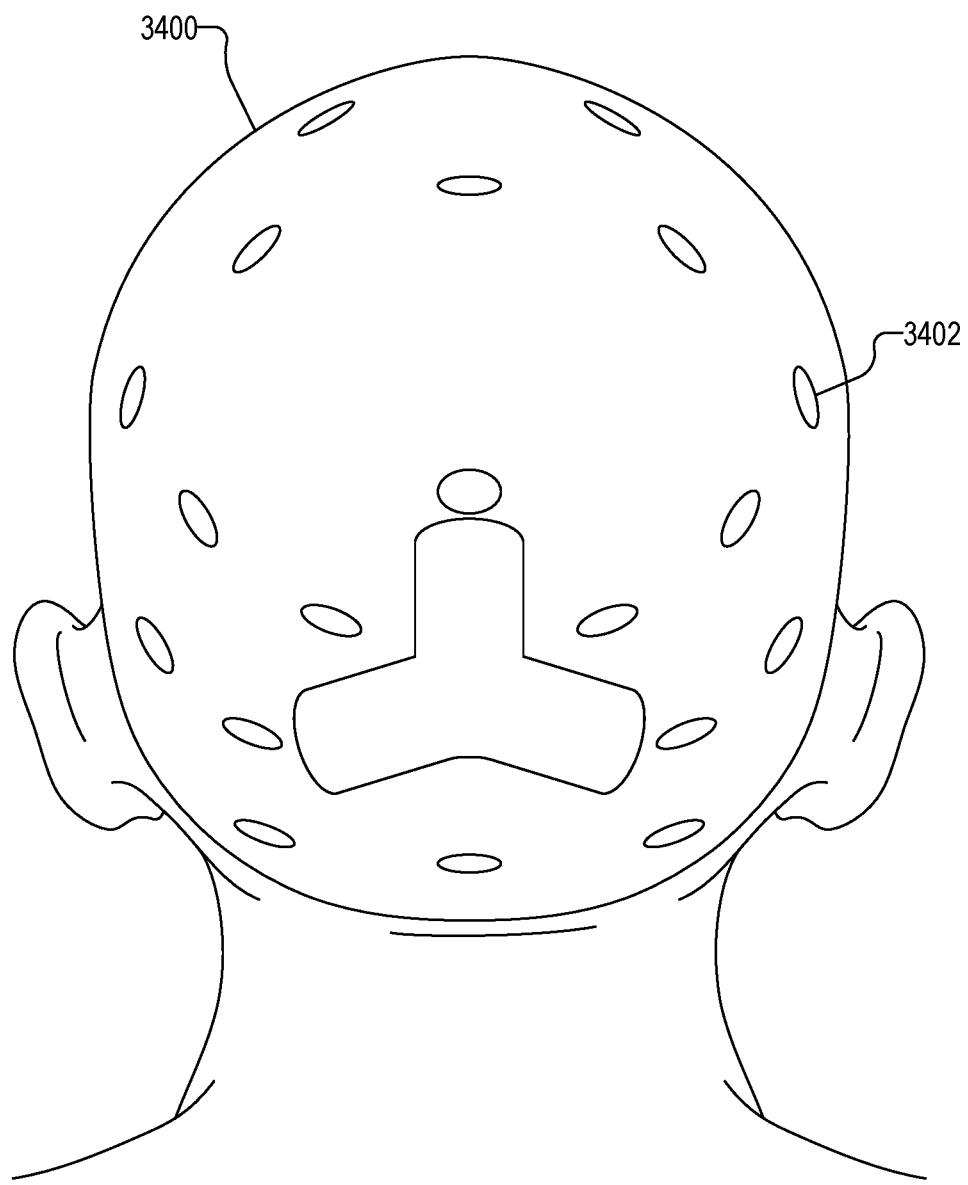
Figure 36:
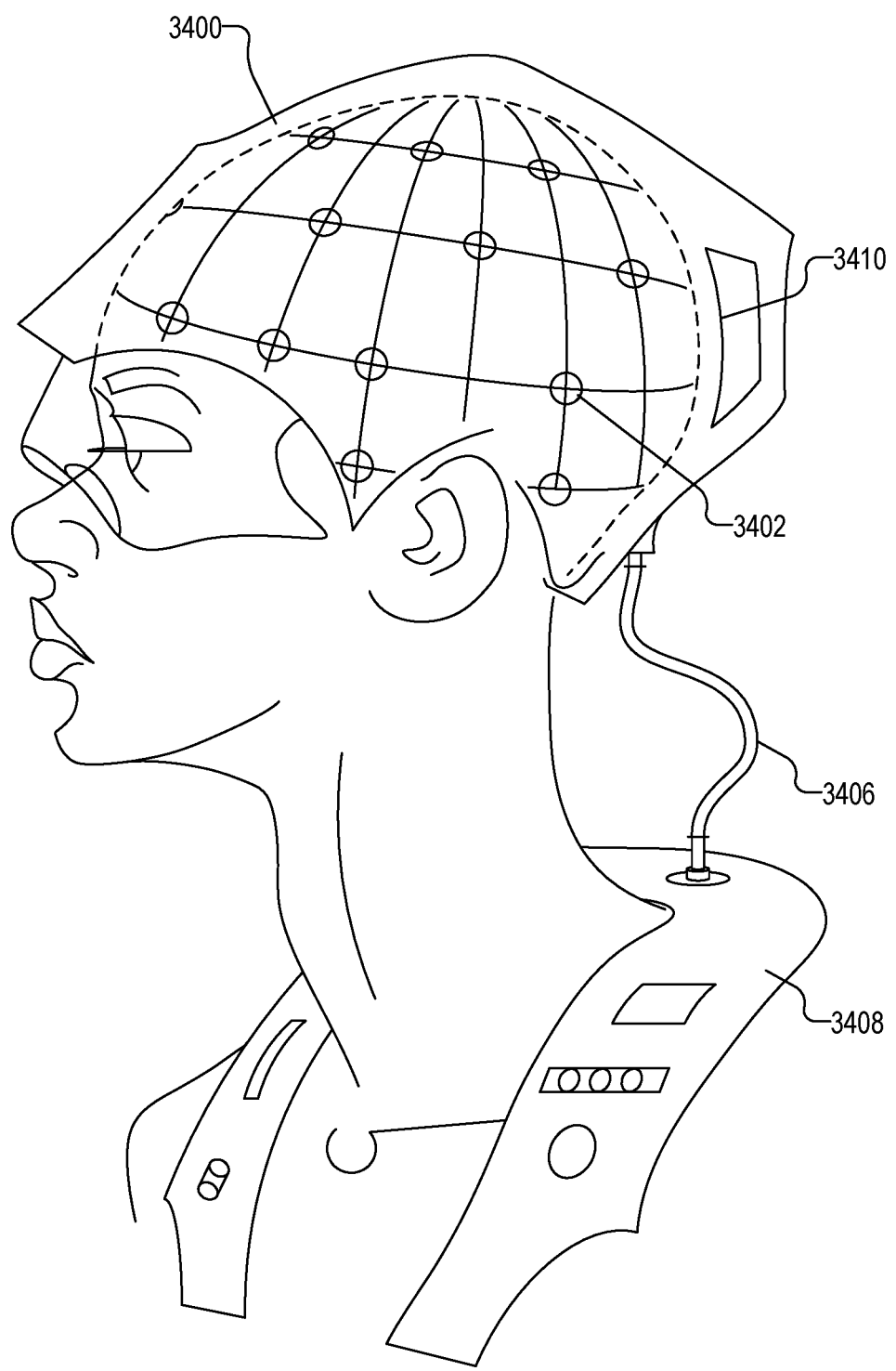

FIG. 34 illustrates an embodiment of a wearable device 3400 in the form of a helmet with a handle 3404. A cable 3406 extends from the wearable device 3400 for attachment to a battery or hub (with components such as a processor or the like). FIG. 35 illustrates another embodiment of a wearable device 3400 in the form of a helmet showing a back view. FIG. 36 illustrates a third embodiment of a wearable device 3400 in the form of a helmet with the cable 3406 leading to a wearable garment 3408 (such as a vest or partial vest) that can include a battery or a hub. Alternatively or additionally, the wearable device 3400 can include a crest 3410 or other protrusion for placement of the hub or battery.

Figure 37:
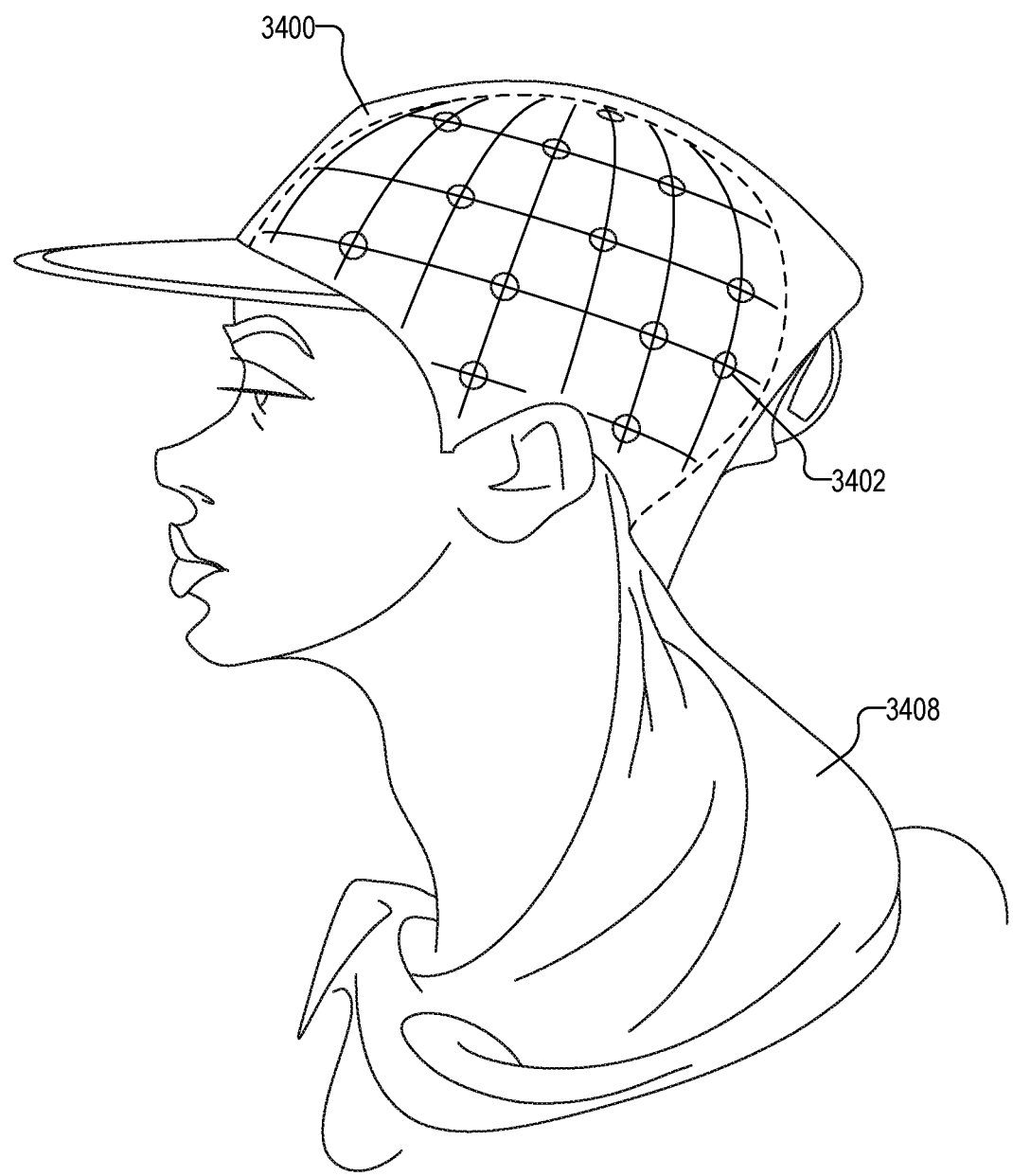
Figure 38:
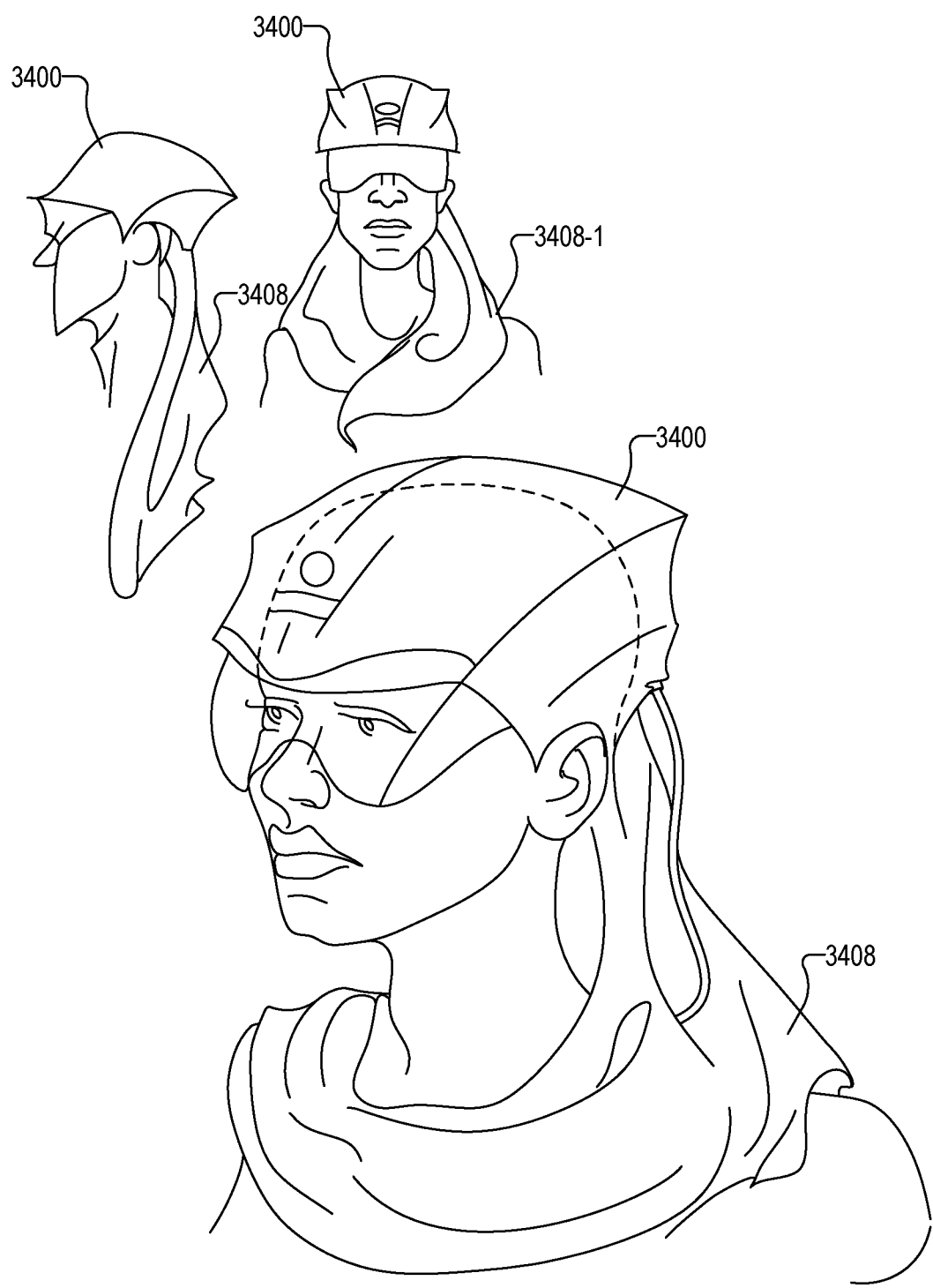
Figure 39:
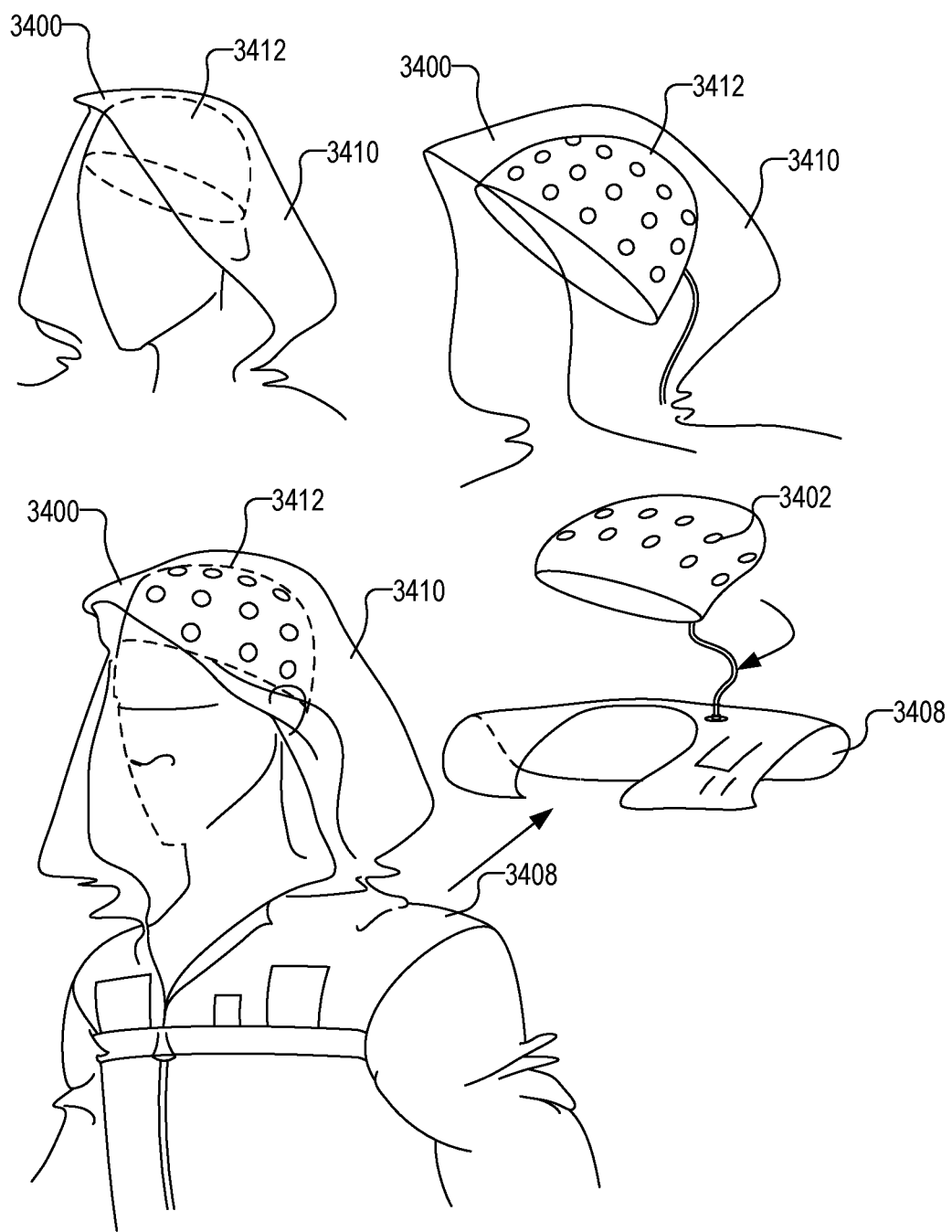

FIG. 37 illustrates another embodiment of a wearable device 3400 in the form of a cap with a wearable garment 3408 in the form of a scarf that may contain or conceal a cable, battery, and/or hub. FIG. 38 illustrates additional embodiments of a wearable device 3400 in the form of a helmet with a one-piece scarf 3408 or two-piece scarf 3408-1. FIG. 39 illustrates an embodiment of a wearable device 3400 that includes a hood 3410 and a beanie 3412 which contains the magnetometers 3402, as well as a wearable garment 3408 that may contain a battery or hub.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 40:
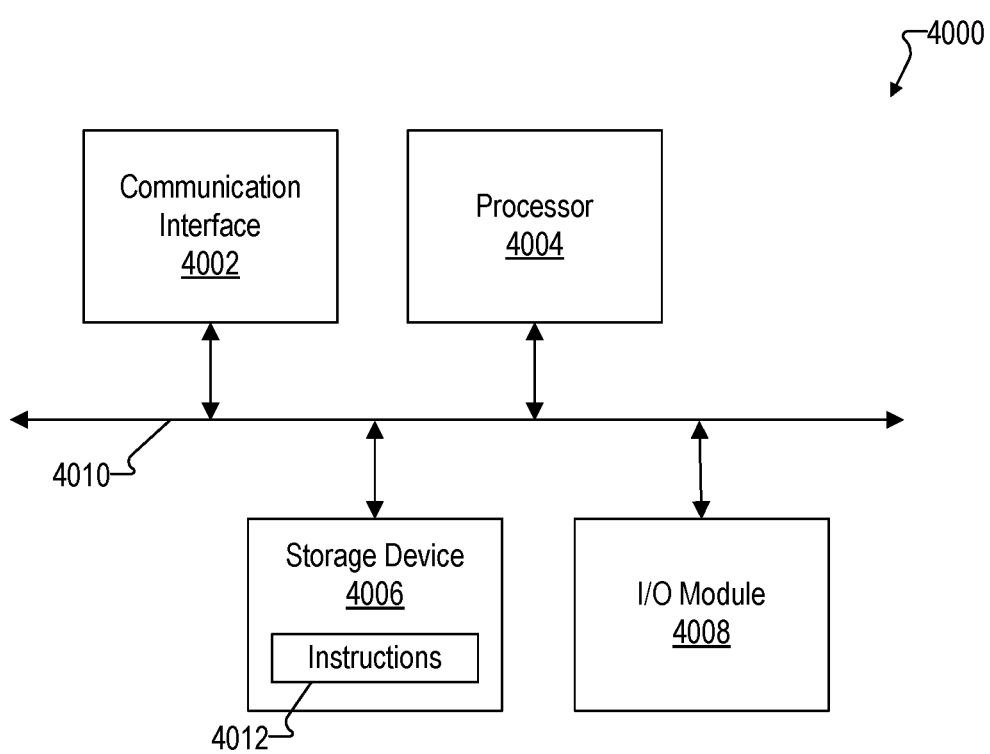
FIG. 40 illustrates an exemplary computing device according to principles described herein.

FIG. 40 illustrates an exemplary computing device 4000 that may be specifically configured to perform one or more of the processes described herein. Any of the systems, units, computing devices, and/or other components described herein may be implemented by computing device 4000.

As shown in FIG. 40, computing device 4000 may include a communication interface 4002, a processor 4004, a storage device 4006, and an input/output ("I/O") module 4008 communicatively connected one to another via a communication infrastructure 4010. While an exemplary computing device 4000 is shown in FIG. 40, the components illustrated in FIG. 40 are not intended to be limiting. Additional or alternative components may be used in other embodiments. Components of computing device 4000 shown in FIG. 40 will now be described in additional detail.

Communication interface 4002 may be configured to communicate with one or more computing devices. Examples of communication interface 4002 include, without limitation, a wired network interface (such as a network interface card), a wireless network interface (such as a wireless network interface card), a modem, an audio/video connection, and any other suitable interface.

Processor 4004 generally represents any type or form of processing unit capable of processing data and/or interpreting, executing, and/or directing execution of one or more of the instructions, processes, and/or operations described herein. Processor 4004 may perform operations by executing computer-executable instructions 4012 (e.g., an application, software, code, and/or other executable data instance) stored in storage device 4006.

Storage device 4006 may include one or more data storage media, devices, or configurations and may employ any type, form, and combination of data storage media and/or device. For example, storage device 4006 may include, but is not limited to, any combination of the non-volatile media and/or volatile media described herein. Electronic data, including data described herein, may be temporarily and/or permanently stored in storage device 4006. For example, data representative of computer-executable instructions 4012 configured to direct processor 4004 to perform any of the operations described herein may be stored within storage device 4006. In some examples, data may be arranged in one or more databases residing within storage device 4006.

I/O module 4008 may include one or more I/O modules configured to receive user input and provide user output. I/O module 4008 may include any hardware, firmware, software, or combination thereof supportive of input and output capabilities. For example, I/O module 4008 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 4008 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 4008 is configured to provide graphical data to a display for presentation to a user. The graphical data may be representative of one or more graphical user interfaces and/or any other graphical content as may serve a particular implementation.

Figure 41:
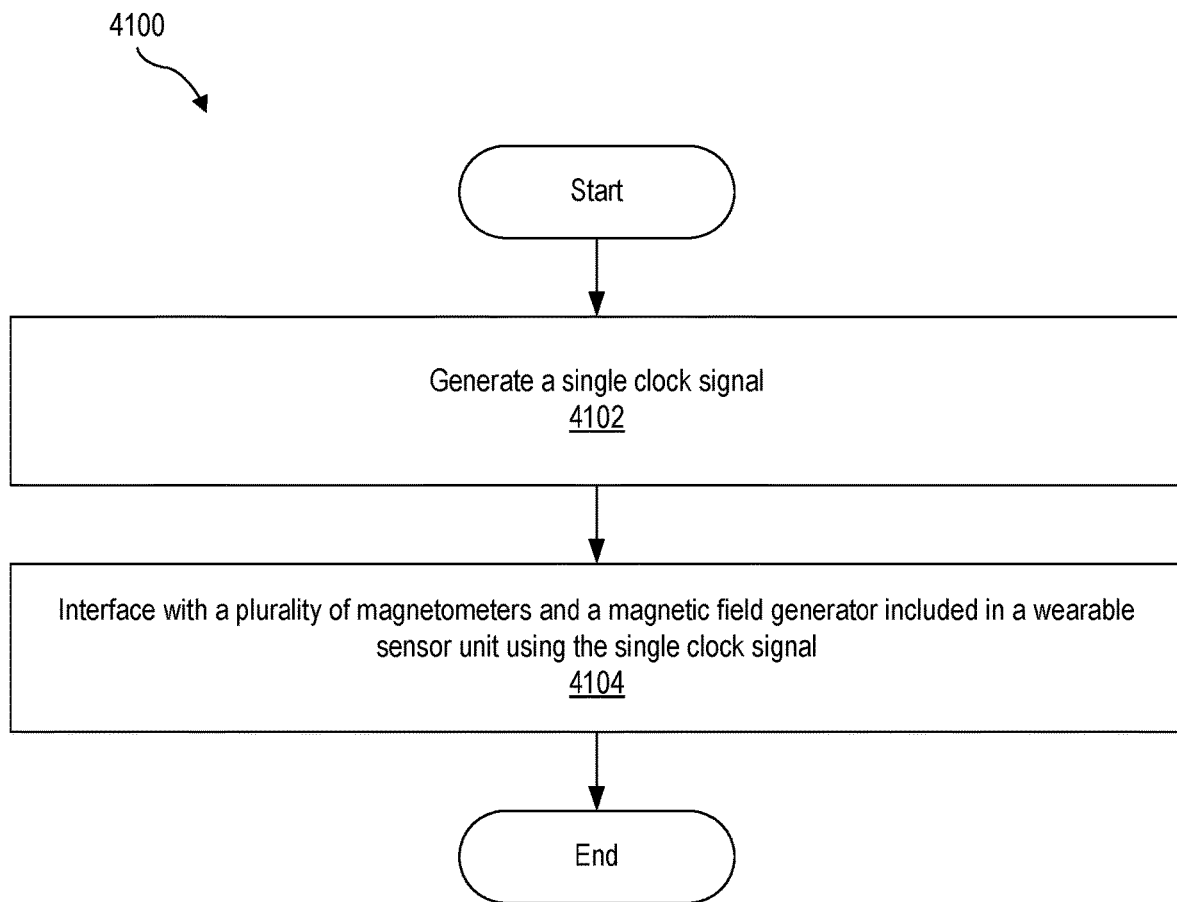
FIGS. 41-43 illustrate exemplary methods according to principles described herein.

FIG. 41 illustrates an exemplary method 4100 that may be performed by controller 104 and/or any implementation thereof. While FIG. 41 illustrates exemplary operations according to one embodiment, other embodiments may omit, add to, reorder, and/or modify any of the operations shown in FIG. 41.

In operation 4102, a controller generates a single clock signal. Operation 4102 may be performed in any of the ways described herein.

In operation 4104, the controller interfaces with a plurality of magnetometers and a magnetic field generator included in a wearable sensor unit using the single clock signal. Operation 4104 may be performed in any of the ways described herein.

Figure 42:
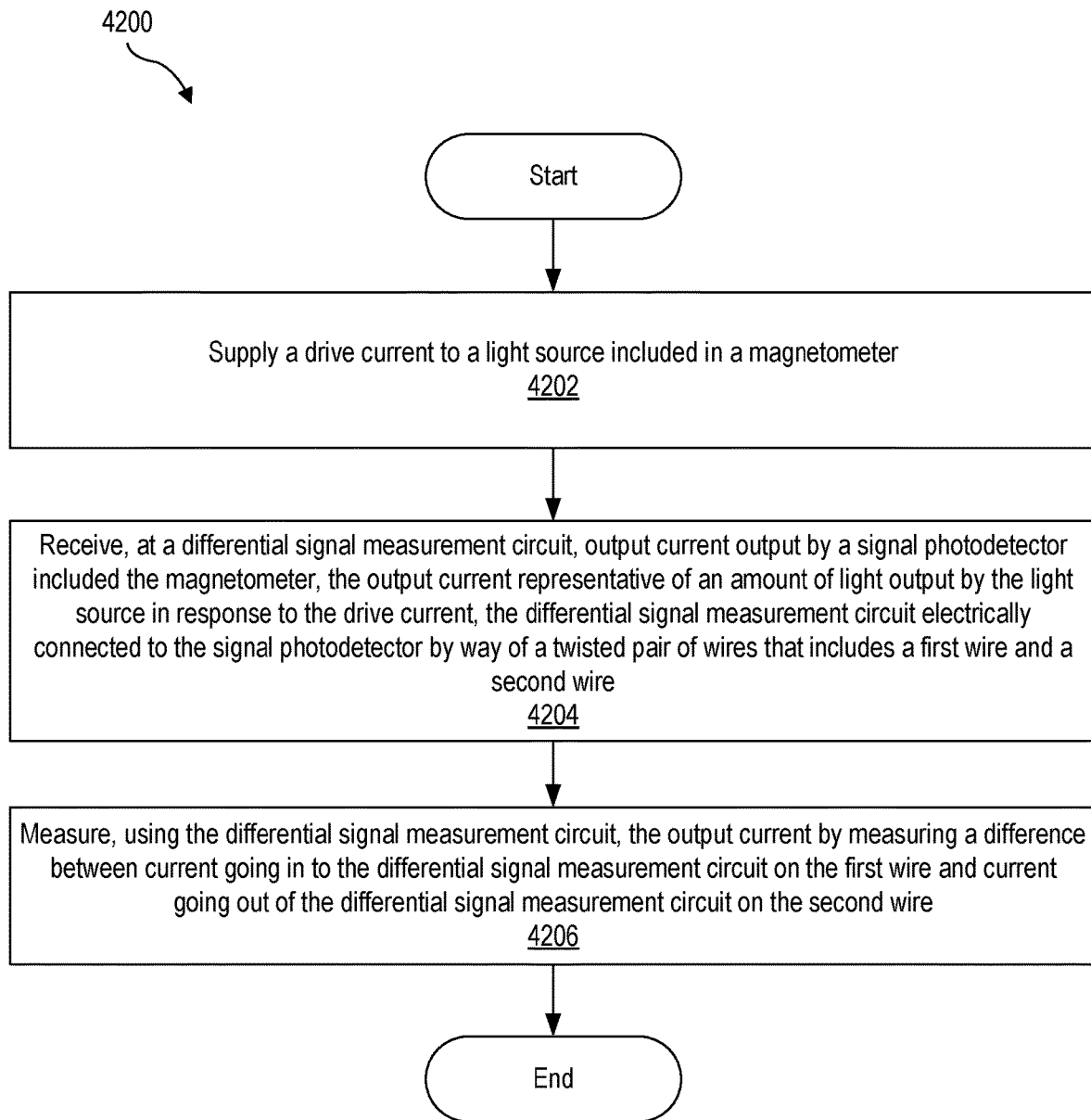

FIG. 42 illustrates another exemplary method 4200 that may be performed by controller 104 and/or any implementation thereof. While FIG. 42 illustrates exemplary operations according to one embodiment, other embodiments may omit, add to, reorder, and/or modify any of the operations shown in FIG. 42.

In operation 4202, a controller supplies a drive current to a light source included in a magnetometer. Operation 4202 may be performed in any of the ways described herein.

In operation 4204, the controller receives, at a differential signal measurement circuit, output current output by a signal photodetector included the magnetometer. The output current is representative of an amount of light output by the light source in response to the drive current. The differential signal measurement circuit is electrically connected to the signal photodetector by way of a twisted pair of wires that includes a first wire and a second wire. Operation 4204 may be performed in any of the ways described herein.

In operation 4206, the controller measures, using the differential signal measurement circuit, the output current by measuring a difference between current going in to the differential signal measurement circuit on the first wire and current going out of the differential signal measurement circuit on the second wire. Operation 4206 may be performed in any of the ways described herein.

Figure 43:
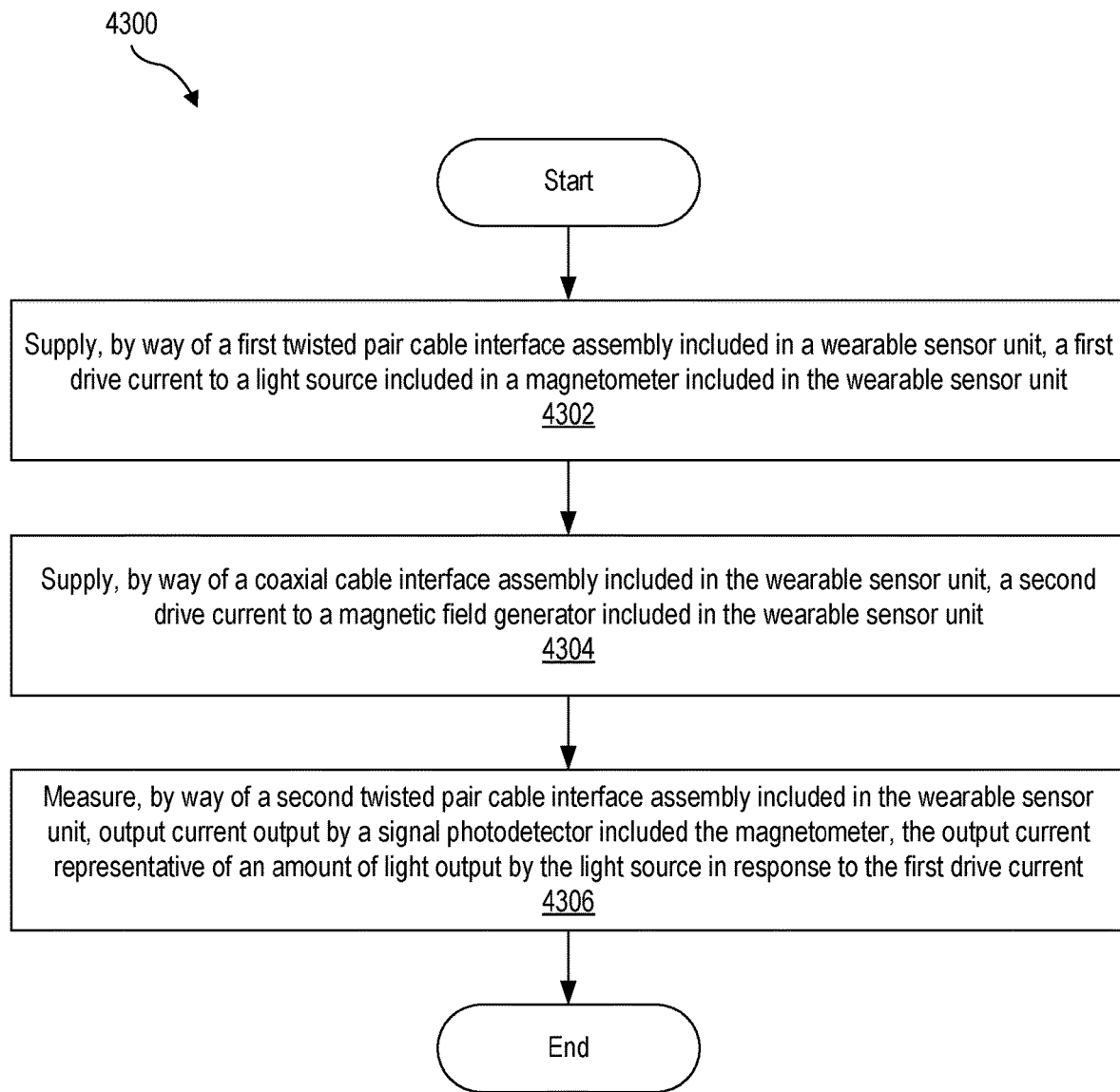

FIG. 43 illustrates another exemplary method 4300 that may be performed by controller 104 and/or any implementation thereof. While FIG. 43 illustrates exemplary operations according to one embodiment, other embodiments may omit, add to, reorder, and/or modify any of the operations shown in FIG. 43.

In operation 4302, a controller supplies, by way of a first twisted pair cable interface assembly included in a wearable sensor unit, a first drive current to a light source included in a magnetometer included in the wearable sensor unit. Operation 4302 may be performed in any of the ways described herein.

In operation 4304, the controller supplies, by way of a coaxial cable interface assembly included in the wearable sensor unit, a second drive current to a magnetic field generator included in the wearable sensor unit. Operation 4304 may be performed in any of the ways described herein.

In operation 4306, the controller measures, by way of a second twisted pair cable interface assembly included in the wearable sensor unit, output current output by a signal photodetector included the magnetometer. The output current is representative of an amount of light output by the light source in response to the first drive current. Operation 4306 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A magnetic field measurement system comprising:
   a wearable sensor unit comprising:
      a plurality of magnetometers, and
      a magnetic field generator configured to generate a compensation magnetic field configured to actively shield the magnetometers from ambient background magnetic fields; and
   a single controller configured to generate a single clock signal and use the single clock signal to drive one or more components within the magnetometers.

2. The magnetic field measurement system of claim 1, wherein the single controller is remote from the wearable sensor unit.

3. The magnetic field measurement system of claim 2, wherein the single controller is implemented by a computing device not configured to be worn by a user.

4. The magnetic field measurement system of claim 2, wherein the single controller is included in a wearable device configured to be worn by a user and separate from the wearable sensor unit.

5. The magnetic field measurement system of claim 1, wherein the single controller is housed within a single housing.

6. The magnetic field measurement system of claim 1, wherein the single controller is included within the wearable sensor unit.

7. The magnetic field measurement system of claim 1, further comprising:
   an additional wearable sensor unit comprising:
      an additional plurality of magnetometers, and
      an additional magnetic field generator configured to generate an additional compensation magnetic field configured to actively shield the additional plurality of magnetometers from the ambient background magnetic fields;
   wherein the single controller is further configured to interface with the additional plurality of magnetometers and the additional magnetic field generator.

8. The magnetic field measurement system of claim 7, wherein the single controller is included within the wearable sensor unit.

9. The magnetic field measurement system of claim 1, wherein the single controller is configured to interface with the magnetometers by way of one or more twisted pair cables.

10. The magnetic field measurement system of claim 1, wherein the single controller is configured to interface with the magnetic field generator by way of one or more coaxial cables.

11. The magnetic field measurement system of claim 1, wherein:
   a magnetometer included in the plurality of magnetometers comprises a photodetector; and
   the single controller comprises a differential signal measurement circuit configured to measure current output by the photodetector.

12. The magnetic field measurement system of claim 11, further comprising an unshielded cable configured to electrically connect the single controller to the wearable sensor unit.

13. The magnetic field measurement system of claim 11, wherein the photodetector comprises a signal photodetector configured to detect light output by a light source in the magnetometer after the light enters and exits a vapor cell of the magnetometer.

14. The magnetic field measurement system of claim 11, wherein the photodetector comprises a monitor photodetector configured to detect light output by a light source in the magnetometer before the light enters a vapor cell of the magnetometer.

15. The magnetic field measurement system of claim 1, wherein:
- a magnetometer included in the plurality of magnetometers comprises
  - a vapor cell comprising an input window and containing an alkali metal, and
  - a light source configured to output light that passes through the input window and into the vapor cell along a transit path; and
- the wearable sensor unit further comprises a temperature control circuit external to the vapor cell and configured to create a temperature gradient within the vapor cell, the temperature gradient configured to concentrate the alkali metal within the vapor cell away from the transit path of the light.

16. The magnetic field measurement system of claim 1, wherein the single controller is configured to interface with one or more components within the magnetometer using alternating current.

17. The magnetic field measurement system of claim 1, wherein:
- the magnetic field generator comprises:
  - a plurality of conductive windings comprising
    - a first conductive winding arranged in a first plane, and
    - a second conductive winding arranged in a second plane that is substantially parallel to the first plane;
  - the plurality of conductive windings are configured to generate, when supplied with one or more drive currents by the controller, a first component of the compensation magnetic field, the first component of the compensation magnetic field configured to actively shield a magnetic field sensing region from the ambient background magnetic fields along a first axis that is substantially orthogonal to the first plane and the second plane; and
- the magnetometers are located within the magnetic field sensing region.

18. The magnetic field measurement system of claim 17, wherein the first component of the compensation magnetic field is configured to actively shield the magnetic field sensing region by reducing or canceling a first component of the ambient background magnetic field, the first component of the ambient background magnetic field being along the first axis.

19. The magnetic field measurement system of claim 17, wherein the magnetic field generator further comprises:
- a first planar substrate;
- a second planar substrate positioned opposite to the first planar substrate and separated from the first planar substrate by a gap, the magnetic field sensing region being located in the gap;
- a first wiring disposed on the first planar substrate;
- a second wiring disposed on the second planar substrate; and
- one or more interconnects positioned between the first planar substrate and the second planar substrate and that electrically connect the first wiring with the second wiring to form a first continuous electrical path,
- wherein the first continuous electrical path forms a third conductive winding configured to generate, when supplied with a first additional drive current, a second component of the compensation magnetic field configured to actively shield the magnetic field sensing region from the ambient background magnetic field along a second axis that is substantially orthogonal to the first axis.

20. The magnetic field measurement system of claim 19, wherein the magnetic field generator further comprises:
- a third wiring disposed on the first planar substrate; and
- a fourth wiring disposed on the second planar substrate;
- wherein the one or more interconnects electrically connect the third wiring with the fourth wiring to form a second continuous electrical path; and
- wherein the additional continuous electrical path forms a fourth conductive winding configured to generate, when supplied with a second additional drive current, a third component of the compensation magnetic field configured to actively shield the magnetic field sensing region from the ambient background magnetic fields along a third axis that is substantially orthogonal to the first axis and the second axis.

* * * * *